United States Patent
Lu et al.

(10) Patent No.: US 12,110,337 B2
(45) Date of Patent: Oct. 8, 2024

(54) ANTI-CD27 ANTIBODIES AND USES THEREOF

(71) Applicant: BRISTOL-MYERS SQUIBB COMPANY, Princeton, NJ (US)

(72) Inventors: Li-Sheng Lu, Mountain View, CA (US); Mark J. Selby, San Francisco, CA (US); Alan J. Korman, Piedmont, CA (US); Shrikant Deshpande, Fremont, CA (US); Mohan Srinivasan, Cupertino, CA (US); Jun Zhang, Pleasanton, CA (US); Haichun Huang, Fremont, CA (US); Guodong Chen, East Brunswick, NJ (US); Richard Y. Huang, Bridgewater, NJ (US); Ekaterina Deyanova, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 456 days.

(21) Appl. No.: 17/045,143

(22) PCT Filed: Apr. 3, 2019

(86) PCT No.: PCT/US2019/025623
§ 371 (c)(1),
(2) Date: Oct. 2, 2020

(87) PCT Pub. No.: WO2019/195452
PCT Pub. Date: Oct. 10, 2019

(65) Prior Publication Data
US 2021/0155703 A1    May 27, 2021

Related U.S. Application Data

(60) Provisional application No. 62/652,790, filed on Apr. 4, 2018.

(51) Int. Cl.
*C07K 16/28* (2006.01)
*A61K 39/395* (2006.01)
(Continued)

(52) U.S. Cl.
CPC .... *C07K 16/2878* (2013.01); *A61K 39/39541* (2013.01); *A61P 35/00* (2018.01);
(Continued)

(58) Field of Classification Search
None
See application file for complete search history.

(56) References Cited

U.S. PATENT DOCUMENTS 7,943,743 B2    5/2011    Korman et al.
8,008,449 B2    8/2011    Korman et al.
(Continued)

FOREIGN PATENT DOCUMENTS

WO    2011130434 A2    10/2011
WO    2012145493 A1    10/2012
(Continued)

OTHER PUBLICATIONS

GenBank Database, Accession No. NP_001400196.1, CD27 antigen isoform e [*Homo sapiens*], Retrieved online: <URL:<span style="font-family: "Windows Arial Unicode";" >https://www.ncbi.nlm.nih.gov/protein/NP_001400196.1> [retrieved Feb. 21, 2023], Jan. 1, 2023.</span>.*

(Continued)

*Primary Examiner* — Claire Kaufman
(74) *Attorney, Agent, or Firm* — Ashton J. Delauney

(57) ABSTRACT

This disclosure provides isolated antibodies that bind specifically to CD27 with high affinity. The disclosure provides methods for treating a subject afflicted with a cancer comprising administering to the subject a therapeutically effective amount of an anti-CD27 antibody as monotherapy or in
(Continued)

BMS-986215 combination with a checkpoint inhibitor, such as an anti-PD-1, anti-PD-L1, or anti-CTLA-4 antibody.

25 Claims, 26 Drawing Sheets

Specification includes a Sequence Listing.

(51) Int. Cl.
*A61P 35/00* (2006.01)
*A61K 39/00* (2006.01)

(52) U.S. Cl.
CPC .... *A61K 2039/505* (2013.01); *C07K 2317/33* (2013.01); *C07K 2317/34* (2013.01); *C07K 2317/565* (2013.01); *C07K 2317/74* (2013.01); *C07K 2317/75* (2013.01); *C07K 2317/92* (2013.01)

(56) References Cited

U.S. PATENT DOCUMENTS

| | | | |
|---|---|---|---|
| 8,217,149 B2 | 7/2012 | Irving et al. | |
| 9,527,916 B2 * | 12/2016 | Van Eenennaam | A61P 37/06 |
| 9,683,046 B2 * | 6/2017 | Chen | A61P 31/00 |

FOREIGN PATENT DOCUMENTS

| | | |
|---|---|---|
| WO | 2013138586 A1 | 9/2013 |
| WO | 2013173223 A1 | 11/2013 |
| WO | 2015112900 A1 | 7/2015 |
| WO | 2016145085 A2 | 9/2016 |
| WO | 2016149201 A2 | 9/2016 |
| WO | 2018058022 A1 | 3/2018 |

OTHER PUBLICATIONS

GenBank Database, Accession No. XP_047285856.1, <span style= "font-family: "Windows Arial Unicode";" >CD27 antigen isoform X2 [*Homo sapiens*]</span> Retrieved online: <URL:https://www. https://www.ncbi.nlm.nih.gov/protein/XP_047285856.1> [retrieved Feb. 21, 2023], Apr. 5, 2022.*
GenBank Database, Accession No. AAH12160.1, CD27 antigen isoform e [*Homo sapiens*], Retrieved online: <URL:https://www. ncbi.nlm.nih.gov/protein/AAH12160.1> [retrieved Feb. 21, 2023], Nov. 7, 2006.*
<P class="MsoNormal" style="line-height:150%;mso-layout-grid-align:none; text-autospace:none" ><span style="mso-bidi-font-size:12.0pt;line-height:150%; color:windowtext" >Fadeel et al., Anti-Fas IgG1 antibodies recognizing the same epitope of Fas/APO-1 mediate different biological effects in vitro, Intl.*
Nair et al., Epitope Recognition by Diverse Antibodies Suggests Conformational Convergence in an Antibody Response, J. Immunol. 168:2371-2382, 2002.*
MacCallum et al.,Antibody-antigen interactions: contact analysis and binding site topography, J. Mol. Biol. 262:732-745, 1996.*
Chen et al., Enhancement and destruction of antibody function by somatic mutation: unequal occurrence is controlled by V gene combinatorial associations, EMBO J. 14(12):2784-2794, 1995.*
Herold et al., Determinants of the assembly and function of antibody variable domains, Scientific Reports, 7:12276, 17 pages, DOI: 10.1038/s41598-017-12519-9, Sep. 2017.*
Kunik et al., Structural consensus among antibodies defines the antigen binding site, PLoS Comput. Biol. 8(2):e1002388, 12 pages, doi:10.1371/journal.pcbi.1002388, 2012.*
Sela-Culang et al., The structural basis of antibody-antigen recognition, Front. Immunol. 4:302, 13 pages, doi: 10.3389/fimmu.2013. 00302, Oct. 2018.*
Yan et al., Construction of a synthetic phage-displayed Nanobody library with CDR3 regions randomized by trinucleotide cassettes for diagnostic J. Translational Med. 12:343, 12 pages, http://www. translational-medicine.com/content/12/1/343, 2014.*
Ahrends T, Babala N, Xiao Y et al. (2016) "CD27 agonism plus PD-1 blockade recapitulates CD4+ T cell help in therapeutic anti-cancer vaccination". Cancer Res 76(10):2921-31.
Baitsch L, Legat A, Barba L, Fuertes Marraco SA, Rivals JP et al. (2012) "Extended co-expression of inhibitory receptors by human CD8 T-cells depending on differentiation, antigen-specificity and anatomical localization". PloS One 7(2): e30852.
Brahmer JR, Hammers H, Lipson EJ (2015) "Nivolumab: targeting PD-1 to bolster antitumor immunity". Future Oncol 11(9):1307-26.
Buchan SL, Fallatah M, Thirdborough SM, Taraban VY, Rogel A et al. (2018) "PD-1 blockade and CD27 stimulation activate distinct transcriptional programs that synergize for CD8+ T-cell driven anti-tumor immunity". Clin Cancer Res 24(10):2383-94.
Buchan SL, Manzo T, Flutter B et al. (2015) "OX40- and CD27-mediated costimulation synergizes with anti-PD-L1 blockade by forcing exhausted CD8+ T cells to exit quiescence". J Immunol 194:125-33.
Bullock et al., "Immune correlates of varlilumab (CDX-1127) treated cancer patients are consistent with CD27 costimulatory activity". Society for Immunotherapy of Cancer (SITC) 29th Annual Meeting, Nov. 6-9, 2014, National Habor, MD; Celldex Poster P115 (2014).
Wang, K.B. Thudium, M. Han, X.T. Wang, H. Huang, D. Feingersh, C. Garcia, Y. Wu, M. Kuhne, M. Srinivasan, S. Singh, S. Wong, N. Garner, H. Leblanc, R.T. Bunch, D. Blanset, M.J. Selby, A.J. Korman, In vitro characterization of the anti-PD-1 antibody nivolumab, BMS-936558, and in vivo toxicology in non-human primates, Cancer immunology research, 2 (2014) 846-856.
Callahan M, Postow MA, Wolchok JD (2016) "Targeting T cell co-receptors for cancer therapy". Immunity 44 (5):1069-78.
De Colvenaer V, Taveirne S, Delforche M et al. (2011) "CD27-deficient mice show normal NK-cell differentiation but impaired function upon stimulation". Immunol Cell Biol 89:803-11.
French RR, Taraban VY, Crowther GR et al. (2007) "Eradication of lymphoma by CD8 T cells following anti-CD40 monoclonal antibody therapy is critically dependent on CD27 costimulation". Blood 109:4810-5.
He LZ, Prostak N, Thomas LJ et al. (2013) "Agonist anti-human CD27 monoclonal antibody induces T cell activation and tumor immunity in human CD27-transgenic mice". J Immunol 191:4174-83.
Hendriks J, Gravestein LA, Tesselaar K et al. (2000) "CD27 is required for generation and long-term maintenance of T cell immunity". Nat Immunol 1:433-40.
Iwai Y, Hamanishi J, Chamoto K, Honjo T (2017) "Cancer immunotherapies targeting the PD-1 signaling pathway". J Biomed Sci 24(1):26.
Kamta J, Chaar M, Ande A, Altomare DA, Ait-Oudhia S (2017) "Advancing cancer therapy with present and emerging immuno-oncology approaches". Front Oncol 18(7):64.
Lesokhin AM, Callahan MK, Postow MA, Wolchok JD (2015) "On being less tolerant: enhanced cancer immunosurveillance enabled by targeting checkpoints and agonists of T cell activation". Sci Transl Med 7(280):280sr1.
Mahoney et al., "Combination cancer immunotherapy and new immunomodulatory targets". Nat Rev Drug Discov 14 (8):561-84. (2015).
Munitic I, Kuka M, Allam A et al. (2013) "CD70 deficiency impairs effector CD8 T cell generation and viral clearance but is dispensable for the recall response to lymphocytic choriomeningitis virus". J Immunol 190:1169-79.
Obmolova et al., "Epitope-dependent mechanisms of CD27 neutralization revealed by X-ray crystallography", Molecular Immunology vol. 83, Jan. 21, 2017, pp. 92-99. (2017).
Pianko et al., "Immune checkpoint blockade for hematologic malignancies: a review". Stem Cell Investig 4:32. (2017).
Ramakrishna, et al., "Characterization of the human T cell response to in vitro CD27 costimulation with varlilumab". J Immunother Cancer 3:37. (2015).
Roberts DJ, Franklin NA, Kingeter LM et al. (2010) "Control of established melanoma by CD27 stimulation is associated with

(56) References Cited

OTHER PUBLICATIONS enhanced effector function and persistence, and reduced PD-1 expression, of tumor infiltrating CD8+ T cells". J Immunother 33:769-79.

Sakanishi et al., "Anti-tumor effects of depleting and non-depleting anti-CD27 mAbs in immune-competent mice". Biochem Biophys Res Commun 393:829-35 (2010).

Salzer E, Daschkey S, Choo S et al. (2013) "Combined immunodeficiency with life-threatening EBV-associated lymphoproliferative disorder in patients lacking functional CD27". Haematologica 98:473-8.

Sanborn et al. (2017), "Clinical results with combination of anti-CD27 agonist antibody, varlilumab, with anti-PD1 antibody nivolumab in advanced cancer patients". J Clin Oncol 35(15) Suppl.:3007.

Sanchez PJ, McWilliams JA, Haluszczak C et al. (2007) "Combined TLR/CD40 stimulation mediates potent cellular immunity by regulating dendritic cell expression of CD70 in vivo". J Immunol 178:1564-72.

Teplyakov et al. "Crystal structure of CD 27 in complex with a neutralizing noncompeting antibody", Acta Crystallogtaphica Section F Structural Biology Communications, vol. 73, No. 5, May 1, 2017 (May 1, 2017), pp. 294-299, XP055435778.

Van Gisbergen KP, Klarenbeek PL, Kragten NA, et al. (2011) The costimulatory molecule CD27 maintains clonally diverse CD8 (+) T cell responses of low antigen affinity to protect against viral variants. Immunity 35:97-108.

Van Montfrans JM, Hoepelman AI, Otto S et al. (2012) CD27 deficiency is associated with combined immunodeficiency and persistent symptomatic EBV viremia. Allergy Clin Immunol 129:787-93.

Wajant H (2016) Therapeutic targeting of CD70 and CD27. Expert Opin Ther Targets 20(8):959-73.

Yao S, Zhu Y, Chen L (2013) Advances in targeting cell surface signalling molecules for immune modulation. Nature Rev Drug Discov 12:130-46.

\* cited by examiner

SEQUENCE LISTING

```
<160> NUMBER OF SEQ ID NOS: 21

<210> SEQ ID NO 1
<211> LENGTH: 260
<212> TYPE: PRT
<213> ORGANISM: Homo sapiens

<400> SEQUENCE: 1

Met Ala Arg Pro His Pro Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
                35                  40                  45

Leu Val Lys Asp Cys Asp Gln His Arg Lys Ala Ala Gln Cys Asp Pro
            50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                    85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
                180                 185                 190

Leu Val Ile Phe Ser Gly Met Phe Leu Val Phe Thr Leu Ala Gly Ala
            195                 200                 205

Leu Phe Leu His Gln Arg Arg Lys Tyr Arg Ser Asn Lys Gly Glu Ser
        210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 2
<211> LENGTH: 6
<212> TYPE: PRT
<213> ORGANISM: Artificial Sequence
<220> FEATURE:
<223> OTHER INFORMATION: VH CDR1 of BMS-986215

<400> SEQUENCE: 2

Thr Thr Tyr Ala Met Asn
1               5
```

```
<210> SEQ ID NO 3
<211> LENGTH: 17
<212> TYPE: PRT
<213> ORGANISM: Artificial Sequence
<220> FEATURE:
<223> OTHER INFORMATION: VH CDR2 of BMS-986215

<400> SEQUENCE: 3

Trp Ile Asn Thr Asn Thr Gly Asn Pro Thr Tyr Ala Gln Gly Phe Thr
1               5                   10                  15

Gly

<210> SEQ ID NO 4
<211> LENGTH: 7
<212> TYPE: PRT
<213> ORGANISM: Artificial Sequence
<220> FEATURE:
<223> OTHER INFORMATION: VH CDR3 of BMS-986215

<400> SEQUENCE: 4

Asp Phe Gly Gly Phe Asp Tyr
1               5

<210> SEQ ID NO 5
<211> LENGTH: 11
<212> TYPE: PRT
<213> ORGANISM: Artificial Sequence
<220> FEATURE:
<223> OTHER INFORMATION: VL CDR1 of BMS-986215

<400> SEQUENCE: 5

Arg Ala Ser Gln Gly Ile Ser Ser Ala Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: VL CDR2 of BMS-986215

<400> SEQUENCE: 6

Asp Ala Ser Ser Leu Glu Ser
1               5

<210> SEQ ID NO 7
<211> LENGTH: 9
<212> TYPE: PRT
<213> ORGANISM: Artificial Sequence
<220> FEATURE:
<223> OTHER INFORMATION: VL CDR3 of BMS-986215

<400> SEQUENCE: 7

Gln Gln Phe Asn Asn Tyr Pro Arg Thr
1               5

<210> SEQ ID NO 8
<211> LENGTH: 116
<212> TYPE: PRT
<213> ORGANISM: Artificial Sequence
<220> FEATURE:
<223> OTHER INFORMATION: VH of BMS-986215

<400> SEQUENCE: 8

Gln Val Gln Leu Val Gln Ser Gly Ser Glu Val Lys Lys Pro Gly Ala
1               5                   10                  15
```

```
Ser Val Lys Val Ser Cys Lys Ala Ser Gly Tyr Thr Phe Thr Thr Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Phe Gly Gly Phe Asp Tyr Trp Gly Gln Gly Thr Leu Val
            100                 105                 110

Thr Val Ser Ser
            115

<210> SEQ ID NO 9
<211> LENGTH: 107
<212> TYPE: PRT
<213> ORGANISM: Artificial Sequence
<220> FEATURE:
<223> OTHER INFORMATION: VL of BMS-986215

<400> SEQUENCE: 9

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Asn Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Arg
                85                  90                  95

Thr Phe Gly Gln Gly Thr Lys Val Glu Ile Lys
            100                 105

<210> SEQ ID NO 10
<211> LENGTH: 329
<212> TYPE: PRT
<213> ORGANISM: Artificial Sequence
<220> FEATURE:
<223> OTHER INFORMATION: CH of BMS-986215

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                        85                  90                  95
Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 11
<211> LENGTH: 107
<212> TYPE: PRT
<213> ORGANISM: Artificial Sequence
<220> FEATURE:
<223> OTHER INFORMATION: CL of BMS-986215

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 12
<211> LENGTH: 445
<212> TYPE: PRT
<213> ORGANISM: Artificial Sequence
<220> FEATURE:
<223> OTHER INFORMATION: heavy chain of BMS-986215

<400> SEQUENCE: 12

Gln Val Gln Leu Val Gln Ser Gly Ser Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Phe Gly Gly Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
                370              375              380
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445
```

<210> SEQ ID NO 13
<211> LENGTH: 214
<212> TYPE: PRT
<213> ORGANISM: Artificial Sequence
<220> FEATURE:
<223> OTHER INFORMATION: light chain of BMS-986215

<400> SEQUENCE: 13

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Asn Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 14
<211> LENGTH: 178
<212> TYPE: PRT
<213> ORGANISM: Homo sapiens

<400> SEQUENCE: 14

```
Thr Pro Ala Pro Lys Ser Cys Pro Glu Arg His Tyr Trp Ala Gln Gly
1               5                   10                  15

Lys Leu Cys Cys Gln Met Cys Glu Pro Gly Thr Phe Leu Val Lys Asp
            20                  25                  30
```

Cys Asp Gln His Arg Lys Ala Ala Gln Cys Asp Pro Cys Ile Pro Gly
                35                  40                  45

Val Ser Phe Ser Pro Asp His His Thr Arg Pro His Cys Glu Ser Cys
         50                  55                  60

Arg His Cys Asn Ser Gly Leu Leu Val Arg Asn Cys Thr Ile Thr Ala
 65                  70                  75                  80

Asn Ala Glu Cys Ala Cys Arg Asn Gly Trp Gln Cys Arg Asp Lys Glu
                 85                  90                  95

Cys Thr Glu Cys Asp Pro Leu Pro Asn Pro Ser Leu Thr Ala Arg Ser
            100                 105                 110

Ser Gln Ala Leu Ser Pro His Pro Gln Pro Thr His Leu Pro Tyr Val
                115                 120                 125

Ser Glu Met Leu Glu Ala Arg Thr Ala Gly His Met Gln Thr Leu Ala
            130                 135                 140

Asp Phe Arg Gln Leu Pro Ala Arg Thr Leu Ser Thr His Trp Pro Pro
145                 150                 155                 160

Gln Arg Ser Leu Cys Ser Ser Asp Phe Ile Arg Ile His His His His
                165                 170                 175

His His

<210> SEQ ID NO 15
<211> LENGTH: 21
<212> TYPE: PRT
<213> ORGANISM: Homo sapiens

<400> SEQUENCE: 15

Thr Pro Ala Pro Lys Ser Cys Pro Glu Arg His Tyr Trp Ala Gln Gly
1               5                   10                  15

Lys Leu Cys Cys Gln
            20

<210> SEQ ID NO 16
<211> LENGTH: 7
<212> TYPE: PRT
<213> ORGANISM: homo sapiens

<400> SEQUENCE: 16

His Tyr Trp Ala Gln Gly Lys
1               5

<210> SEQ ID NO 17
<211> LENGTH: 14
<212> TYPE: PRT
<213> ORGANISM: Homo sapiens

<400> SEQUENCE: 17

Leu Cys Cys Gln Met Cys Glu Pro Gly Thr Phe Leu Val Lys
1               5                   10

<210> SEQ ID NO 18
<211> LENGTH: 6
<212> TYPE: PRT
<213> ORGANISM: Homo sapiens

<400> SEQUENCE: 18

Asp Cys Asp Gln His Arg
1               5

<210> SEQ ID NO 19

<211> LENGTH: 6
<212> TYPE: PRT
<213> ORGANISM: Homo sapiens

<400> SEQUENCE: 19

Asn Gly Trp Gln Cys Arg
1               5

<210> SEQ ID NO 20
<211> LENGTH: 452
<212> TYPE: PRT
<213> ORGANISM: Artificial Sequence
<220> FEATURE:
<223> OTHER INFORMATION: 1F5 Heavy Chain

<400> SEQUENCE: 20

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Ser Ser
    450

<210> SEQ ID NO 21
<211> LENGTH: 214
<212> TYPE: PRT
<213> ORGANISM: Artificial Sequence
<220> FEATURE:
<223> OTHER INFORMATION: 1F5 Light Chain

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-CD27 ANTIBODIES AND USES THEREOF

CROSS REFERENCE TO RELATED APPLICATION

This application is a 35 U.S.C. § 371 national stage application of International Application No. PCT/US2019/025623, filed Apr. 3, 2019, which claims the benefit of U.S. Provisional Application No. 62/652,790, filed Apr. 4, 2018, the content of which is hereby incorporated herein by reference in its entirety.

Throughout this application, various publications are referenced in parentheses by author name and date, or by patent No. or patent Publication No. Full citations for these publications may be found at the end of the specification immediately preceding the claims. The disclosures of these publications are hereby incorporated in their entireties by reference into this application in order to more fully describe the state of the art as known to those skilled therein as of the date of the invention described and claimed herein. However, these disclosures are incorporated by reference into the present application only to the extent that no conflict exists between the incorporated information and the information provided by explicit disclosure herein. Moreover, the citation of a reference herein should not be construed as an acknowledgement that such reference is prior art to the present invention.

REFERENCE TO SEQUENCE LISTING SUBMITTED ELECTRONICALLY VIA EFS-WEB

The content of the electronically submitted sequence listing (Name: 13107-WO-PCT_ST25.txt, Size: 23,885 bytes; and Date of Creation: Apr. 1, 2019) submitted in this application is incorporated herein by reference in its entirety.

FIELD OF THE INVENTION

This invention relates to monoclonal antibodies (mAbs) that bind specifically to CD27 and methods for treating a cancer in a subject comprising administering to the subject an anti-CD27 antibody (Ab) as monotherapy or in combination with an anticancer agent such as an immune checkpoint inhibitor and/or certain chemotherapeutics and radiation therapies.

BACKGROUND OF THE INVENTION

Human cancers harbor numerous genetic and epigenetic alterations, generating neoantigens potentially recognizable by the immune system (Chakravarthi et al., 2016). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system makes immunotherapy unique among all cancer treatment modalities.

The past decade has witnessed the development of specific immune checkpoint pathway inhibitors for treating cancer (Chen and Mellman, 2013; Lesokhin et al., 2015), including the development of an Ab, ipilimumab (YERVOY®), that binds to and inhibits Cytotoxic T-Lymphocyte Antigen-4 (CTLA-4) for the treatment of patients with advanced melanoma, and Abs such as nivolumab (OPDIVO®), pembrolizumab (KEYTRUDA®) and cemiplimab-rwlc (LIBTAYO®) that bind specifically to the PD-1 receptor and block the inhibitory PD-1/PD-1 ligand (PD-L1) signaling pathway (Iwai et al., 2017). This pathway can also be disrupted by Abs, including atezolizumab (TECENTRIQ®), durvalumab (IMFINZI®), and avelumab (BAVENCIO®), that bind specifically to PD-L1.

Nivolumab is a fully human immunoglobulin (Ig) G4 (S228P) mAb that selectively prevents interaction with the PD-1 ligands, PD-L1 and PD-L2 (U.S. Pat. No. 8,008,449; Wang et al., 2014), thereby blocking the down-regulation of antigen-specific T cell responses directed against both foreign (including tumor) and self antigens and enhancing an immune response against these antigens. Nivolumab has received approval recently for several cancers including melanoma, lung cancer, renal cell carcinoma, classical Hodgkin lymphoma, head and neck cancer, urothelial carcinoma, MSI-H or dMMR metastatic colorectal cancer, and hepatocellular carcinoma, and is currently being clinically evaluated as monotherapy or in combination with other anti-cancer agents in additional tumor types. However, only a small percentage of patients, typically less than around 25%, benefit from treatment with checkpoint inhibitors, and considerable efforts are now focused on improving the efficacy of immunotherapy using combinations of checkpoint inhibitors and other anti-cancer agents or therapies. Because PD-1/PD-L1 inhibitors have proven to be so successful in treating a broad spectrum of cancers, they are perceived to be the likely backbone of various future drug combinations in immuno-oncology and a race is on to develop the most effective combinations (see, e.g., Mahoney et al., 2015; Ott et al., 2017).

CD27, a 55 kDa type I transmembrane protein in the tumor necrosis factor receptor (TNFR) family, costimulates T-cell activation after binding to its ligand CD70. In humans, CD27 is constitutively and exclusively expressed by naïve T cells and upregulated on activated T cells and B cells, while the expression of CD70, a type II transmembrane protein, is highly regulated and occurs only transiently on activated T cells, B cells, and dendritic cells (DCs) (Wajant, 2016). CD27 plays an important role in expansion of naïve T cells, enhancement of effector function, and generation and long-term maintenance of T cell immunity and the responder T cell pool (Hendricks et al., 2000). CD27-deficient mice display a reduction of T-cell immunity, memory to influenza virus, and cytolytic activity of activated NK cells (Hendricks et al., 2000; De Colvenaer et al., 2011), whereas CD70 deficiency impairs effector CD8$^+$ T cell generation and viral clearance (Munitic et al., 2013). CD27 is expressed at higher levels in human peripheral blood than in human tumors, with Tregs expressing a higher level of CD27 than CD4$^+$ T cells. CD27-driven costimulation lowers the threshold of T cell receptor activation on CD8$^+$ T cells and is thought to enable responses against low-affinity antigens, broadening the functional T-cell repertoire (van Gisbergen et al., 2011). Blocking CD27-CD70 interaction reduces primary CD8$^+$ T cell responses (Taraban et al., 2004; Sanchez et al., 2007) and results in diminished CD8$^+$ T cell memory (Dolfi et al., 2008). Importantly, blockade of CD27 costimulation completely abrogates anti-CD40 therapeutic response in a mouse lymphoma model (French et al., 2007).

CD27 plays a role in early generation of a primary immune response and is required for generation and long-term maintenance of T cell immunity. CD27-CD70 binding leads to activation of NF-κB and MAPK8/JNK pathways. Adaptor proteins TRAF2 and TRAF5 have been shown to mediate the signaling resulting from CD27 engagement. Evidence for the clinical relevance of active CD27 in maintaining adequate immune function is demonstrated by the life-threatening EBV-associated lymphoproliferative disorder or persistent EBV viremia in patients lacking functional CD27 (Salzer et al., 2013; van Montfrans et al., 2012).

Enhanced T cell stimulation by CD27 agonism is manifested by increased proliferation and secretion of IFN-γ (Ramakrishna et al., 2015). In ex vivo studies using peripheral blood mononuclear cells (PBMCs) from melanoma patients, CD27 agonist treatment increased the response of CD8+ T cells to melanoma antigens with production of IFN-γ (Bullock et al., 2014). CD27 agonist-mediated costimulation has been shown to synergize with coinhibitory checkpoint PD-L1 blockade by forcing exhausted CD8+ T cells to exit quiescence in non-tumor bearing mouse studies (Buchan et al., 2015). Preclinical studies have shown that anti-CD27 agonist treatment inhibits experimental lung metastases (Roberts et al., 2010) and suppresses growth of syngeneic tumors (French et al., 2007; Roberts et al., 2010; He et al., 2013; Sakanishi and Yagita, 2010). CD27 agonism with PD-1 blockade has also been shown to increase antigen-specific CTL responses that are effective in eradicating TC-1 tumors (Ahrends et al., 2016), and an anti-human CD27 agonist monoclonal antibody (mAb), varlilumab, synergizes with PD-L1 blockade for protection against lymphoma in human-CD27 transgenic mice (Buchan et al., 2018). Varlilumab is undergoing clinical trials in combination with the anti-PD-1 mAb, nivolumab, in a variety of cancer patients and so far has been shown to be well tolerated and has provided preliminary evidence of clinical activity in subsets of patients with tumor types that are typically resistant to PD-1 inhibitor monotherapy (Sanborn et al., 2017).

The present disclosure relates to an evaluation of non-ligand blocking CD27 agonist antibodies (Abs) in the induction of antitumor immunity and maintenance of CD70-mediated costimulation and agonism. The disclosure also relates to an evaluation of the combination of non-ligand blocking CD27 agonist Abs with checkpoint blockade therapy on antitumor activity. There remains a need for high-affinity, non-ligand blocking anti-CD27 Abs exhibiting potent agonistic activities that enhance antitumor immune responses.

SUMMARY OF THE INVENTION

The present invention relates to a mAb or an antigen-binding portion thereof that specifically binds to human CD27 (hCD27) and does not block binding of its CD70 ligand as measured by surface plasmon resonance (SPR) or flow cytometry, wherein the Ab or fragment thereof: (a) binds to hCD27 with a $K_D$ of about 100 nM or lower, about 90 nM or lower, about 80 nM or lower, about 70 nM or lower, about 60 nM or lower, about 50 nM or lower, about 40 nM or lower, between about 1 nM and about 100 nM, between about 10 nM and about 70 nM, between about 10 nM and about 50 nM, or between about 40 nM and about 45 nM, and/or (b) induces NF-κB and MAPK signaling with an $EC_{50}$ of about 0.5 nM or lower, about 0.4 nM or lower, about 0.3 nM or lower, between about 0.005 nM and about 0.5 nM, between about 0.01 nM and about 0.4 nM, or between about 0.02 nM and about 0.25 nM in naïve human T cells stimulated by an anti-CD3 Ab and an anti-CD28 Ab.

The present invention relates to a mAb or an antigen-binding portion thereof that specifically binds to an epitope located within discontinuous regions spanning approximately amino acid residues 21 to 41 and 52 to 57 of hCD27, a sequence of which is SEQ ID NO: 1, as determined by hydrogen-deuterium exchange mass spectrometry (HDX-MS) and/or fast photochemical oxidation of proteins (FPOP) epitope mapping.

The present invention relates to a mAb or an antigen-binding portion thereof that specifically binds to hCD27, comprising: (a) a heavy chain variable region ($V_H$) comprising a CDR1 comprising consecutively linked amino acids having the sequence set forth as SEQ ID NO: 2, a CDR2 comprising consecutively linked amino acids having the sequence set forth as SEQ ID NO: 3, and a CDR3 comprising consecutively linked amino acids having the sequence set forth as SEQ ID NO: 4; and (b) a light chain variable region ($V_L$) comprising a CDR1 comprising consecutively linked amino acids having the sequence set forth as SEQ ID NO: 5, a CDR2 comprising consecutively linked amino acids having the sequence set forth as SEQ ID NO: 6, and a CDR3 comprising consecutively linked amino acids having the sequence set forth as SEQ ID NO: 7. In certain embodiments, the $V_H$ comprises consecutively linked amino acids having the sequence set forth as SEQ ID NO: 8. In certain embodiments, the $V_L$ comprises consecutively linked amino acids having the sequence set forth as SEQ ID NO: 9. In certain embodiments, the mAb comprises a heavy chain comprising consecutively linked amino acids having the sequence set forth as SEQ ID NO: 12 and a light chain comprising consecutively linked amino acids having the sequence set forth as SEQ ID NO: 13. In certain embodiments, the mAb is the mAb designated BMS-986215.

The present invention relates to a mAb or an antigen-binding portion thereof that specifically binds to substantially the same epitope of hCD27 as the mAb or antigen-binding portion thereof of any one of the above mAbs or antigen-binding portions thereof. The invention further relates to a mAb or an antigen-binding portion thereof that cross-competes with a reference Ab or a reference antigen-binding portion thereof for binding to hCD27.

Any of the above mAbs or antigen-binding portions thereof are referred to in the following embodiments as anti-CD27 mAbs or an antigen-binding portions thereof.

In certain embodiments, any of the anti-CD27 mAbs or antigen-binding portions thereof has one or more characteristics selected from the group consisting of: (a) does not inhibit CD70 binding to CD27 as measured by surface plasmon resonance (SPR) or flow cytometry; (b) does not specifically bind to rat CD27 and/or mouse CD27 as measured by SPR or flow cytometry; (c) does not specifically bind to one or more TNF receptor superfamily members selected from the group consisting of CD30, HVEM, DR5, 4-1BB, CD40, OX40, GITR, and any combination thereof; (d) does not specifically bind to one or more human tissues at concentrations up to 10 μg/mL, wherein the human tissues are selected from the group consisting of thyroid, lung, skin, uterus, prostate, liver, kidney, pancreas, adrenal, pituitary, placenta, testis, cerebrum, cerebellum, heart, peripheral nerve, and any combination thereof; (e) is capable of inducing NF-κB and MAPK signaling in naïve and pre-activated human T cells stimulated by an anti-CD3 Ab and an anti-CD28 Ab; (f) is capable of inducing proliferation and/or IFN-γ secretion in a CHO-svCD3-CD32A assay; (g) is capable of inducing proliferation of CD4+CD45RO+ memory T cells; (h) is capable of increasing IL-2 release from *staphylococcus* enterotoxin B (SEB)-stimulated human PBMCs; (i) is capable of increasing IL-2 release at least two-fold when combined with an anti-Programmed Death-1 (anti-PD-1) Ab; (j) is capable of reversing Treg-mediated suppression of co-cultured CD4+ responder T cells in the presence of monocyte-derived dendritic cells (MDDC) and soluble OKT3; and (k) is capable of potentiating the proliferation of human T cells and induction of IFN-γ secretion by soluble CD70.

In certain embodiments, any of the anti-CD27 mAbs or antigen-binding portions thereof binds to hCD27 with a $K_D$ of about 100 nM or lower, about 90 nM or lower, about 80 nM or lower, about 70 nM or lower, about 60 nM or lower, about 50 nM or lower, about 40 nM or lower, between about 1 nM and about 100 nM, between about 10 nM and about 70 nM, between about 10 nM and about 50 nM, or between about 40 nM and about 45 nM.

In certain embodiments, any of the anti-CD27 mAbs or antigen-binding portions thereof binds to human T cells with an $EC_{50}$ of about 0.1 nM or lower, about 0.09 nM or lower, about 0.08 nM or lower, about 0.07 nM or lower, about 0.06 nM or lower, about 0.05 nM or lower, about 0.04 nM or lower, between about 0.01 nM and about 0.1 nM, between about 0.025 nM and about 0.075 nM, or between about 0.03 nM and about 0.06 nM.

In certain embodiments, any of the anti-CD27 mAbs or antigen-binding portions thereof binds to cynomolgus T cells with $EC_{50}$ of about 0.5 nM or lower, about 0.4 nM or lower, about 0.3 nM or lower, about 0.2 nM or lower, about 0.1 nM or lower, between about 0.01 nM and about 0.5 nM, between about 0.025 nM and about 0.4 nM, between about 0.04 and about 0.3 nM, or between about 0.06 nM and about 0.2 nM.

In certain embodiments, any of the anti-CD27 mAbs or antigen-binding portions thereof comprise a heavy chain constant region which is of a human IgG1, IgG2, IgG3, or IgG4 isotype. In certain preferred embodiments, the anti-CD27 mAb or antigen-binding portion thereof comprise a heavy chain constant region which is of a human IgG1 isotype. In other embodiments, the anti-CD27 mAb or antigen-binding portion thereof comprise a heavy chain constant region which is of a human IgG4 isotype.

In certain embodiments, any of the anti-CD27 mAbs is a full-length Ab of an IgG1, IgG2, IgG3, or IgG4 isotype.

In certain embodiments, any of the anti-CD27 antigen-binding portions is an Ab fragment or a single chain Ab. In certain embodiments, the Ab fragment is selected from the group consisting of a Fab, F(ab')$_2$, Fd and Fv fragment, a single-domain Ab, a single-chain variable fragment (scFv), a divalent scFv (di-scFv) and bivalent scFv (bi-scFv), a diabody, a minibody, a CDR, and any combination thereof.

In certain embodiments, any of the anti-CD27 mAbs or antigen-binding portions thereof is a human Ab or a fragment thereof.

In certain embodiments, any of the anti-CD27 mAbs or antigen-binding portions thereof is a humanized Ab or a fragment thereof.

In certain embodiments, any of the anti-CD27 mAbs or antigen-binding portions thereof is a chimeric Ab or a fragment thereof.

In certain embodiments, any of the anti-CD27 mAbs or antigen-binding portions thereof is a hCD27 agonist.

In certain embodiments, any of the anti-CD27 mAbs or antigen-binding portions thereof does not inhibit CD70 binding to CD27 as measured by SPR or flow cytometry.

In certain embodiments, any of the anti-CD27 mAbs or antigen-binding portions thereof does not specifically bind to rat CD27 and/or mouse CD27 as measured by SPR or flow cytometry.

In certain embodiments, any of the anti-CD27 mAbs or antigen-binding portions thereof does not specifically bind to one or more TNF receptor superfamily members selected from the group consisting of CD30, HVEM, DR5, 4-1BB, CD40, OX40, GITR, and any combination thereof.

In certain embodiments, any of the anti-CD27 mAbs or antigen-binding portions thereof does not specifically bind to one or more human tissues at concentrations up to 10 µg/mL, wherein the human tissues are selected from the group consisting of thyroid, lung, skin, uterus, prostate, liver, kidney, pancreas, adrenal, pituitary, placenta, testis, cerebrum, cerebellum, heart, peripheral nerve, and any combination thereof.

In certain embodiments, any of the anti-CD27 mAbs or antigen-binding portions thereof is capable of inducing NF-κB and MAPK signaling in naïve and pre-activated human T cells stimulated by an anti-CD3 Ab and an anti-CD28 Ab. In certain embodiments, the mAb or antigen-binding portion thereof is capable of inducing NF-κB and MAPK signaling with an $EC_{50}$ of about 0.5 nM or lower, about 0.4 nM or lower, about 0.3 nM or lower, between about 0.005 nM and about 0.5 nM, between about 0.01 nM and about 0.4 nM, or between about 0.02 nM and about 0.25 nM.

In certain embodiments, any of the anti-CD27 mAbs or antigen-binding portions thereof is capable of inducing proliferation and/or IFN-γ secretion in a CHO-svCD3-CD32A assay. In certain embodiments, the mAb or antigen-binding portion thereof is capable of inducing proliferation and/or IFN-γ secretion with an $EC_{50}$ of about 0.05 nM or lower, about 0.04 nM or lower, about 0.03 nM or lower, between about 0.0005 nM and about 0.05 nM, between about 0.0005 nM and about 0.04 nM, between about 0.0005 nM and about 0.03 nM, between about 0.001 nM and about 0.05 nM, between about 0.001 nM and about 0.04 nM, or between about 0.001 nM and about 0.03 nM.

In certain embodiments, any of the anti-CD27 mAbs or antigen-binding portions thereof is capable of inducing proliferation of CD4+CD45RO+ memory T cells. In certain embodiments, the mAb or antigen-binding portion thereof is capable of inducing proliferation with an $EC_{50}$ of about 0.01 nM or less, about 0.009 nM or less, about 0.008 nM or less, about 0.007 nM or less, about 0.006 nM or less, about 0.005 nM or less, between about 0.001 nM to about 0.01 nM, between about 0.002 nM to about 0.008 nM, between about 0.003 nM to about 0.007 nM, or between about 0.004 nM to about 0.006 nM.

In certain embodiments, any of the anti-CD27 mAbs or antigen-binding portions thereof is capable of increasing IL-2 release from SEB-stimulated human PBMCs. In certain embodiments, the mAb or antigen-binding portion thereof is capable of increasing IL-2 release by greater than about 50% in the presence of a cross-linker, for example, as compared to a negative control IgG1 mAb.

In certain embodiments, any of the anti-CD27 mAbs or antigen-binding portions thereof is capable of increasing IL-2 release at least about two-fold when combined with an anti-PD-1 Ab.

In certain embodiments, any of the anti-CD27 mAbs or antigen-binding portions thereof is capable of reversing Treg-mediated suppression of co-cultured CD4+ responder T cells in the presence of MDDC and soluble OKT3. In certain embodiments, the mAb or antigen-binding portion thereof is capable of reversing Treg-mediated suppression by at least about 70%, for example, as compared to a negative control IgG1 mAb.

In certain embodiments, any of the anti-CD27 mAbs or antigen-binding portions thereof is capable of potentiating the proliferation of human T cells and induction of IFN-γ secretion by soluble CD70. In certain embodiments, the mAb or antigen-binding portion thereof is capable of potentiating the proliferation with an $EC_{50}$ of about 0.01 nM or lower, about 0.009 nM or lower, about 0.008 nM or lower, about 0.007 nM or lower, about 0.006 nM or lower, about 0.005 nM or lower, between about 0.001 nM and about 0.01 nM, between about 0.002 nM and about 0.008 nM, or between about 0.003 nM and about 0.005 nM. In certain embodiments, the mAb or antigen-binding portion thereof is capable of potentiating the induction of IFN-γ secretion with an $EC_{50}$ of about 0.01 nM or lower, about 0.009 nM or lower, about 0.008 nM or lower, about 0.007 nM or lower, between about 0.001 nM and about 0.01 nM, between about 0.002 nM and about 0.008 nM, or between about 0.005 nM and about 0.007 nM.

The present invention relates to an immunoconjugate comprising any of the anti-CD27 mAbs or antigen-binding portions thereof linked to a therapeutic agent. In certain embodiments, the therapeutic agent is a cytotoxin. In certain other embodiments, the therapeutic agent is a radioactive isotope.

The present invention relates to a bispecific molecule comprising any of the anti-CD27 mAbs or antigen-binding portions thereof linked to a binding domain that has a different binding specificity than the anti-CD27 mAb or antigen binding portion thereof.

The present invention relates to a composition comprising: (a) any of the anti-CD27 mAbs or antigen-binding portions thereof; (b) any of the immunoconjugates; or (c) any of the bispecific molecules; and a pharmaceutically acceptable carrier. In certain embodiments, the composition further comprises an additional Ab or an antigen-binding portion thereof. In certain embodiments, the additional Ab or antigen-binding portion thereof is selected from the group consisting of an anti-PD-1 Ab, anti-Programmed Death Ligand-1 (PD-L1) Ab, anti-Cytotoxic T-Lymphocyte Antigen-4 (CTLA-4) Ab, anti-Lymphocyte Activation Gene-3 (LAG-3) Ab, anti-B and T lymphocyte attenuator (BTLA) Ab, anti-T cell Immunoglobulin and Mucin domain-3 (TIM-3) Ab, anti-Killer Immunoglobulin-like Receptor (KIR) Ab, anti-Killer cell Lectin-like Receptor G1 (KLRG-1) Ab, anti-adenosine A2a receptor (A2aR) Ab, anti-Natural Killer Cell Receptor 2B4 (CD244) Ab, anti-CD160 Ab, T cell Immunoreceptor with Ig and ITIM domains (TIGIT) Ab, V-domain Ig Suppressor of T cell Activation (VISTA) Ab, nivolumab, pembrolizumab, and any combination thereof. In certain embodiments, the additional Ab or antigen-binding portion thereof is selected from the group consisting of an anti-Inducible T cell Co-Stimulator (ICOS) Ab, anti-CD137 (4-1BB) Ab, anti-CD134 (OX40) Ab, anti-Glucocorticoid-Induced TNFR-Related protein (GITR) Ab, anti-Herpes Virus Entry Mediator (HVEM) Ab, and any combination thereof.

The present invention relates to an isolated nucleic acid encoding any of the anti-CD27 mAbs or antigen-binding portions thereof.

The present invention relates to an expression vector comprising any of the isolated nucleic acids.

The present invention relates to a host cell comprising any of the expression vectors.

The present invention relates to a transgenic mouse comprising human immunoglobulin heavy and light chain transgenes, wherein the mouse expresses any of the anti-CD27 mAbs.

The present invention relates to a hybridoma prepared from any of the transgenic mice, wherein the hybridoma produces the anti-CD27 mAb.

The present invention relates to a method for preparing any of the anti-CD27 mAbs or antigen-binding portions thereof, which comprises expressing the anti-CD27 mAb or antigen-binding portion thereof in any of the host cells and isolating the anti-CD27 mAb or antigen-binding portion thereof from the host cell.

The present invention relates to a method for treating a subject afflicted with a cancer, comprising administering to the subject a therapeutically effective amount of any of the anti-CD27 mAbs or antigen-binding portions thereof, any of the immunoconjugates, any of the bispecific molecules, or any of the pharmaceutical compositions, such that the subject is treated.

The present invention relates to a method for inhibiting growth of tumor cells in a subject, comprising administering to the subject a therapeutically effective amount of any of the anti-CD27 mAbs or antigen-binding portions thereof, any of the immunoconjugates, any of the bispecific molecules, or any of the pharmaceutical compositions, such that growth of tumor cells in the subject is inhibited.

In certain embodiments, any of the methods for treating cancer or inhibiting tumor growth further comprises administering to the subject a therapeutically effective amount of an additional therapeutic agent for treating cancer. In certain embodiments, the additional therapeutic agent is a compound that reduces inhibition, or increases stimulation, of the immune system. In certain embodiments, the additional therapeutic agent is a small-molecule compound, a macrocyclic peptide, a fusion protein, or an Ab. In certain embodiments, the additional therapeutic agent is an antagonistic Ab or antigen-binding portion thereof that binds specifically to PD-1, PD-L1, CTLA-4, LAG-3, BTLA, TIM-3, KIR, KLRG-1, A2aR, CD244, CD160, TIGIT, or VISTA. In certain embodiments, the additional therapeutic agent is an agonistic Ab or antigen-binding portion thereof that binds specifically to ICOS, CD137 (4-1BB), CD134 (OX40), CD27, GITR, or HVEM. In certain embodiments, the additional therapeutic agent is an antagonistic Ab or antigen-binding portion thereof that binds specifically to PD-1 or to PD-L1, disrupts the interaction between PD-1 and PD-L1, and inhibits PD-1/PD-L1 signaling. In certain embodiments, the additional therapeutic agent is an antagonistic Ab or antigen-binding portion thereof that binds specifically to PD-1 or to PD-L1 and is a chimeric, humanized, or human mAb or antigen-binding portion thereof. In certain embodiments, the additional therapeutic agent is an antagonistic Ab or antigen-binding portion thereof that binds specifically to PD-1 and cross-competes with nivolumab for binding to human PD-1. In certain embodiments, the additional therapeutic agent is an antagonistic Ab or antigen-binding portion thereof that binds specifically to PD-1 and is nivolumab, pembrolizumab or cemiplimab. In certain embodiments, the additional therapeutic agent is an antagonistic Ab or antigen-binding portion thereof that binds specifically to PD-L1 and cross-competes with the Ab designated BMS-936559 (WO 2013/173223) for binding to human PD-L1. In certain embodiments, the additional therapeutic agent is an antagonistic Ab or antigen-binding portion thereof that binds specifically to PD-L1 and is atezolizumab, durvalumab, avelumab, or the Ab designated BMS-936559 (WO 2013/173223).

In certain embodiments, the cancer in any of the methods disclosed herein for treating cancer or inhibiting tumor growth is a solid tumor or the tumor cells are cells of a solid tumor. In certain embodiments, the solid tumor is a colon cancer or a fibrosarcoma. In further embodiments, the solid tumor is a cancer selected from the group consisting of squamous cell carcinoma, small cell lung cancer (SCLC), non-small cell lung cancer (NSCLC), squamous NSCLC, non-squamous NSCLC, head and neck cancer, squamous cell carcinoma of the head and neck (SCCHN), breast cancer, triple negative breast cancer (TNBC), male breast cancer, cancer of the esophagus, stomach cancer, gastrointestinal cancer, cancer of the small intestine, liver cancer, hepatocellular carcinoma (HCC), pancreatic cancer (PAC), pancreatic ductal adenocarcinoma (PDAC), kidney cancer, renal cell carcinoma (RCC), bladder cancer, cancer of the urethra, cancer of the ureter, colorectal cancer (CRC), rectal cancer, colon carcinoma, cancer of the anal region, endometrial cancer, prostate cancer, metastatic castration-resistant prostate cancer (mCRPC), neuroblastoma, glioma, glioblastoma, glioblastoma multiforme (GBM), germ cell tumor, pediatric sarcoma, sinonasal natural killer, melanoma, skin cancer, bone cancer, cervical cancer, uterine (endometrial) cancer, carcinoma of the endometrium, uterine sarcoma, carcinoma of the fallopian tubes, ovarian cancer, carcinoma of the cervix, carcinoma of the vagina, carcinoma of the vulva, testicular cancer, cancer of the endocrine system, thyroid cancer, cancer of the parathyroid gland, cancer of the adrenal gland, sarcoma of soft tissue, cancer of the penis, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, solid tumors of childhood, environmentally-induced cancers, virus-related cancers, cancers of viral origin, advanced cancer, unresectable cancer, metastatic cancer, refractory cancer, recurrent cancer, and any combination thereof.

In certain embodiments, the cancer in any of the disclosed methods for treating cancer or inhibiting tumor growth is a hematological malignancy or the tumor cells are cells of a hematological malignancy. In certain embodiments, the hematological malignancy is a T cell lymphoma. In certain embodiments, the hematological malignancy is selected from acute lymphoblastic leukemia (ALL), acute myelogenous leukemia (AML), chronic lymphocytic leukemia (CLL), chronic myelogenous leukemia (CIVIL), Hodgkin's lymphoma (HL), non-Hodgkin's lymphomas (NHLs), multiple myeloma, smoldering myeloma, monoclonal gammopathy of undetermined significance (MGUS), advanced, metastatic, refractory and/or recurrent hematological malignancies, and any combinations of said hematological malignancies.

In certain embodiments, the subject in any of the methods for treating or inhibiting is a human being.

The present invention relates to a kit for treating a subject afflicted with a cancer, the kit comprising: (a) one or more dosages ranging from about 0.1 to about 20 mg/kg body weight of any of the anti-CD27 mAbs or antigen-binding portions thereof, any of the immunoconjugates, any of the bispecific molecules, or any of the pharmaceutical compositions; and (b) instructions for using the one or more dosages in any of the methods for treating cancer or inhibiting tumor growth.

The present invention relates to a kit for treating a subject afflicted with a cancer, the kit comprising: (a) one or more dosages ranging from about 0.1 to about 20 mg/kg body weight of any of the anti-CD27 mAbs or antigen-binding portions thereof, any of the immunoconjugates, any of the bispecific molecules, or any of the pharmaceutical compositions; (b) one or more dosages ranging from about 200 to about 1600 mg of any of the Abs or antigen-binding portions thereof that bind specifically to PD-1 or to PD-L1; and (c) instructions for using the one or more dosages in any of the methods for treating or inhibiting that comprise an additional therapeutic agent, wherein the additional therapeutic agent is an antagonistic Ab or antigen-binding portion thereof that binds specifically to PD-1 or to PD-L1.

Other features and advantages of the instant invention will be apparent from the following detailed description and examples which should not be construed as limiting. The contents of all cited references, including scientific articles, GenBank entries, patents and patent applications cited throughout this application are expressly incorporated herein by reference.

BRIEF DESCRIPTION OF THE FIGURES

FIGS. 13(B) and (C) show that BMS-986215, but not 1F5, demonstrated weak agonist activity by enhancing T cell proliferation (B) and IFN-γ secretion in the absence of FcγR and without shCD70. FIGS. 13(D) and (E) show that BMS-986215, but not 1F5, potentiated activation of human T cells (proliferation and IFN-γ secretion) by soluble CD70 protein.

FIG. 14(D), anti-mPD-1: 27% TGI, 2/10 TF).

DETAILED DESCRIPTION OF THE INVENTION

Figure 1A:
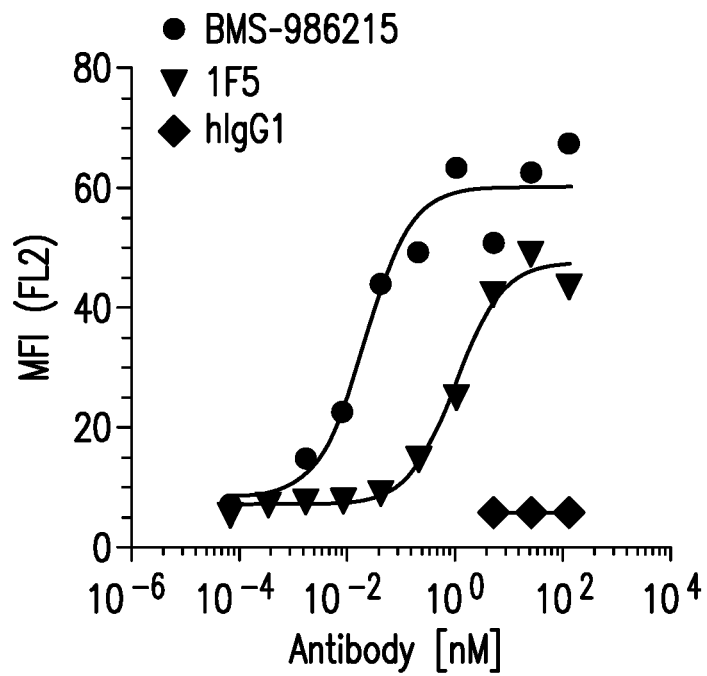
FIGS. 1(A)-(B) show binding affinities of Abs to human (A) and cynomolgus (B) T cells in flow cytometry analyses. Graphs show mean fluorescence intensity (MFI) associated with nanomolar (nM) concentrations of BMS-986215 and 1F5 human anti-CD27 mAbs, along with a human IgG1 (hIgG1) control Ab in (A). "FL2" in (A) indicates measurement in fluorescence channel 2 (FL2). The graphs show that BMS-986215 has a higher affinity for human and cynomolgus CD27 than 1F5.

The present invention relates to mAbs that bind specifically CD27 and to methods for treating cancers in a patient comprising administering to the patient an anti-CD27 Ab alone or in combination with an anticancer agent such as an immune checkpoint inhibitor.

Terms

In order that the present disclosure may be more readily understood, certain terms are first defined. As used in this application, except as otherwise expressly provided herein, each of the following terms shall have the meaning set forth below. Additional definitions are set forth throughout the application.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a therapeutic agent or a composition comprising a therapeutic agent to a subject, using any of the various methods and delivery systems known to those skilled in the art. A preferred route for administration of therapeutic Abs such as anti-CD27 Abs and anti-PD-1 Abs is intravenous administration. Other routes of administration include intramuscular, subcutaneous, intraperitoneal, or other parenteral routes of administration, for example by injection or infusion. The phrase "parenteral administration" as used herein means modes of administration other than enteral and topical administration. Administering can also be performed, for example, once, a plurality of times, and/or over one or more extended periods.

An "antibody" (Ab) shall include, without limitation, a glycoprotein immunoglobulin (Ig) which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region of an IgG Ab comprises three constant domains, $C_{H1}$, $C_{H2}$ and $C_{H3}$. Each light chain comprises a light chain variable region (abbreviated herein as $V_L$) and a light chain constant region. The light chain constant region of an IgG Ab comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1-CDR1-FR2-CDR2-FR3-CDR3-FR4. The variable regions of the heavy and light chains contain a binding domain that interacts with an antigen. A variety of methods have been used to delineate the CDR domains within an Ab, including the Kabat, Chothia, AbM, contact, and IMGT definitions. The constant regions of the Abs may mediate the binding of the Ig to host tissues or factors, including various cells of the immune system (e.g., effector cells) and the first component (C1q) of the classical complement system.

An Ig may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM, IgG1, or IgG4) that is encoded by the heavy chain constant region genes. The term "antibody" includes, by way of example, both naturally occurring and non-naturally occurring Abs, monoclonal and polyclonal Abs, chimeric and humanized Abs, human or nonhuman Abs, wholly synthetic Abs, and single chain Abs. A nonhuman Ab may be humanized partially or fully by recombinant methods to reduce its immunogenicity in man. Where not expressly stated, and unless the context indicates otherwise, the term "antibody" also includes an antigen-binding fragment or an antigen-binding portion of any of the aforementioned Ig's, and includes a monovalent and a divalent fragment or portion, and a single chain Ab.

An "isolated" Ab refers to an Ab that is substantially free of other Abs having different antigenic specificities (e.g., an isolated Ab that binds specifically to CD27 is substantially free of Abs that bind specifically to antigens other than CD27). An isolated Ab that binds specifically to hCD27 may, however, have cross-reactivity to other antigens, such as CD27 polypeptides from different species such as cynomolgus monkey. Moreover, an isolated Ab may be purified so as to be substantially free of other cellular material and/or chemicals.

The term "monoclonal" Ab (mAb) refers to a non-naturally occurring preparation of Ab molecules of single molecular composition, i.e., Ab molecules whose primary sequences are essentially identical and which exhibit a single binding specificity and affinity for a particular epitope. A mAb is an example of an isolated Ab. MAbs may be produced by hybridoma, recombinant, transgenic or other techniques known to those skilled in the art.

A "chimeric" Ab refers to an Ab in which the variable regions are derived from one species and the constant regions are derived from another species, such as an Ab in which the variable regions are derived from a mouse Ab and the constant regions are derived from a human Ab.

A "human" mAb (HuMAb) refers to a mAb having variable regions in which both the framework and CDR regions are derived from human germline immunoglobulin sequences. Furthermore, if the Ab contains a constant region, the constant region also is derived from human germline immunoglobulin sequences. The human Abs of the invention may include amino acid residues not encoded by human germline immunoglobulin sequences (e.g., mutations introduced by random or site-specific mutagenesis in vitro or by somatic mutation in vivo). However, the term "human" Ab, as used herein, is not intended to include Abs in which CDR sequences derived from the germline of another mammalian species, such as a mouse, have been grafted onto human framework sequences. The terms "human" Abs and "fully human" Abs are used synonymously.

A "humanized" mAb refers to a mAb in which some, most or all of the amino acids outside the CDR domains of a non-human mAb are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

An "anti-antigen" Ab refers to an Ab that binds specifically to an antigen. For example, an anti-CD27 Ab is an Ab that binds specifically to CD27, whereas an anti-PD-1 Ab is an Ab that binds specifically to PD-1. As used herein, an "anti-PD-1/anti-PD-L1" Ab is an Ab that is used to disrupt the PD-1/PD-L1 signaling pathway, which may be an anti-PD-1 Ab or an anti-PD-L1 Ab.

An "antigen-binding portion" of an Ab (also called an "antigen-binding fragment") refers to one or more fragments of an Ab that retain the ability to bind specifically to the antigen bound by the whole Ab.

A "cancer" refers a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream.

"CD27" refers to a receptor that is a member of the tumor necrosis factor receptor superfamily. CD27 is required for generation and long-term maintenance of T cell immunity, and binds to CD70. CD27 is constitutively expressed on the majority of mature T cells, memory B cells, and a portion of natural killer cells. The interaction of CD27 with its ligand CD70 plays key roles in the following processes: 1) costimulation through CD27 on T cells causes activation, proliferation, survival, and maturation of effector capacity and memory; 2) costimulation through CD27 on human B cells activates and promotes the generation of plasma cells, proliferation, and the production of immunoglobulin and 3) costimulation through CD27 on natural killer cells induces cytolytic activity. The term "CD27" as used herein includes hCD27, variants, isoforms, and species homologs of hCD27, and analogs having at least one common epitope with hCD27. The complete hCD27 sequence can be found under GenBank Accession No. AAH12160. The expression of CD27 on various types of lymphomas and leukemias such as chronic lymphocytic leukemia, mantle cell lymphoma, primary central nervous system lymphoma, Burkitt's lymphoma, and marginal zone b cell lymphoma has been well documented.

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, including the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"Programmed Death-1" (PD-1) refers to an immunoinhibitory receptor belonging to the CD28 family that is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 amino acid sequence can be found under GENBANK® Accession No. U64863.

"Programmed Death Ligand-1" (PD-L1) is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GENBANK® Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In preferred embodiments, the subject is a human. The terms "subject" and "patient" are used interchangeably herein.

A "therapeutically effective amount" or "therapeutically effective dosage" of a drug or therapeutic agent is any amount of the drug or agent that, when used alone or in combination with another therapeutic agent, protects a subject against the onset of a disease or promotes disease regression evidenced by a decrease in severity of disease symptoms, an increase in frequency and duration of disease symptom-free periods, or a prevention or reduction of impairment or disability due to the disease affliction. In addition, the terms "effective" and "effectiveness" with regard to a treatment includes both pharmacological effectiveness and physiological safety. Pharmacological effectiveness refers to the ability of the drug to promote disease regression, e.g., cancer regression, in the patient. Physiological safety refers to an acceptable level of toxicity, or other adverse physiological effects at the cellular, organ and/or organism level (adverse effects) resulting from administration of the drug. The efficacy of a therapeutic agent can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount of an anti-cancer agent preferably inhibits cell growth or tumor growth by at least about 20%, preferably by at least about 40%, more preferably by at least about 60%, even more preferably by at least about 80%, and still more preferably by about 100% relative to untreated subjects. In preferred embodiments of the invention, tumor regression may be observed and continue for a period of at least about 30 days, more preferably at least about 60 days, or even more preferably at least about 6 months. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an another therapeutic agent to a subject at risk of developing a disease (e.g., a subject having a pre-malignant condition who is at risk of developing a cancer) or of suffering a recurrence of the disease, inhibits the development or recurrence of the disease (e.g., a cancer). In preferred embodiments, the prophylactically effective amount prevents the development or recurrence of the disease entirely. "Inhibiting" the development or recurrence of a disease means either lessening the likelihood of the disease's development or recurrence, or preventing the development or recurrence of the disease entirely.

The use of the alternative (e.g., "or") should be understood to mean either one, both, or any combination thereof of the alternatives. As used herein, the indefinite articles "a" or "an" should be understood to refer to "one or more" of any recited or enumerated component.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" refers to a numeric value, composition or characteristic that is within an acceptable error range for the particular value, composition or characteristic as determined by one of ordinary skill in the art, which will depend in part on how the value, composition or characteristic is measured or determined, i.e., the limitations of the measurement system. For example, "about" can mean within 1 or within more than 1 standard deviation per the practice in the art. Alternatively, it can mean a range of plus or minus 20%, more usually a range of plus or minus 10%. When particular values, compositions or characteristics are provided in the application and claims, unless otherwise stated, the meaning of "about" should be assumed to be within an acceptable error range for that particular value, composition or characteristic. For dosing frequencies in drug administration regimens, the terms "once about every week," "once about every two weeks," or any other similar dosing interval terms as used herein mean approximate numbers. For example, "once about every week" can include every 7 days±one day, i.e., every 6 days to every 8 days. "Once about every 2 weeks" can include every 14 days±3 days, i.e., every 11 days to every 17 days. Similar approximations apply, for example, to once about every 3 weeks, once about every 4 weeks, once about every month, or once about every 3-6 months or longer.

The term "substantially the same" or "essentially the same" refers to a sufficiently high degree of similarity between two or more numeric values, compositions or characteristics that one of skill in the art would consider the difference between these values, compositions or characteristics to be of little or no biological and/or statistical significance within the context of the property being measured. The difference between numeric values being measured may, for example, be less than about 30%, preferably less than about 20%, and more preferably less than about 10%.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Anti-CD27 mAbs

In certain aspects, the present disclosure relates to isolated Abs, particularly mAbs or antigen-binding portions thereof, that specifically bind to hCD27. In certain embodiments, the sequence of hCD27 is set forth as SEQ ID NO: 1.

Specific Binding of Anti-CD27 Abs to CD27

The anti-CD27 Abs, including mAbs or antigen-binding portions thereof, of this invention specifically bind to CD27. Abs typically specifically bind to their cognate antigen with high affinity, reflected by a dissociation constant ($K_D$) of 1 μM to 10 pM or lower. Any $K_D$ greater than about 100 μM is generally considered to indicate nonspecific binding. As used herein, an IgG Ab that "specifically binds" to an antigen refers to an Ab that binds to the antigen and substantially identical antigens with high affinity, which means having a $K_D$ of about 100 nM or lower, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. In some embodiments, an Ab that specifically binds to hCD27 also has cross-reactivity with CD27 antigens from certain primate species, e.g., cynomolgus monkey. In some embodiments, an Ab that specifically binds to hCD27 does not cross-react with CD27 antigens from rodent species, e.g. mouse and/or rat, or with an antigen other than CD27, e.g., an Axl or PD-1 antigen.

The term "$K_D$," as used herein, is intended to refer to the dissociation constant for a particular Ab-antigen interaction, which is obtained from the ratio of $k_{off}$ to $k_{on}$ (i.e., $k_{off}/k_{on}$) and is expressed as a molar concentration (e.g., nM). The term "$k_{on}$" refer to the association rate or "on rate" for the association of an Ab and its antigen interaction, whereas the term "$k_{off}$" refers to the dissociation rate for the Ab-antigen complex. $K_D$ values for Abs can be determined using methods well established in the art, such as surface plasmon resonance (SPR) or bio-layer interferometry (BLI; ForteBio, Fremont, CA). $K_D$ values determined by different methods for a single Ab can vary considerably, for example, up to a 1,000-fold. Thus, in comparing the $K_D$ values for different Abs, it is important that these $K_D$ values be determined using the same method. Where not explicitly stated, and unless the context indicates otherwise, $K_D$ values for Ab binding disclosed herein were determined by SPR using a BIACORE® biosensor system (GE Healthcare, Chicago, IL).

In certain embodiments of the disclosed invention, the anti-CD27 mAb or antigen-binding portion thereof binds to hCD27 with a $K_D$ of: about 100 nM or lower, about 95 nM or lower, about 90 nM or lower, about 85 nM or lower, about 80 nM or lower, about 75 nM or lower, about 70 nM or lower, about 65 nM or lower, about 60 nM or lower, about 55 nM or lower, about 50 nM or lower, about 45 nM or lower, about 40 nM or lower, between about 1 nM and about 100 nM, between about 1 nM and about 70 nM, between about 1 nM and about 50 nM, between about 1 nM and about 45 nM, between about 5 nM and about 100 nM, between about 5 nM and about 70 nM, between about 5 nM and about 50 nM, between about 5 nM and about 45 nM, between about 10 nM and about 100 nM, between about 10 nM and about 70 nM, between about 10 nM and about 50 nM, between about 10 nM and about 45 nM, or between about 40 nM and about 45 nM. In certain embodiments, the anti-CD27 mAb or antigen-binding portion thereof binds to hCD27 with a $K_D$ of: about 100 nM or lower, about 90 nM or lower, about 80 nM or lower, about 70 nM or lower, about 60 nM or lower, about 50 nM or lower, about 40 nM or lower, between about 1 nM and about 100 nM, between about 10 nM and about 70 nM, between about 10 nM and about 50 nM, or between about 40 nM and about 45 nM. In certain embodiments, the $K_D$ is at about 37° C. and/or about 25° C. In certain embodiments, the anti-CD27 mAb or antigen-binding portion thereof binds to hCD27 with a $K_D$ of: between about 10 nM and about 100 nM, between about 10 nM and about 75 nM, between about 10 nM and about 50 nM, or between about 10 nM and about 45 nM at about 37° C. and at about 25° C. In certain embodiments, the anti-CD27 mAb or antigen-binding portion thereof binds to hCD27 with a $K_D$ of: between about 15 nM and about 100 nM, between about 15 nM and about 75 nM, between about 15 nM and about 50 nM, between about 15 nM and about 45 nM, between about 20 nM and about 100 nM, between about 20 nM and about 75 nM, between about 20 nM and about 50 nM, between about 20 nM and about 45 nM, between about 30 nM and about 100 nM, between about 30 nM and about 75 nM, between about 30 nM and about 50 nM, between about 30 nM and about 45 nM, or between about 40 nM and about 45 nM at about 37° C. In certain embodiments, the anti-CD27 mAb or antigen-binding portion thereof binds to hCD27 with a $K_D$ of: about 45 nM or lower, about 40 nM or lower, about 35 nM or lower, about 30 nM or lower, about 25 nM or lower, about 20 nM or lower, between about 1 nM and about 45 nM, between about 1 nM and about 40 nM, between about 1 nM and about 30 nM, between about 1 nM and about 20 nM, between about 5 nM and about 45 nM, between about 5 nM and about 40 nM, between about 5 nM and about 30 nM, between about 5 nM and about 20 nM, between about 10 nM and about 45 nM, between about 10 nM and about 40 nM, between about 10 nM and about 30 nM, or between about 10 nM and about 20 nM at about 25° C. In some embodiments, the anti-CD27 mAb or antigen-binding portion thereof binds to hCD27 with a $K_D$ of: between about 41 nM and about 44 nM at about 37° C. and/or between about 13 nM and about 16 nM at about 25° C.

Binding of Anti-CD27 Abs to Specific Epitopes

Various methods, including hydrogen/deuterium exchange mass spectrometry (HDX-MS) and fast photochemical oxidation of proteins (FPOP), can be utilized to probe binding epitopes of Abs.

HDX-MS probes protein conformation and conformational dynamics in solution by monitoring the rate and extent of deuterium exchange of backbone amide hydrogen atoms (Huang and Chen, 2015; Wei et al., 2014). The level of HDX depends on the solvent accessibility of backbone amide hydrogen atoms and the protein hydrogen bonds. The mass increase of the protein upon HDX can be precisely measured by MS. When this technique is paired with enzymatic digestion, structural features at the peptide level can be resolved, enabling differentiation of surface-exposed peptides from those folded inside. Typically, the deuterium labeling and subsequent quenching experiments are performed, followed by enzymatic digestion, peptide separation, and MS analysis.

FPOP is a complementary protein footprinting technique for the characterization of protein conformation by detecting oxidation levels of amino acid side-chains, typically induced by hydroxyl (OH) radicals (Yan et al., 2014; Jones et al., 2011). The extent of side-chain oxidation depends on solvent accessibility of amino acids side chains and chemical properties of exposed amino acids. FPOP uses laser irradiation of $H_2O_2$ for the photochemical labeling with a flow system and controls the radical lifetime to ~1 μs by introducing a radical scavenger to prevent excessive labeling. The oxidized proteins are subsequently digested by enzyme and analyzed by MS. The changes in peptide oxidation levels under different conditions can be used to obtain local conformational changes and characterize protein interfaces.

In certain embodiments, an isolated Ab of the invention, including a mAb or antigen-binding portion thereof, specifically binds to an epitope located within discontinuous regions spanning approximately amino acid residues 21 to 41 and 52 to 57 of hCD27, a sequence of which is SEQ ID NO: 1, as determined by HDX-MS and/or FPOP epitope mapping.

Structurally Defined Anti-CD27 Abs

The present disclosure also provides an isolated Ab, preferably a mAb, or an antigen-binding portion thereof, which specifically binds to hCD27, and comprises the CDR1, CDR2 and CDR3 domains in each of: a $V_H$ comprising consecutively linked amino acids having the sequence set forth as SEQ ID NO: 8 and a $V_L$ comprising consecutively linked amino acids having the sequence set forth as SEQ ID NO: 9.

Different methods have been developed to delineate the CDR domains within an Ab. In addition to the widely used Kabat definition, others including the Chothia, AbNum, AbM, contact and IMGT definitions that seek to address deficiencies of the Kabat definitions, have been employed.

The approach of Kabat and co-workers (Wu and Kabat, 1970; Kabat et al., 1983), was based on the assumption that CDRs include the most variable positions in Abs and therefore could be identified by aligning the fairly limited number of Ab sequences then available. Based on this alignment, Kabat et al. introduced a numbering scheme for the residues in the hypervariable regions and determined which positions mark the beginning and the end of each CDR (bioinf.org.uk/abs/simkab.html).

The Chothia definition is based on the analysis of a small number of Ab structures to determine the relationship between the sequences of the Abs and the structural loop regions of their CDRs (Chothia et al., 1987; 1989; Al-Lazikani et al., 1997; bioinf.org.uk/abs/chothia.html). The boundaries of the FRs and the CDRs were determined and the latter have been shown to adopt a restricted set of conformations based on the presence of certain residues at key positions in the CDRs and the flanking FRs. The resulting Chothia numbering scheme is almost identical to the Kabat scheme, but based on structural considerations, places insertions in the $V_L$ CDR1 and $V_H$ CDR1 at different positions. As more experimental data became available, there has been an ongoing re-analysis and re-definition of the boundaries of the CDRs. Abhinandan and Martin (2008) analyzed Ab sequence alignments in the context of structure and found that approximately 10% of the sequences in the manually annotated Kabat database contain errors or inconsistencies. They proposed a corrected version of the Chothia scheme which is structurally correct throughout the CDRs and frameworks, and developed a software tool (AbNum; available at www.bioinf.org.uk/abs/abnum/) that applies the Kabat, Chothia and modified-Chothia numbering in an automatic and reliable manner. Another method, the AbM definition, represents a compromise between the Kabat and Chothia definitions and is used by Oxford Molecular Group's AbM Ab modeling software (www.bioinf.org.uk/abs; Martin et al., 1989).

The contact definition is based on an analysis of the contacts between Ab and antigen in the complex crystal structures available in the Protein Data Bank (bioinf.org.uk/abs/; MacCallum et al., 1996).

A more recent attempt to define CDRs is that of the IMGT database (Lefranc et al. (2003; www.imgt.org) which curates nucleotide sequence information for Ig's, T-cell receptors (TcR) and Major Histocompatibility Complex (MHC) molecules. It proposes a uniform numbering system for Ig and TcR sequences, based on aligning more than 5000 Ig and TcR variable region sequences.

The Kabat definition is the most commonly used method to predict CDR domains, notwithstanding it was developed when no structural information on Abs was available. Where not explicitly stated, and unless the context indicates otherwise, CDRs disclosed herein have been identified using the Kabat definition (see Table 2). Accordingly, the disclosure provides isolated Abs, preferably mAbs, or antigen-binding portions thereof that specifically binds to hCD27, comprising sets of six CDRs, at least one of which corresponds to a CDR sequence shown in Table 2. In certain embodiments, the disclosure provides an isolated Ab, preferably a mAb, or an antigen-binding portion thereof that specifically binds to hCD27, comprising all three heavy chain variable region ($V_H$) CDR sequences shown in Table 2. In certain embodiments, the disclosure provides an isolated Ab, preferably a mAb, or an antigen-binding portion thereof that specifically binds to hCD27, comprising all three light chain variable region ($V_L$) CDR sequences shown in Table 2.

In certain embodiments, the disclosure provides an isolated Ab, preferably a mAb, or an antigen-binding portion thereof that specifically binds to hCD27, comprising:

(a) a $V_H$ comprising a CDR1 comprising consecutively linked amino acids having the sequence set forth as SEQ ID NO: 2, a CDR2 comprising consecutively linked amino acids having the sequence set forth as SEQ ID NO: 3, and a CDR3 comprising consecutively linked amino acids having the sequence set forth as SEQ ID NO: 4; and (b) a $V_L$ comprising a CDR1 comprising consecutively linked amino acids having the sequence set forth as SEQ ID NO: 5, a CDR2 comprising consecutively linked amino acids having the sequence set forth as SEQ ID NO: 6, and a CDR3 comprising consecutively linked amino acids having the sequence set forth as SEQ ID NO: 7.

In certain embodiments, the $V_H$ comprises consecutively linked amino acids having the sequence set forth as SEQ ID NO: 8.

In certain embodiments, the $V_L$ comprises consecutively linked amino acids having the sequence set forth as SEQ ID NO: 9.

In certain embodiments, the Ab, preferably a mAb, comprises a heavy chain comprising consecutively linked amino acids having the sequence set forth as SEQ ID NO: 12 and a light chain comprising consecutively linked amino acids having the sequence set forth as SEQ ID NO: 13.

In certain embodiments, the Ab is the mAb designated BMS-986215.

Anti-CD27 Abs comprising $V_H$ and $V_L$ regions having amino acid sequences that are highly similar or homologous to the amino acid sequences of any of the above anti-CD27 Abs and which retain the functional properties of these Abs are also suitable for use in the present methods. For example, suitable Abs include mAbs comprising a $V_H$ and $V_L$ region each comprising consecutively linked amino acids having a sequence that is at least 80% identical to the amino acid sequence set forth in SEQ ID Nos. 8 and/or 9, respectively. In further embodiments, for example, the $V_H$ and/or $V_L$ amino acid sequences exhibits at least 85%, preferably at least 90%, more preferably at least 95%, or 99% identity to the sequences set forth in SEQ ID Nos. 8 and/or 9, respectively. As used herein, the percent sequence identity between two amino acid sequences is a function of the number of identical positions shared by the sequences relative to the length of the sequences compared (i.e., % identity=number of identical positions/total number of positions being compared×100), taking into account the number of any gaps, and the length of each such gap, introduced to maximize the degree of sequence identity between the two sequences. The comparison of sequences and determination of percent identity between two sequences can be accomplished using mathematical algorithms that are well known to those of ordinary skill in the art.

In certain embodiments, the isolated anti-CD27 Ab or antigen-binding portion thereof comprises a heavy chain constant region which is of a human IgG1, IgG2, IgG3 or IgG4 isotype. In certain preferred embodiments, the isolated anti-CD27 Ab or antigen-binding portion thereof is of a human IgG1 isotype. In other embodiments, the isolated anti-CD27 Ab or antigen-binding portion thereof is of a human IgG4 isotype. In certain embodiments, the isolated anti-CD27 Ab is a full-length Ab of an IgG1, IgG2, IgG3 or IgG4 isotype. In certain preferred embodiments, the full-length Ab is of an IgG1 isotype. In further embodiments, the full-length Ab is of an IgG4 isotype.

Anti-CD27 mAbs that Cross-Compete with a Reference Ab for Binding to CD27

Also encompassed within the scope of the disclosed invention is an isolated Ab, preferably a mAb, or an antigen-binding portion thereof, which specifically binds to CD27, e.g., hCD27 and/or cynomolgus CD27 (cCD27), and cross-competes with a reference Ab or a reference antigen-binding portion thereof for binding to hCD27. The ability of a pair of Abs to "cross-compete" for binding to an antigen, e.g., CD27, indicates that a first Ab binds to substantially the same epitope region of the antigen as, and sterically hinders the binding of, a second Ab to that particular epitope region and, conversely, the second Ab binds to substantially the same epitope region of the antigen as, and sterically hinders the binding of, the first Ab to that epitope region. Thus, the ability of a test Ab to competitively inhibit the binding of, for example, mAb BMS-986215 to hCD27, demonstrates that the test Ab binds to substantially the same epitope region of hCD27 as does mAb BMS-986215.

A first Ab is considered to bind to "substantially the same epitope" as does a second Ab if the first Ab reduces the binding of the second Ab to an antigen by at least about 40%. Preferably, the first Ab reduces the binding of the second Ab to the antigen by more than about 50% (e.g., at least about 60% or at least about 70%). In more preferred embodiments, the first Ab reduces the binding of the second Ab to the antigen by more than about 70% (e.g., at least about 80%, at least about 90%, or about 100%). The order of the first and second Abs can be reversed, i.e. the "second" Ab can be first bound to the surface and the "first" is thereafter brought into contact with the surface in the presence of the "second" Ab. The Abs are considered to "cross-compete" if a competitive reduction in binding to the antigen is observed irrespective of the order in which the Abs are added to the immobilized antigen.

Cross-competing Abs are expected to have functional properties very similar to the properties of the reference Abs by virtue of their binding to substantially the same epitope region of an antigen such as a CD27 receptor. The higher the degree of cross-competition, the more similar will the functional properties be. For example, two cross-competing Abs are expected to have essentially the same functional properties if they each inhibit binding of the other to an epitope by at least about 80%. This similarity in function is expected to be even closer if the cross-competing Abs exhibit similar affinities for binding to the epitope as measured by the dissociation constant ($K_D$).

Cross-competing anti-antigen Abs can be readily identified based on their ability to detectably compete in standard antigen binding assays, including BIACORE® analysis, ELISA assays or flow cytometry, using either recombinant antigen molecules or cell-surface expressed antigen molecules. By way of example, a simple competition assay to identify whether a test Ab competes with BMS-986215 for binding to hCD27 may involve: (1) measuring the binding of BMS-986215, applied at saturating concentration, to a BIACORE® chip (or other suitable medium for SPR analysis) onto which hCD27 is immobilized, and (2) measuring the binding of BMS-986215 to a hCD27-coated BIACORE® chip (or other medium suitable) to which the test Ab has been previously bound. The binding of BMS-986215 to the CD27-coated surface in the presence and absence of the test Ab is compared. A significant (e.g., more than about 40%) reduction in binding of BMS-986215 in the presence of the test Ab indicates that both Abs recognize substantially the same epitope such that they compete for binding to the CD27 target. The percentage by which the binding of a first Ab to an antigen is inhibited by a second Ab can be calculated as: [1−(detected binding of first Ab in presence of second Ab)/(detected binding of first Ab in absence of second Ab)]×100. To determine whether the Abs cross-compete, the competitive binding assay is repeated except that the binding of the test Ab to the CD27-coated chip in the presence of BMS-986215 is measured.

In some aspects, the present disclosure relates to isolated Abs, particularly mAbs or antigen-binding portions thereof, that specifically bind to the same epitope of hCD27 as any of the anti-CD27 Abs disclosed herein.

Characteristics of Anti-CD27 mAbs

In certain embodiments, an isolated Ab of the invention, including a mAb or antigen-binding portion thereof, has one or more characteristics as described herein.

In certain embodiments, an isolated Ab of the invention, including a mAb or antigen-binding portion thereof, is a hCD27 agonist.

In certain embodiments, an isolated Ab of the invention, including a mAb or antigen-binding portion thereof, specifically binds to CD27, e.g., hCD27, and does not block binding of its CD70 ligand as measured by surface plasmon resonance (SPR) or flow cytometry (i.e., does not inhibit CD70 binding to CD27 as measured by SPR or flow cytometry). Such mAbs or antigen-binding portions thereof can be interchangeably referred to herein as non-ligand blocking mAbs or antigen-binding portions thereof, ligand non-blocking mAbs or antigen-binding portions thereof, or ligand non-blockers.

In certain embodiments, an isolated Ab of the invention, including a mAb or antigen-binding portion thereof, does not specifically bind to rat CD27 and/or mouse CD27 as measured by SPR or flow cytometry.

In certain embodiments, an isolated Ab of the invention, including a mAb or antigen-binding portion thereof, does not specifically bind to one or more TNF receptor superfamily members selected from the group consisting of CD30, HVEM, DR5, 4-1BB, CD40, OX40, GITR, and any combination thereof.

In certain embodiments, an isolated Ab of the invention, including a mAb or antigen-binding portion thereof, does not specifically bind to one or more human tissues at concentrations up to 10 µg/mL, wherein the human tissues are selected from the group consisting of thyroid, lung, skin, uterus, prostate, liver, kidney, pancreas, adrenal, pituitary, placenta, testis, cerebrum, cerebellum, heart, peripheral nerve, and any combination thereof.

In certain embodiments, an isolated Ab of the invention, including a mAb or antigen-binding portion thereof, induces NF-κB and MAPK signaling in naïve and pre-activated human T cells stimulated by an anti-CD3 Ab and an anti-CD28 Ab. In certain embodiments, isolated Ab of the invention, including a mAb or antigen-binding portion thereof, induces NF-κB and/or MAPK signaling in naïve and pre-activated human T cells stimulated by an anti-CD3 Ab and an anti-CD28 Ab with an $EC_{50}$ of: about 0.5 nM or lower, about 0.45 nM or lower, about 0.4 nM or lower, about 0.35 nM or lower, about 0.3 nM or lower, about 0.25 nM or lower, about 0.2 nM or lower, between about 0.005 nM and about 0.5 nM, between about 0.005 nM and about 0.4 nM, between about 0.005 nM and about 0.3 nM, between about 0.005 nM and about 0.25 nM, between about 0.005 nM and about 0.2 nM, between about 0.01 nM and about 0.5 nM, between about 0.01 nM and about 0.4 nM, between about 0.01 nM and about 0.3 nM, between about 0.01 nM and about 0.25 nM, between about 0.01 nM and about 0.2 nM, between about 0.015 nM and about 0.5 nM, between about 0.015 nM and about 0.4 nM, between about 0.015 nM and about 0.3 nM, between about 0.015 nM and about 0.25 nM, between about 0.015 nM and about 0.2 nM, between about 0.02 nM and about 0.5 nM, between about 0.02 nM and about 0.4 nM, between about 0.02 nM and about 0.3 nM, between about 0.02 nM and about 0.25 nM, or between about 0.02 nM and about 0.23 nM. In certain embodiments, an isolated Ab of the invention, including a mAb or antigen-binding portion thereof, induces NF-κB and MAPK signaling with an $EC_{50}$ of: about 0.5 nM or lower, about 0.4 nM or lower, about 0.3 nM or lower, between about 0.005 nM and about 0.5 nM, between about 0.01 nM and about 0.4 nM, or between about 0.015 and about 0.3 nM.

In certain embodiments, an isolated Ab of the invention, including a mAb or antigen-binding portion thereof, induces proliferation and/or IFN-γ secretion in a CHO-svCD3-CD32A assay. In certain embodiments, an isolated Ab of the invention, including a mAb or antigen-binding portion thereof, induces proliferation and/or IFN-γ secretion in a CHO-svCD3-CD32A assay with an $EC_{50}$ of: about 0.05 nM or lower, about 0.045 nM or lower, about 0.04 nM or lower, about 0.035 nM or lower, about 0.03 nM or lower, about 0.025 nM or lower, about 0.02 nM or lower, about 0.015 nM or lower, about 0.01 nM or lower, about 0.009 nM or lower, about 0.008 nM or lower, between about 0.0005 nM and about 0.05 nM, between about 0.0005 nM and about 0.04 nM, between about 0.0005 nM and about 0.03 nM, between about 0.0005 nM and about 0.02 nM, between about 0.0005 nM and about 0.01 nM, between about 0.0005 nM and about 0.009 nM, between about 0.0005 nM and about 0.008 nM, between about 0.001 nM and about 0.05 nM, between about 0.001 nM and about 0.04 nM, between about 0.001 nM and about 0.03 nM, between about 0.001 nM and about 0.02 nM, between about 0.001 nM and about 0.01 nM, between about 0.001 nM and about 0.009 nM, or between about 0.001 nM and about 0.008 nM. In certain embodiments, an isolated Ab of the invention, including a mAb or antigen-binding portion thereof, induces proliferation and/or IFN-γ secretion in a CHO-svCD3-CD32A assay with an $EC_{50}$ of: about 0.05 nM or lower, about 0.04 nM or lower, about 0.03 nM or lower, about 0.025 nM or lower, between about 0.0005 nM and about 0.05 nM, between about 0.0005 nM and about 0.04 nM, between about 0.0005 nM and about 0.03 nM, between about 0.001 nM and about 0.05 nM, between about 0.001 nM and about 0.04 nM, or between about 0.001 nM and about 0.03 nM. In certain embodiments, an isolated Ab of the invention, including a mAb or antigen-binding portion thereof, induces proliferation in a CHO-svCD3-CD32A assay with a mean $EC_{50}$ of about 0.009 nM. In certain embodiments, an isolated Ab of the invention, including a mAb or antigen-binding portion thereof, induces IFN-γ secretion in a CHO-svCD3-CD32A assay with a mean $EC_{50}$ of about 0.008 nM.

In certain embodiments, an isolated Ab of the invention, including a mAb or antigen-binding portion thereof, induces proliferation of $CD4^+CD45RO^+$ memory T cells. In certain embodiments, an isolated Ab of the invention, including a mAb or antigen-binding portion thereof, induces proliferation of $CD4^+CD45RO^+$ memory T cells with an $EC_{50}$ of: about 0.01 nM or less, about 0.009 nM or less, about 0.008 nM or less, about 0.007 nM or less, about 0.006 nM or less, about 0.005 nM or less, between about 0.001 nM and about 0.01 nM, between about 0.002 nM and about 0.008 nM, between about 0.003 nM and about 0.007 nM, or between about 0.004 nM and about 0.006 nM.

In certain embodiments, an isolated Ab of the invention, including a mAb or antigen-binding portion thereof, induces IFN-γ secretion in $CD4^+CD45RO^+$ memory T cells. In certain embodiments, an isolated Ab of the invention, including a mAb or antigen-binding portion thereof, induces IFN-γ secretion in $CD4^+CD45RO^+$ memory T cells with an $EC_{50}$ of: about 0.05 nM or less, about 0.04 nM or less, about 0.03 nM or less, about 0.02 nM or less, between about 0.005 nM and about 0.05 nM, between about 0.005 nM and about 0.04 nM, between about 0.005 nM and about 0.03 nM, between about 0.005 nM and about 0.02 nM, between about 0.01 nM and about 0.05 nM, between about 0.01 nM and about 0.04 nM, between about 0.01 nM and about 0.03 nM, or between about 0.01 nM and about 0.02 nM.

In certain embodiments, an isolated Ab of the invention, including a mAb or antigen-binding portion thereof, increases IL-2 release from *staphylococcus* enterotoxin B (SEB)-stimulated human PBMCs. In certain embodiments, an isolated Ab of the invention, including a mAb or antigen-binding portion thereof, increases IL-2 release from SEB-stimulated human PBMCs by greater than about 50% in the presence of a cross-linker. In certain embodiments, the percentage by which IL-2 release is increased is in comparison to a negative control IgG1 mAb (e.g., a negative control hIgG1 mAb). In certain embodiments, the fold increase is at an Ab concentration between about 1 nM and about 10 nM.

In certain embodiments, an isolated Ab of the invention, including a mAb or antigen-binding portion thereof, increases IL-2 release at least about two-fold when combined with an anti-PD-1 Ab. In certain embodiments, the fold increase is in comparison to the mAb or antigen-binding portion thereof in the absence of an anti-PD-1 Ab.

In certain embodiments, an isolated Ab of the invention, including a mAb or antigen-binding portion thereof, reverses Treg-mediated suppression of co-cultured $CD4^+$ responder T cells in the presence of MDDC and soluble OKT3. In certain embodiments, an isolated Ab of the invention, including a mAb or antigen-binding portion thereof, reverses Treg-mediated suppression of co-cultured $CD4^+$ responder T cells in the presence of MDDC and soluble OKT3 by at least about 70%. In certain embodiments, the percentage by which Treg-mediated suppression is reversed is in comparison to a negative control IgG1 mAb (e.g., a negative control hIgG1 mAb).

In certain embodiments, an isolated Ab of the invention, including a mAb or antigen-binding portion thereof, potentiates the proliferation of human T cells and induction of IFN-γ secretion by soluble CD70. In certain embodiments, an isolated Ab of the invention, including a mAb or antigen-binding portion thereof, potentiates the proliferation of human T cells and induction of IFN-γ secretion by soluble CD70 with an $EC_{50}$ of about 0.01 nM or lower, about 0.009 nM or lower, about 0.008 nM or lower, about 0.007 nM or lower, about 0.006 nM or lower, about 0.005 nM or lower, between about 0.001 nM and about 0.01 nM, between about 0.002 nM and about 0.008 nM, or between about 0.003 nM and about 0.005 nM and/or potentiates the induction of IFN-γ secretion with an $EC_{50}$ of about 0.01 nM or lower, about 0.009 nM or lower, about 0.008 nM or lower, about 0.007 nM or lower, between about 0.001 nM and about 0.01 nM, between about 0.002 nM and about 0.008 nM, or between about 0.005 nM and about 0.007 nM.

In certain embodiments, an isolated Ab of the invention, including a mAb or antigen-binding portion thereof, has a different characteristic as compared to a negative control Ab and/or a different anti-CD27 Ab. In certain embodiments, the negative control Ab is a hIgG1 Ab. In certain embodiments, the different anti-CD27 Ab is 1F5, which is an anti-hCD27 mAb having the heavy and light chain sequences set forth as SEQ ID NOs: 20 and 21, respectively, as shown in Table 5. In certain embodiments, an isolated Ab of the invention, including a mAb or antigen-binding portion thereof, exhibits one or more characteristics that are markedly superior and/or therapeutically advantageous compared to known anti-CD27 Abs. For example, in certain embodiments, an isolated Ab of the invention, including a mAb or antigen-binding portion thereof, as compared to a negative control Ab and/or a different anti-CD27 Ab: has a higher affinity for hCD27 and/or cCD27, as shown by, e.g., $K_D$ or $EC_{50}$ values; is a hCD27 and/or cCD27 agonist; is a ligand non-blocker; does not specifically bind to rat CD27 and/or mouse CD27 as measured by SPR or flow cytometry; does not specifically bind to one or more TNF receptor superfamily members selected from the group consisting of CD30, HVEM, DR5, 4-1BB, CD40, OX40, GITR, and any combination thereof; does not specifically bind to one or more human tissues at concentrations up to 10 μg/mL, wherein the human tissues are selected from the group consisting of thyroid, lung, skin, uterus, prostate, liver, kidney, pancreas, adrenal, pituitary, placenta, testis, cerebrum, cerebellum, heart, peripheral nerve, and any combination thereof; causes higher induction of NF-κB and MAPK signaling in naïve and pre-activated human T cells stimulated by an anti-CD3 Ab and an anti-CD28 Ab; causes higher induction of proliferation and/or IFN-γ secretion in a CHO-svCD3-CD32A assay; causes higher induction of proliferation of CD4$^+$CD45RO$^+$ memory T cells; causes higher induction of IFN-γ secretion in CD4$^+$CD45RO$^+$ memory T cells; causes a higher increase in IL-2 release from *staphylococcus* enterotoxin B (SEB)-stimulated human PBMCs; causes a higher reversal of Treg-mediated suppression of co-cultured CD4$^+$ responder T cells in the presence of MDDC and soluble OKT3; potentiates, or potentiates at higher levels, the proliferation of human T cells and induction of IFN-γ secretion by soluble CD70; has a higher efficacy in inhibiting growth of tumor cells and/or tumors in vitro and/or in vivo; and any combination thereof.

Binding of Anti-CD27 Abs to T Cells

In certain embodiments, an isolated Ab of the invention, including a mAb or antigen-binding portion thereof, binds to human T cells with an $EC_{50}$ of about 0.1 nM or lower, about 0.09 nM or lower, about 0.08 nM or lower, about 0.07 nM or lower, about 0.06 nM or lower, about 0.05 nM or lower, about 0.04 nM or lower, between about 0.01 nM and about 0.1 nM, between about 0.015 nM and about 0.09 nM, or between about 0.02 nM and about 0.08 nM.

In certain embodiments, an isolated Ab of the invention, including a mAb or antigen-binding portion thereof, binds to cynomolgus T cells with $EC_{50}$ of about 0.5 nM or lower, about 0.4 nM or lower, about 0.3 nM or lower, about 0.2 nM or lower, about 0.1 nM or lower, between about 0.01 nM and about 0.5 nM, between about 0.02 nM and about 0.4 nM, or between about 0.03 and about 0.3 nM.

Functional Antigen-Binding Portions of Anti-CD27 Abs

Anti-CD27 Abs provided by the disclosure also include antigen-binding fragments in addition to full-length Abs. It has been amply demonstrated that the antigen-binding function of an Ab can be performed by fragments of a full-length Ab. Examples of binding fragments encompassed within the term "antigen-binding portion" of an Ab include (i) a Fab fragment, a monovalent fragment consisting of the $V_L$, $V_H$, $C_L$ and $C_{H1}$ domains; (ii) a F(ab')$_2$ fragment, a bivalent fragment consisting of two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an Ab; and (v) a single-domain Ab (sdAb) or nanobody, consisting of a single monomeric variable domain of an Ab. In addition to conventional Abs, camelid species such as camels, alpacas and llamas, and cartilaginous fish such as sharks and rays contain a subset of heavy chain Abs (hcAbs) consisting of heavy chain homodimers comprising three CDRs and lacking light chains. The first sdAbs were originally engineered from the hcAbs found in camelids (these are called VIM fragments) or in cartilaginous fish ($V_{NAR}$ fragments), but can also be generated by splitting the dimeric variable domains from conventional Abs. In addition to sdAbs derived from heavy chain variable domains, nanobodies derived from light chains have also been shown to bind selectively to specific antigens.

Ab fragments, obtained initially through proteolysis with enzymes such as papain and pepsin, have been subsequently engineered into monovalent and multivalent antigen-binding fragments. For example, although the two domains of the Fv fragment, $V_L$ and $V_H$, are coded for by separate genes, they can be joined, using recombinant methods, by a synthetic linker peptide that enables them to be made as a single protein chain in which the $V_L$ and $V_H$ regions pair to form monovalent molecules known as single chain variable fragments (scFv). Divalent or bivalent scFv's (di-scFv's or bi-scFv's) can be engineered by linking two scFv's in within a single peptide chain known as a tandem scFv which contains two $V_H$ and two $V_L$ regions. ScFv dimers and higher multimers can also be created using linker peptides of fewer than 10 amino acids that are too short for the two variable regions to fold together, which forces the scFv's to dimerize and produce diabodies or form other multimers. Diabodies have been shown to bind to their cognate antigen with much higher affinity than the corresponding scFv's, having dissociation constants up to 40-fold lower than the $K_D$ values for the scFv's. Very short linkers (≤3 amino acids) lead to the formation of trivalent triabodies or tetravalent tetrabodies that exhibit even higher affinities for to their antigens than diabodies. Other variants include minibodies, which are scFv-$C_{H3}$ dimers, and larger scFv-Fc fragments (scFv-$C_{H2}$-$C_{H3}$ dimers), and even an isolated CDR may exhibit antigen-binding function. These Ab fragments are engineered using conventional recombinant techniques known to those of skill in the art, and the fragments are screened for utility in the same manner as are intact Abs. All of the above proteolytic and engineered fragments of Abs and related variants (see Hollinger and Hudson, 2005; Olafsen and Wu, 2010, for further details) are intended to be encompassed within the term "antigen-binding portion" of an Ab.

In certain aspects of the disclosed invention, the antigen-binding portion of an isolated anti-CD27 Ab is an Ab fragment or a single chain Ab. In certain embodiments, the Ab fragment is selected from a Fab, F(ab')$_2$, Fd and Fv fragment, a sdAb, a single-chain variable fragment (scFv), a divalent scFv (di-scFv) and bivalent scFv (bi-scFv), a diabody, a minibody, and a CDR. In certain preferred embodiments, the Ab fragment is selected from a Fab, F(ab')$_2$, Fd and Fv fragment and a single chain variable fragment (scFv).

In certain embodiments, the isolated anti-CD27 Ab or antigen-binding portion thereof is a human Ab or a fragment thereof. In other embodiments, it is a humanized Ab or a fragment thereof. In further embodiments, it is a chimeric Ab or a fragment thereof. In other embodiments, the isolated anti-CD27 Ab or antigen-binding portion thereof is a mouse Ab or fragment thereof. For administration to human subjects, the Abs are preferably chimeric Abs or, more preferably, humanized or human Abs. Such chimeric, humanized, human or mouse mAbs can be prepared and isolated by methods well known in the art.

Anti-CD27 Immunoconjugates

In another aspect, the present invention relates to any one of the isolated anti-CD27 Abs disclosed herein, or an antigen-binding portion thereof, linked to a therapeutic agent, such as a cytotoxin or a radioactive isotope. Such conjugates are referred to herein as "immunoconjugates". Cytotoxins can be conjugated to Abs of the invention using linker technology available in the art. Methods for preparing radioimmunoconjugates are also established in the art.

Bispecific Molecules

In another aspect, the present invention relates to bispecific molecules comprising any one of the isolated anti-CD27 Abs disclosed herein, or an antigen-binding portion thereof, linked to a binding domain that has a different binding specificity than the anti-CD27 mAb or antigen-binding portion thereof. The binding domain may be a functional molecule, e.g., another Ab, antigen-binding portion of an Ab, or a ligand for a receptor, such that the bispecific molecule generated binds to at least two different binding sites or target molecules.

Nucleic Acids Encoding Anti-CD27 Abs and Use for Expressing Abs

Another aspect of the disclosure pertains to nucleic acids that encode the isolated anti-CD27 Abs of the invention. The disclosure provides an isolated nucleic acid encoding any of the CD27 Abs or antigen-binding portions thereof described herein. An "isolated" nucleic acid refers to a nucleic acid composition of matter that is markedly different, i.e., has a distinctive chemical identity, nature and utility from nucleic acids as they exist in nature. For example, an isolated DNA, unlike native DNA, is a free-standing portion of a native DNA and not an integral part of a larger structural complex, the chromosome, found in nature. Further, an isolated DNA, unlike native DNA, can be used as a PCR primer or a hybridization probe for, among other things, measuring gene expression and detecting biomarker genes or mutations for diagnosing disease or predicting the efficacy of a therapeutic. An isolated nucleic acid may also be purified so as to be substantially free of other cellular components or other contaminants, e.g., other cellular nucleic acids or proteins, using standard techniques well known in the art.

Nucleic acids of the invention can be obtained using standard molecular biology techniques. For Abs expressed by hybridomas (e.g., hybridomas prepared from transgenic mice carrying human Ig genes as described in Example 1), cDNAs encoding the light and heavy chains or variable regions of the Ab made by the hybridoma can be obtained by standard PCR amplification techniques. Once DNA fragments encoding $V_H$ and $V_L$ segments are obtained, these DNA fragments can be further manipulated using standard recombinant DNA techniques, for example, to convert the variable region DNAs to full-length Ab chain genes, to Fab fragment genes, or to a scFv gene. For Abs obtained from an Ig gene library (e.g., using phage display techniques), nucleic acids encoding the Ab can be recovered from the library.

A nucleic acid of the invention can be, for example, RNA or DNA such as cDNA or genomic DNA. In preferred embodiments, the nucleic acid is a cDNA.

This disclosure also provides an expression vector comprising an isolated nucleic acid which encodes an anti-CD27 Ab or antigen-binding portion thereof. The disclosure further provides a host cell comprising said expression vector. Eukaryotic cells, and most preferably mammalian host cells, are preferred as host cells for expressing Abs because such eukaryotic cells, and in particular mammalian cells, are more likely than prokaryotic cells to assemble and secrete a properly folded and immunologically active Ab. Preferred mammalian host cells for expressing the recombinant Abs of the invention include Chinese Hamster Ovary (CHO) cells (Kaufman and Sharp, 1982), NSO myeloma cells, COS cells and SP2 cells.

The host cell may be used in a method for preparing an anti-CD27 mAb or an antigen-binding portion thereof, which method comprises expressing the mAb or antigen-binding portion thereof in the host cell and isolating the mAb or antigen-binding portion thereof from the host cell. The host cell may be used ex vivo or in vivo. The DNAs encoding the Ab heavy and light chains can be inserted into separate expression vectors or, more typically, are both inserted into the same vector. The $V_H$ and $V_L$ segments of an Ab can be used to create full-length Abs of any isotype by inserting DNAs encoding these variable regions into expression vectors already encoding heavy chain and light chain constant regions of the desired isotype such that the $V_H$ segment is operatively linked to the CH segment(s) within the vector and the $V_\kappa$ segment is operatively linked to the $C_L$ segment within the vector.

Another aspect of this invention relates to a transgenic mouse comprising human Ig heavy and light chain transgenes, wherein the mouse expresses any of the anti-CD27 HuMAbs disclosed herein. The invention also encompasses a hybridoma prepared from said mouse, wherein the hybridoma produces the HuMAb.

Anti-PD-1/Anti-PD-L1 Abs Suitable for Use in the Disclosed Therapeutic Methods

Anti-PD-1 Abs suitable for use in the methods for cancer treatment, compositions or kits disclosed herein include isolated Abs, preferably mAbs or antigen-binding portions thereof, that bind to PD-1 with high specificity and affinity, block the binding of PD-L1 and/or PD-L2 to PD-1, and inhibit the immunosuppressive effect of the PD-1 signaling pathway. Similarly, anti-PD-L1 Abs suitable for use in these methods are isolated Abs, preferably mAbs or antigen-binding portions thereof, that bind to PD-L1 with high specificity and affinity, block the binding of PD-L1 to PD-1 and CD80 (B7-1), and inhibit the immunosuppressive effect of the PD-1 signaling pathway. In any of the therapeutic methods disclosed herein, an anti-PD-1 or anti-PD-L1 Ab includes an antigen-binding portion or fragment that binds to the PD-1 receptor or PD-L1 ligand, respectively, and exhibits functional properties similar to those of whole Abs in inhibiting receptor-ligand binding and reversing the inhibition of T cell activity, thereby upregulating an immune response.

Anti-PD-1 Abs

MAbs that bind specifically to PD-1 with high affinity have been disclosed in U.S. Pat. No. 8,008,449. Other anti-PD-1 mAbs have been described in, for example, U.S. Pat. Nos. 7,488,802, 8,168,757, 8,354,509, and 9,205,148. The anti-PD-1 mAbs disclosed in U.S. Pat. No. 8,008,449 have been demonstrated to exhibit several or all of the following characteristics: (a) binding to human PD-1 with a $K_D$ of about 50 nM or lower, as determined by the SPR (BIACORE®) biosensor system; (b) not substantially binding to human CD28, CTLA-4 or ICOS; (c) increasing T-cell proliferation, interferon-γ production and IL-2 secretion in a Mixed Lymphocyte Reaction (MLR) assay; (d) binding to human PD-1 and cynomolgus monkey PD-1; (e) inhibiting the binding of PD-L1 and PD-L2 to PD-1; (f) releasing inhibition imposed by Treg cells on proliferation and interferon-γ production of CD4$^+$CD25$^-$ T cells; (g) stimulating antigen-specific memory responses; (h) stimulating Ab responses; and (i) inhibiting tumor cell growth in vivo. Anti-PD-1 Abs usable in the disclosed methods of treatment, compositions or kits include mAbs that bind specifically to human PD-1 with high affinity and exhibit at least five, and preferably all, of the preceding characteristics. For example, an anti-PD-1 Ab suitable for use in the therapeutic methods disclosed herein (a) binds to human PD-1 with a $K_D$ of about 10 nM to 0.1 nM, as determined by SPR (BIACORE®); (b) increases T-cell proliferation, interferon-γ production and IL-2 secretion in a MLR assay; (c) inhibits the binding of PD-L1 and PD-L2 to PD-1; (d) reverses inhibition imposed by Tregs on proliferation and interferon-γ production of CD4$^+$CD25$^-$ T cells; (e) stimulates antigen-specific memory responses; and (f) inhibits tumor cell growth in vivo.

Other anti-PD-1 mAbs have been described in, for example, U.S. Pat. Nos. 6,808,710, 7,488,802, 8,168,757, 8,354,509, and 9,987,500, U.S. Publication No. 2016/0272708, and PCT Publication Nos. WO 2008/156712, WO 2012/145493, WO 2014/179664, WO 2014/194302, WO 2014/206107, WO 2015/035606, WO 2015/085847, WO 2015/112900, WO 2016/106159, WO 2016/197367, WO 2017/020291, WO 2017/020858, WO 2017/024465, WO 2017/024515, WO 2017/025016, WO 2017/025051, WO 2017/040790, WO 2017/106061, WO 2017/123557, WO 2017/132827, WO 2017/133540, each of which is incorporated by reference in its entirety.

In certain embodiments, the anti-PD-1 mAb is selected from the group consisting of nivolumab (OPDIVO®; formerly designated 5C4, BMS-936558, MDX-1106, or ONO-4538), pembrolizumab (KEYTRUDA®; formerly designated lambrolizumab and MK-3475; see WO 2008/156712A1), cemiplimab (LIBTAYO®; formerly known as REGN-2810; see WO 2015/112800), PDR001 (see WO 2015/112900), MEDI-0680 (formerly designated AMP-514; see WO 2012/145493), JS001 (see Liu and Wu, 2017), BGB-A317 (see WO 2015/035606 and US 2015/0079109), INCSHR1210 (SHR-1210; see WO 2015/085847; Liu and Wu, 2017), TSR-042 (ANB011; see WO 2014/179664), GLS-010 (WBP3055; see Liu and Wu, 2017), AM-0001 (see WO 2017/123557), STI-1110 (see WO 2014/194302), AGEN2034 (see WO 2017/040790), and MGD013 (see WO 2017/106061).

In certain preferred embodiments of any of the therapeutic methods described herein comprising administration of an anti-PD-1 Ab, the anti-PD-1 Ab is nivolumab (OPDIVO®), which has already been approved by the U.S. Food and Drug Administration (FDA) for treating multiple different cancers. Nivolumab is a fully human IgG4 (S228P) PD-1 immune checkpoint inhibitor Ab that selectively prevents interaction with PD-1 ligands (PD-L1 and PD-L2), thereby blocking the down-regulation of antitumor T-cell functions (described as mAb C5 in U.S. Pat. No. 8,008,449; Wang et al., 2014). In other preferred embodiments, the anti-PD-1 Ab is pembrolizumab (KEYTRUDA®; a humanized monoclonal IgG4 Ab directed against PD-1 and described as h409A11 in U.S. Pat. No. 8,354,509), which has also been approved for multiple cancer indications.

Anti-PD-1 Abs usable in the disclosed methods, compositions or kits also include isolated Abs, preferably mAbs, that bind specifically to human PD-1 (hPD-1) and cross-compete for binding to human PD-1 with any one of the anti-PD-1 Abs described herein, e.g.: nivolumab (5C4; see, e.g., U.S. Pat. No. 8,008,449; WO 2013/173223) and pembrolizumab. Abs that cross-compete with a reference Ab, e.g., nivolumab or pembrolizumab, for binding to an antigen, in this case human PD-1, can be readily identified in standard PD-1 binding assays such as BIACORE® analysis, ELISA assays or flow cytometry (see, e.g., WO 2013/173223). In certain embodiments, the anti-PD-1 Ab binds to the same epitope as any of the anti-PD-1 Abs described herein, e.g., nivolumab or pembrolizumab.

An anti-PD-1 Ab usable in the methods of the disclosed invention also includes an antigen-binding portion, including a Fab, F(ab')$_2$, Fd or Fv fragment, a sdAb, a scFv, di-scFv or bi-scFv, a diabody, a minibody or an isolated CDR (see Hollinger and Hudson, 2005; Olafsen and Wu, 2010, for further details).

In certain embodiments, the isolated anti-PD-1 Ab or antigen-binding portion thereof comprises a heavy chain constant region which is of a human IgG1, IgG2, IgG3 or IgG4 isotype. In certain preferred embodiments, the anti-PD-1 Ab or antigen-binding portion thereof comprises a heavy chain constant region which is of a human IgG4 isotype. In other embodiments, the anti-PD-1 Ab or antigen-binding portion thereof is of a human IgG1 isotype. In certain other embodiments, the IgG4 heavy chain constant region of the anti-PD-1 Ab or antigen-binding portion thereof contains an S228P mutation (numbered according to the EU numbering system, Kabat et al., 1991; or, alternatively, S241P, numbered according to the Kabat system, Kabat et al., 1987) which replaces a serine residue in the hinge region with the proline residue normally found at the corresponding position in IgG1 isotype Abs. This mutation, which is present in nivolumab, prevents Fab arm exchange with endogenous IgG4 Abs, while retaining the low affinity for activating Fc receptors associated with wild-type IgG4 Abs (Wang et al., 2014). In yet other embodiments, the Ab comprises a light chain constant region which is a human kappa or lambda constant region.

In other embodiments of the present methods, the anti-PD-1 Ab or antigen-binding portion thereof is a mAb or an antigen-binding portion thereof. For administration to human subjects, the anti-PD-1 Ab is preferably a chimeric Ab or, more preferably, a humanized or human Ab. Such chimeric, humanized or human mAbs can be prepared and isolated by methods well known in the art, e.g., as described in U.S. Pat. No. 8,008,449.

Anti-PD-L1 Abs

Because anti-PD-1 and anti-PD-L1 target the same signaling pathway and have been shown in clinical trials to exhibit comparable levels of efficacy in a variety of cancers (see, e.g., Brahmer et al., 2012; WO 2013/173223), an anti-PD-L1 Ab may be substituted for the anti-PD-1 Ab in the combination therapy methods disclosed herein.

Anti-PD-L1 Abs suitable for use in the disclosed methods, compositions or kits are isolated Abs that bind to PD-L1 with high specificity and affinity, block binding of PD-L1 to PD-1 and to CD80, and inhibit the immunosuppressive effect of the PD-1 signaling pathway. MAbs that bind specifically to PD-L1 with high affinity have been disclosed in U.S. Pat. No. 7,943,743. Other anti-PD-L1 mAbs have been described in, for example, U.S. Pat. Nos. 8,217,149, 8,779,108, 9,175,082, 9,624,298 and 9,938,345, and PCT Publication No. WO 2012/145493. The anti-PD-1 HuMAbs disclosed in U.S. Pat. No. 7,943,743 have been demonstrated to exhibit one or more of the following characteristics: (a) binding to human PD-1 with a $K_D$ of about 50 mM or lower, as determined by SPR (BIACORE®); (b) increasing T-cell proliferation, interferon-$\gamma$ production and IL-2 secretion in a MLR assay; (c) stimulating Ab responses; (d) inhibiting the binding of PD-L1 to PD-1; and (e) reversing the suppressive effect of Tregs on T cell effector cells and/or dendritic cells. Anti-PD-L1 Abs for use in the therapeutic methods disclosed herein include isolated Abs, preferably mAbs, that bind specifically to human PD-L1 with high affinity and exhibit at least one, in some embodiments at least three, and preferably all, of the preceding characteristics. For example, an anti-PD-L1 Ab suitable for use in these methods (a) binds to human PD-1 with a $K_D$ of about 50 mM to 0.1 mM, as determined by SPR (BIACORE®); (b) increases T-cell proliferation, interferon-$\gamma$ production and IL-2 secretion in a MLR assay; (c) inhibits the binding of PD-L1 to PD-1 and to CD80; and (d) reverses the suppressive effect of Tregs on T cell effector cells and/or dendritic cells.

A suitable anti-PD-L1 Ab for use in the present methods is BMS-936559 (formerly MDX-1105; designated 12A4 in U.S. Pat. No. 7,943,743). Other suitable anti-PD-L1 Abs include atezolizumab (TECENTRIQ®; previously known as RG7446 and MPDL3280A; designated YW243.55S70 in U.S. Pat. No. 8,217,149; see, also, Herbst et al., 2014), durvalumab (IMFINZI®; previously known as MEDI-4736; designated 2.14H9OPT in U.S. Pat. No. 8,779,108), avelumab (BAVENCIO®; previously known as MSB-0010718C; designated A09-246-2 in U.S. Pat. No. 9,624,298), STI-A1014 (designated H6 in U.S. Pat. No. 9,175,082), CX-072 (see WO 2016/149201), KN035 (see Zhang et al., 2017), LY3300054 (see, e.g., WO 2017/034916), and CK-301 (see Gorelik et al., 2017).

Anti-PD-L1 Abs suitable for use in the disclosed methods, compositions or kits also include isolated Abs that bind specifically to human PD-L1 and cross-compete for binding to human PD-L1 with a reference Ab which may be any one of the anti-PD-L1 Abs disclosed herein, e.g., BMS-936559 (12A4; see, e.g., U.S. Pat. No. 7,943,743; WO 2013/173223), atezolizumab, durvalumab, avelumab or STI-A1014. The ability of an Ab to cross-compete with a reference Ab for binding to human PD-L1 demonstrates that such Ab binds to the same epitope region of PD-L1 as the reference Ab and is expected to have very similar functional properties to that of the reference Ab by virtue of its binding to substantially the same epitope region of PD-L1. In some embodiments, the anti-PD-L1 Ab binds to the same epitope as any of the anti-PD-L1 Abs described herein, e.g., atezolizumab, durvalumab, avelumab or STI-A1014. Cross-competing Abs can be readily identified based on their ability to cross-compete with a reference Ab such as atezolizumab or avelumab in standard PD-L1 binding assays such as BIA-CORE® analysis, ELISA assays or flow cytometry that are well known to persons skilled in the art (see, e.g., WO 2013/173223).

In certain preferred embodiments, the isolated anti-PD-L1 Abs for use in the present methods are mAbs. In other embodiments, especially for administration to human subjects, these Abs are preferably chimeric Abs, or more preferably humanized or human Abs. Chimeric, humanized and human Abs can be prepared and isolated by methods well known in the art, e.g., as described in U.S. Pat. No. 7,943,743.

In certain embodiments, the anti-PD-L1 Ab or antigen-binding portion thereof comprises a heavy chain constant region which is of a human IgG1, IgG2, IgG3 or IgG4 isotype. In certain other embodiments, the anti-PD-L1 Ab or antigen-binding portion thereof is of a human IgG1 of IgG4 isotype. In further embodiments, the sequence of the IgG4 heavy chain constant region of the anti-PD-L1 Ab or antigen-binding portion thereof contains an S228P mutation. In other embodiments, the Ab comprises a light chain constant region which is a human kappa or lambda constant region.

Anti-PD-L1 Abs of the invention also include antigen-binding portions of the above Abs, including Fab, F(ab')2, Fd, Fv, and scFv, di-scFv or bi-scFv, and scFv-Fc fragments, nanobodies, diabodies, triabodies, tetrabodies, and isolated CDRs, that bind to PD-L1 and exhibits functional properties similar to those of whole Abs in inhibiting receptor binding and up-regulating the immune system.

Therapeutic Methods

Treatment of Cancer with an Anti-CD27 Ab as Monotherapy

As described in Example 8, the anti-mCD27 mAb, 8H5, inhibited tumor growth in the CT26 colon cancer and fibrosarcoma tumor models (see FIG. 14 and Table 7). Accordingly, this disclosure provides a method for treating a subject afflicted with a cancer, comprising administering to the subject a therapeutically effective amount of any one of the anti-CD27 Abs, immunoconjugates or bispecific molecules disclosed herein, or a pharmaceutical composition comprising any one of said anti-CD27 Abs, immunoconjugates or bispecific molecules, such that the subject is treated.

The disclosure also provides a method for inhibiting growth of tumor cells in a subject, comprising administering to the subject a therapeutically effective amount of any one of the anti-CD27 Abs, immunoconjugates or bispecific molecules disclosed herein, or a pharmaceutical composition comprising any one of said anti-CD27 Abs, immunoconjugates or bispecific molecules, such that growth of tumor cells in the subject is inhibited.

Treatment of Cancer with an Anti-CD27 Ab in Combination with Another Anti-Cancer Agent As described in Example 8, the anti-mCD27 mAb, 8H5, potentiated the activity of an anti-mPD-1 mAb in different cancer types including the CT26 colon cancer, SA1N fibrosarcoma and the EG7 lymphoma mouse models (see FIG. 14 and Table 7). Thus, anti-CD27 Abs are much more effective in inhibiting tumor growth when combined with a checkpoint inhibitor such as an anti-PD-1 Ab. Accordingly, this disclosure provides a method for treating a subject afflicted with a cancer, comprising administering to the subject a therapeutically effective amount of: (a) any one of the anti-CD27 Abs, immunoconjugates or bispecific molecules disclosed herein, or a pharmaceutical composition comprising any one of said anti-CD27 Abs, immunoconjugates or bispecific molecules; and (b) an additional therapeutic agent for treating cancer, such that the subject is treated.

The disclosure also provides a method for inhibiting growth of tumor cells in a subject, comprising administering to the subject a therapeutically effective amount of: (a) any one of the anti-CD27 Abs, immunoconjugates or bispecific molecules disclosed herein, or a pharmaceutical composition comprising any one of said anti-CD27 Abs, immunoconjugates or bispecific molecules; and (b) an additional therapeutic agent for treating cancer, such that growth of tumor cells in the subject is inhibited.

In certain preferred embodiments of any of the present methods, the subject is a human patient.

In certain embodiments, the additional therapeutic agent is a compound that reduces inhibition, or increases stimulation, of the immune system. For example, the additional therapeutic agent may be a small-molecule compound, a macrocyclic peptide, a fusion protein, or an Ab. In further embodiments, the additional therapeutic agent is an antagonistic Ab that binds specifically to PD-1, PD-L1, CTLA-4, LAG-3, BTLA, TIM-3, KIR, KLRG-1, A2aR, TIGIT, the VISTA receptor, CD244, or CD160. In other embodiments, the additional therapeutic agent is an agonistic Ab that binds specifically to ICOS, CD137, CD134, CD27, GITR or HVEM. In certain embodiments, the additional therapeutic agent is an antagonistic Ab or antigen-binding portion thereof that binds specifically to PD-1 or to PD-L1, disrupts the interaction between PD-1 and PD-L1, and inhibits PD-1/PD-L1 signaling. In certain embodiments, the Ab or antigen-binding portion thereof that binds specifically to PD-1 or to PD-L1 is a chimeric, humanized, or human mAb or antigen-binding portion thereof. In certain embodiments, the additional therapeutic agent is an antagonistic Ab or antigen-binding portion thereof that binds specifically to PD-1 and cross-competes with nivolumab for binding to human PD-1. In certain embodiments, the additional therapeutic agent is an antagonistic Ab or antigen-binding portion thereof that binds specifically to PD-1 and is nivolumab or pembrolizumab. In certain embodiments, the additional therapeutic agent is an antagonistic Ab or antigen-binding portion thereof that binds specifically to PD-L1 and cross-competes with the Ab designated BMS-936559 (WO 2013/173223) for binding to human PD-L1. In certain embodiments, the additional therapeutic agent is an antagonistic Ab or antigen-binding portion thereof that binds specifically to PD-L1 and is atezolizumab, durvalumab, avelumab, or the Ab designated BMS-936559 (WO 2013/173223).

Cancers Amenable to Treatment by Disclosed Methods

Immuno-oncology, which relies on using the practically infinite flexibility of the immune system to attack and destroy cancer cells, is applicable to treating a very broad range of cancers (see, e.g., Yao et al., 2013; Callahan et al., 2016; Pianko et al., 2017; Farkona et al., 2016; Kamta et al., 2017).

In certain embodiments, the disclosed therapy methods may be used to treat a cancer which is a solid tumor.

In certain embodiments, the solid tumor is a colon cancer or a fibrosarcoma. In certain embodiments, the solid tumor is a cancer selected from the group consisting of squamous cell carcinoma, small cell lung cancer (SCLC), non-small cell lung cancer (NSCLC), squamous NSCLC, non-squamous NSCLC, head and neck cancer, breast cancer, cancer of the esophagus, stomach cancer, gastrointestinal cancer, cancer of the small intestine, liver cancer, hepatocellular carcinoma (HCC), hepatoma, gallbladder and bile duct cancer, pancreatic cancer (PAC), pancreatic ductal adenocarcinoma (PDAC), kidney cancer, renal cell carcinoma (RCC), bladder cancer, cancer of the urethra, cancer of the ureter, colorectal cancer (CRC), colon carcinoma, cancer of the anal region, endometrial cancer, prostate cancer, neuroblastoma, glioma, glioblastoma, germ cell tumor, pediatric sarcoma, sinonasal natural killer, melanoma, skin cancer, Merkel cell carcinoma, basal cell carcinoma, bone cancer, cervical cancer, uterine cancer, carcinoma of the endometrium, carcinoma of the fallopian tubes, ovarian cancer, carcinoma of the cervix, carcinoma of the vagina, carcinoma of the vulva, testicular cancer, cancer of the endocrine system, tumors of the thymus gland, thymona, thyroid cancer, oral cancer, mouth cancer, cancer of the parathyroid gland, cancer of the adrenal gland, sarcoma of soft tissue, cancer of the penis, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, neuroblastoma, pituitary adenoma, epidermoid cancer, solid tumors of childhood, pediatric sarcoma, rhabdomyosarcoma, cancer of unknown primary origin, environmentally-induced cancers, virus-related cancers, AIDS-related cancers, cancers of viral origin, advanced cancer, unresectable cancer, metastatic cancer, refractory cancer, recurrent cancer, and any combination of the preceding solid tumors.

In certain embodiments, the solid tumor is a cancer selected from small cell lung cancer (SCLC), squamous non-small cell lung cancer (NSCLC), non-squamous NSCLC, and triple negative breast cancer (TNBC).

An anti-CD27 Ab of the invention may also be effective in earlier phases of disease where chemotherapy and/or radiation are key treatment modalities and there is a need promote sustained anti-tumor immunity. In certain embodiments, the solid tumor is a cancer selected from esophageal cancer, gastric cancer, rectal cancer, non-small cell lung cancer (NSCLC), and squamous cell carcinoma of the head and neck (SCCHN).

In certain other embodiments, the solid tumor is selected from melanoma, renal cancer, NSCLC, colorectal cancer, gastric cancer, bladder cancer and glioblastoma.

In certain embodiments, the disclosed therapeutic methods may be used to treat a cancer which is a hematological malignancy or the tumor cells are cells of a hematological malignancy. Hematological malignancies include liquid tumors derived from either of the two major blood cell lineages, i.e., the myeloid cell line (which produces granulocytes, erythrocytes, thrombocytes, macrophages and mast cells) or the lymphoid cell line (which produces B, T, NK and plasma cells), including all types of leukemias, lymphomas, and myelomas. Hematological malignancies that may be treated using the present therapy methods include, for example, cancers selected from acute lymphoblastic leukemia (ALL), acute myelogenous leukemia (AML), chronic lymphocytic leukemia (CLL), chronic myelogenous leukemia (CIVIL), Hodgkin's lymphoma (HL), non-Hodgkin's lymphomas (NHLs), multiple myeloma, smoldering myeloma, monoclonal gammopathy of undetermined significance (MGUS), advanced, metastatic, refractory and/or recurrent hematological malignancies, and any combinations of said hematological malignancies.

In other embodiments, the hematological malignancy is a cancer selected from acute, chronic, lymphocytic (lymphoblastic) and/or myelogenous leukemias, such as ALL, AML, CLL, and CML; lymphomas, such as HL, NHLs, of which about 85% are B cell lymphomas, including diffuse large B-cell lymphoma (DLBCL), follicular lymphoma (FL), chronic lymphocytic leukemia (CLL)/small lymphocytic lymphoma (SLL), mantle cell lymphoma, marginal zone B-cell lymphomas (mucosa-associated lymphoid tissue (MALT) lymphoma, nodal marginal zone B-cell lymphoma, and splenic marginal zone B-cell lymphoma), Burkitt lymphoma, lymphoplasmacytoid lymphoma (LPL; also known as Waldenstrom's macroglobulinemia (WM)), hairy cell lymphoma, and primary central nervous system (CNS) lymphoma, NHLs that are T cell lymphomas, including precursor T-lymphoblastic lymphoma/leukemia, T-lymphoblastic lymphoma/leukemia (T-Lbly/T-ALL), peripheral T-cell lymphomas such as cutaneous T-cell lymphoma (CTLC, i.e., mycosis fungoides, Sezary syndrome and others), adult T-cell lymphoma/leukemia, angioimmunoblastic T-cell lymphoma, extranodal natural killer/T-cell lymphoma nasal type, enteropathy-associated intestinal T-cell lymphoma (EATL), anaplastic large-cell lymphoma (ALCL), and peripheral T-cell lymphoma unspecified, acute myeloid lymphoma, lymphoplasmacytoid lymphoma, monocytoid B cell lymphoma, angiocentric lymphoma, intestinal T-cell lymphoma, primary mediastinal B-cell lymphoma, post-transplantation lymphoproliferative disorder, true histiocytic lymphoma, primary effusion lymphoma, diffuse histiocytic lymphoma (DHL), immunoblastic large cell lymphoma, and precursor B-lymphoblastic lymphoma; myelomas, such as multiple myeloma, smoldering myeloma (also called indolent myeloma), monoclonal gammopathy of undetermined significance (MGUS), solitary plasmocytoma, IgG myeloma, light chain myeloma, nonsecretory myeloma, and amyloidosis; and any combinations of said hematological malignancies. The present methods are also applicable to treatment of advanced, metastatic, refractory and/or recurrent hematological malignancies.

With respect to combination therapies, the anti-PD-1 Ab, nivolumab, has been shown to be effective in treating many different types of cancers (see, e.g., Brahmer et al., 2015; Guo et al., 2017; Pianko et al., 2017; WO 2013/173223), and is currently undergoing clinical trials in multiple solid and hematological cancers. Nivolumab has been approved to treat advanced melanoma, advanced non-small cell lung cancer, metastatic renal cell carcinoma, classical Hodgkin lymphoma, advanced squamous cell carcinoma of the head and neck, urothelial carcinoma, MSI-H or dMMR metastatic colorectal cancer, and hepatocellular carcinoma, and small cell lung cancer (Drugs.com—Opdivo Approval History: www.drugs.com/history/opdivo.html), with clinical trials in many other cancers ongoing. Similarly, other anti-PD-1 drugs such as pembrolizumab (KEYTRUDA®) and cemiplimab (LIBTAYO®), as well as anti-PD-L1 drugs such as atezolizumab (TECENTRIQ®), durvalumab (IMFINZI®) and avelumab BAVENCIO®) have been gaining approvals in a variety of indications. Accordingly, a wide variety of different cancers are treatable using combination of anti-CD27 Abs as disclosed herein and anti-PD-1/PD-L1 Abs. The high efficacy demonstrated for this combination of therapeutics allows a focus on cancers plagued by large unmet medical need.

Medical Uses of Anti-CD27 and Anti-PD-1/Anti-PD-L1 Abs

As noted above, this disclosure provides an isolated anti-CD27 Ab, preferably a mAb or an antigen-binding portion thereof, for use in a method for treating a subject afflicted with a cancer. The disclosure further provides an isolated anti-CD27 Ab, preferably a mAb or an antigen-binding portion thereof, and a checkpoint inhibitor such as an isolated anti-PD-1/anti-PD-L1 Ab, preferably a mAb or an antigen-binding portion thereof, for use in combination in a method for treating a subject afflicted with cancer. The anti-CD27 Ab may be used as monotherapy or in combination with a checkpoint inhibitor, such as anti-PD-1/anti-PD-L1 Ab, for treatment of the full range of cancers disclosed herein.

One aspect of the disclosed invention entails the use of an isolated anti-CD27 Ab or an antigen-binding portion thereof of the invention for the preparation of a medicament for treating a subject afflicted with a cancer. The anti-CD27 Ab may be used alone or in combination with a checkpoint inhibitor such as an isolated anti-PD-1/anti-PD-L1 Ab or an antigen-binding portion thereof for the preparation of the medicament for treating the cancer patient. Uses of any such anti-CD27 Ab and anti-PD-1/anti-PD-L1 Ab for the preparation of medicaments are broadly applicable to the full range of cancers disclosed herein.

This disclosure also provides an anti-CD27 Ab or an antigen-binding portion thereof in combination with a checkpoint inhibitor such as an isolated anti-PD-1/anti-PD-L1 Ab or an antigen-binding portion thereof for use in methods of treating cancer corresponding to all the embodiments of the methods of treatment employing this combination of therapeutics described herein.

Pharmaceutical Compositions and Dosage Regimens

Abs used in the any of the therapeutic methods disclosed herein may be constituted in a composition, e.g., a pharmaceutical composition containing an Ab and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier for a composition containing an Ab is suitable for intravenous (IV), intramuscular, subcutaneous (SC), parenteral, spinal or epidermal administration (e.g., by injection or infusion).

An option for SC injection is based on Halozyme Therapeutics' ENHANZE® drug-delivery technology, involving a co-formulation of an Ab with recombinant human hyaluronidase enzyme (rHuPH20) that removes traditional limitations on the volume of biologics and drugs that can be delivered subcutaneously due to the extracellular matrix (U.S. Pat. No. 7,767,429). It may be possible to co-formulate two Abs used in combination therapy into a single composition for SC administration.

A pharmaceutical composition of the invention may include one or more pharmaceutically acceptable salts, antioxidants, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. For administration of an anti-CD27, anti-PD-1 or anti-PD-L1 Ab or an antigen-binding portion thereof, including for combination use, the dosage may range from about 0.01 to about 20 mg/kg, preferably from about 0.1 to about 10 mg/kg, of the subject's body weight. For example, dosages can be about 0.1, 0.2, 0.3, 0.4, 0.5, 0.6, 0.7, 0.8, 0.9, 1, 2, 3, 5 or 10 mg/kg body weight. Alternatively, a fixed or flat dose, e.g., about 50 to about 2000 mg of the Ab or antigen-binding portion thereof, instead of a dose based on body weight, may be administered. For example, a fixed dose of about 50, 100, 200, 400, 500, 800, 1000, 1200, 1500, 1600 or 2000 mg of the antibody may be administered. The dosing schedule is typically designed to achieve exposures that result in sustained receptor occupancy (RO) based on typical pharmacokinetic properties of an Ab. An exemplary treatment regime entails administration once about every week, once about every 2 weeks, once about every 3 weeks, once about every 4 weeks, once about a month, once about every 3-6 months or longer. In certain preferred embodiments, the anti-CD27, anti-PD-1 or anti-PD-L1 Ab or antigen-binding portion thereof is administered to the subject once about every 2 weeks. In other preferred embodiments, the Ab or antigen-binding portion thereof is administered once about every 3 weeks. In other preferred embodiments, the Ab or antigen-binding portion thereof is administered once about every 4 weeks. The dosage and scheduling may change during a course of treatment. In certain preferred embodiments, a fixed or flat dose of about 240 mg of an anti-PD-1 Ab or an antigen-binding portion thereof is administered to the subject once about every 2 weeks. In other preferred embodiments, a fixed or flat dose of about 480 mg of an anti-PD-1 Ab or an antigen-binding portion thereof is administered to the subject once about every 4 weeks. In certain embodiments, the anti-PD-1 Ab is nivolumab.

When used in combinations, a subtherapeutic dosage of one or both Abs, e.g., a dosage of an anti-CD27, anti-PD-1 and/or anti-PD-L1 Ab or antigen-binding portion thereof lower than the typical or approved monotherapy dose, may be used. For example, a dosage of nivolumab that is lower than one of the approved dosages, 3 mg/kg every 2 weeks, for instance, 1.0 mg/kg or less every 2, 3 or 4 weeks, is regarded as a subtherapeutic dosage. RO data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al., 2010). Thus, 0.3 mg/kg dosing may allow for sufficient exposure to lead to significant biologic activity.

The synergistic interaction observed in mouse tumor models (Example 8) may permit the administration of any of the anti-CD27 and anti-PD-1/anti-PD-L1 Abs or antigen-binding portions thereof to a cancer patient at subtherapeutic dosages. In certain embodiments of the disclosed combination therapy methods, the anti-CD27 Ab or antigen-binding portion thereof is administered at a subtherapeutic dose to a cancer patient. In other embodiments, the anti-PD-1/anti-PD-L1 Ab or antigen-binding portion thereof is administered to the patient at a subtherapeutic dose. In further embodiments, the anti-PD-1/anti-PD-L1 and anti-CD27 Abs or antigen-binding portions thereof are each administered to the patient at a subtherapeutic dose.

The administration of such a subtherapeutic dose of one or both Abs may reduce adverse events compared to the use of higher doses of the individual Abs in monotherapy. Thus, the success of the disclosed methods of combination therapy may be measured not only in improved efficacy of the combination of Abs relative to monotherapy with these Abs, but also in increased safety, i.e., a reduced incidence of adverse events, from the use of lower dosages of the drugs in combination relative to the monotherapy doses.

In certain embodiments of any of the methods disclosed herein, the anti-CD27, anti-PD-1 and/or anti-PD-L1 Abs are formulated for intravenous (IV) administration or for subcutaneous (SC) injection. In certain embodiments, the anti-CD27 Ab or antigen-binding portion thereof and the anti-PD-1/anti-PD-L1 Ab or antigen-binding portion thereof are administered sequentially to the subject. "Sequential" administration means that one of the anti-CD27 and anti-PD-1/anti-PD-L1 Abs is administered before the other. Either Ab may be administered first; i.e., in certain embodiments, the anti-PD-1/anti-PD-L1 Ab is administered before the anti-CD27 Ab, whereas in other embodiments, the anti-CD27 Ab is administered before the anti-PD-1/anti-PD-L1 Ab. In certain embodiments, each Ab is administered by IV infusion, for example, by infusion over a period of about 30 minutes or about 60 minutes. In other embodiments, at least one Ab is administered by SC injection.

In certain embodiments of sequential IV administration, for the convenience of the patient, the anti-CD27 and anti-PD-1/anti-PD-L1 Abs or portions thereof are administered within 30 minutes of each other. Typically, when both the anti-CD27 and anti-PD-1/anti-PD-L1 Abs are to be delivered by IV administration on the same day, separate infusion bags and filters are used for each infusion. The infusion of the first Ab is promptly followed by a saline flush to clear the line of the Ab before starting the infusion of the second Ab. In other embodiments, the two Abs are administered within 1, 2, 4, 8, 24 or 48 h of each other.

The delivery of at least one Ab by SC administration reduces health care practitioner time required for administration and shortens the time for drug administration. For example, the use of SC injection could cut the time needed for IV administration, typically about 30-60 min, to about 5 min. In certain embodiments of sequential SC administration, the anti-CD27 and anti-PD-1/anti-PD-L1 Abs or portions thereof are administered within 10 min of each other.

Because checkpoint inhibitor Abs have been shown to produce very durable responses, in part due to the memory component of the immune system (see, e.g., WO 2013/173223; Lipson et al., 2013; Wolchok et al., 2013), the activity of an administered anti-PD-1/anti-PD-L1 Ab may be ongoing for several weeks, several months, or even several years. In certain embodiments, the present combination therapy methods involving sequential administration entail administration of an anti-CD27 Ab to a patient who has been previously treated with an anti-PD-1/anti-PD-L1 Ab. In further embodiments, the anti-CD27 Ab is administered to a patient who has been previously treated with, and progressed on, an anti-PD-1/anti-PD-L1 Ab. In other embodiments, the present combination therapy methods involving sequential administration entail administration of an anti-PD-1/anti-PD-L1 Ab to a patient who has been previously treated with an anti-CD27 Ab, optionally a patient whose cancer has progressed after treatment with the anti-CD27 Ab.

In certain other embodiments, the anti-PD-1/anti-PD-L1 and anti-CD27 Abs are administered concurrently, either admixed as a single composition in a pharmaceutically acceptable formulation for concurrent administration, or concurrently as separate compositions with each Ab in formulated in a pharmaceutically acceptable composition.

Kits

Also within the scope of the present invention are kits comprising an anti-CD27 Ab for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) one or more dosages ranging from about 0.1 to about 20 mg/kg body weight of any one of the anti-CD27 Abs or antigen-binding portions thereof, immunoconjugates or bispecific molecules disclosed herein, or a pharmaceutical composition comprising any one of said anti-CD27 Abs or antigen-binding portions thereof, immunoconjugates or bispecific molecules; and (b) instructions for using the mAb or portion thereof in any of the therapeutic methods disclosed herein. The disclosure further provides a kit for treating a subject afflicted with a cancer, the kit comprising: (a) one or more dosages ranging from about 0.1 to about 20 mg/kg body weight of any one of the anti-CD27 Abs or antigen-binding portions thereof, immunoconjugates or bispecific molecules disclosed herein, or a pharmaceutical composition comprising any one of said anti-CD27 Abs or antigen-binding portions thereof, immunoconjugates or bispecific molecules; (b) one or more dosages ranging from about 50 to about 2000 mg of any of the Abs or antigen-binding portions thereof that bind specifically to PD-1 or to PD-L1; and (c) instructions for using the anti-CD27 mAb and the checkpoint inhibitor, e.g., the anti-PD-1/anti-PD-L1 mAb, in any of the combination therapy methods disclosed herein.

In certain embodiments, the Abs may be co-packaged in unit dosage form. In certain preferred embodiments for treating human patients, the kit comprises an anti-human PD-1 Ab disclosed herein, e.g., nivolumab or pembrolizumab.

The present invention is further illustrated by the following examples which should not be construed as further limiting. The contents of all references cited throughout this application are expressly incorporated herein by reference.

Example 1

Generation of MAbs Against CD27

Human anti-CD27 mAbs were generated by immunizing transgenic mice that express human Ab genes with a human CD27 (hCD27) antigen to raise in the mice a repertoire of human Ig's specific for CD27, Rat anti-mouse CD27 mAbs were generated by immunizing rats with a mouse CD27 (mCD27) antigen.

Immunization of Human Immunoglobulin Transgenic Mice

HuMAbs to hCD27 were generated by immunizing human Ig transgenic mice (KM mouse, strain no. 325432) alternately with recombinant hCD27 containing hFc and histidine tag proteins (rhCD27-hFc-his) as well as CHO cells stably transfected with hCD27.

Generation of Hybridomas Producing MAbs to CD27

Mouse splenocytes were isolated from an immunized mouse as described above that showed a positive anti-CD27

IgG titer after immunization. Hybridomas were generated by fusions of the splenocytes with a mouse myeloma SP2/0 fusion partner.

Immunization of Rats

Surrogate mAbs to mCD27 were generated by immunizing rats with recombinant mouse CD27 containing Fc tag proteins (rmCD27-Fc).

Example 2

Screening and Selection of Human Anti-Human CD27 MAbs

Screening for MAbs that Selectively Bind to Human CD27

In order to generate HuMAbs that bind to hCD27, human Ig transgenic mice were immunized with a hCD27 antigen as described in Example 1.

Hybridoma supernatants were first screened for binding to hCD27 by enzyme-linked immunosorbent assay (ELISA). Antigen specificity was then confirmed by binding to hCD27+ T cells. Abs were next tested for their ability to block the interaction of CD27 and CD70 by flow cytometry and surface plasmon resonance (SPR).

Functional Screening for Agonistic Anti-CD27mAbs

Agonist activities of anti-CD27 Abs were determined in vitro using a CHO-svCD3-CD32a assay. In this assay, anti-CD27 agonistic Abs were crosslinked by virtue of binding to CD32a, resulting in enhanced svCD3-mediated activation of human CD4+ T cells.

The lead mAb, non-ligand blocker Clone 16D9, was selected for its superior binding affinity for h- and cCD27 and its superior agonism of activated T cells. The lead mAb was determined to have a relatively modest level of ADCC activity using IL-2-activated human NK cells co-cultured with human CD3+ T cells.

Optimization of Anti-hCD27 HuMAbs

Clone 16D9 subsequently underwent VH-A28T and VK-I20T-I22T-D43A framework reversions plus an S93N mutation in a light chain CDR. The modified clone was engineered as a human IgG1 and designated BMS-986215. BMS-986215 was engineered as a hIgG1 to allow the Fc crosslinking required for CD27 agonism.

The complete hCD27 amino acid sequence is shown in Table 1 and can be found under GENBANK® Accession No. AAH12160. Amino acids 1-20 as underlined in Table 1 represent a predicted signal peptide. See, e.g., CBS Prediction SignalP 4.1 (www.cbs.dtu.dk).

TABLE 1

Amino Acid Sequences for the Human CD27 Polypeptide
Amino Acid Sequence and SEQ ID NO.

```
  1  marphpwwlc vlgtivglsa tpapkscper hywaqgklcc qmcepgtflv kdcdqhrkaa
 61  qcdpcipgvs fspdhhtrph cescrhcnsg llvrnctita naecacrngw qcrdkectec
121  dplpnpslta rssqalsphp qpthlpyvse mleartaghm qtladfrqlp artlsthwpp
181  qrslcssdfi rilvifsgmf lvftlagalf lhqrrkyrsn kgespvepae pcryscpree
241  egstipiqed yrkpepacsp (SEQ ID NO: 1)
```

The amino acid sequences for the 6 CDR domains for HuMAb BMS-986215 as defined using the Kabat method are shown in Table 2.

The amino acid sequences for the $V_H$, $V_L$, $C_H$, $C_L$, heavy chain, and light chain for HuMAb BMS-986215 are shown in Table 3.

TABLE 2

Amino Acid Sequences for the 6 CDR Domains in HuMAb BMS-986215 as
Defined using the Kabat Method
Amino Acid Sequences and SEQ ID NOs.

| VH CDR1 | VH CDR2 | VH CDR3 | VL CDR1 | VL CDR2 | VL CDR3 |
|---|---|---|---|---|---|
| TTYAMN (SEQ ID NO: 2) | WINTNTGNPTYAQGFTG (SEQ ID NO: 3) | DFGGFDY (SEQ ID NO: 4) | RASQGISSALA (SEQ ID NO: 5) | DASSLES (SEQ ID NO: 6) | QQFNNYPRT (SEQ ID NO: 7) |

TABLE 3

Amino Acid Sequences for the $V_H$, $V_L$, $C_H$, $C_L$, Heavy Chain, and
Light Chain in HuMAb BMS-986215

Amino Acid Sequences and SEQ ID NOs.

| | |
|---|---|
| $V_H$ | QVQLVQSGSEVKKPGASVKVSCKASGYTFTTYAMNWVRQAPGQGLEWMGWI NTNTGNPTYAQGFTGRFVFSLDTSVNTAYLQISSLKAEDTAVYYCARDFGGFDY WGQGTLVTVSS (SEQ ID NO: 8) |

TABLE 3-continued

Amino Acid Sequences for the V_H, V_L, C_H, C_L, Heavy Chain, and Light Chain in HuMAb BMS-986215

| | Amino Acid Sequences and SEQ ID NOs. |
|---|---|
| V_L | AIQLTQSPSSLSASVGDRVTITCRASQGISSALAWYQQKPGKAPKLLINDASSLES GVPSRFSGSGSGTDFTLTISSLQPEDFATYYCQQFNNYPRTFGQGTKVEIK (SEQ ID NO: 9) |
| C_H | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCP PCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPEN NYKTTPPVLDSDGSFFLYSKLTVDKSRWQQGNVFSCSVMHEALHNHYTQKSLS LSPG (SEQ ID NO: 10) |
| C_L | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 11) |
| Heavy Chain | QVQLVQSGSEVKKPGASVKVSCKASGYTFTTYAMNWVRQAPGQGLEWMGWI NTNTGNPTYAQGFTGRFVFSLDTSVNTAYLQISSLKAEDTAVYYCARDFGGFDY WGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRV EPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCK VSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEA LHNHYTQKSLSLSPG (SEQ ID NO: 12) |
| Light Chain | AIQLTQSPSSLSASVGDRVTITCRASQGISSALAWYQQKPGKAPKLLINDASSLES GVPSRFSGSGSGTDFTLTISSLQPEDFATYYCQQFNNYPRTFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 13) |

The Ab was produced by recombinant methods in CHO cells and purified by Protein A affinity chromatography. The identity of the Ab was confirmed by SDS-PAGE, N-terminal sequencing, and mass spectrometry analysis. The purity of the Ab was >98% as tested by size exclusion chromatography (SEC). Special aggregation propensity (SAP) modeling studies performed on the CDR region of BMS-986215 showed a low SAP score indicating a very low aggregation propensity. A single N-glycosylation site was confirmed at N297 on the heavy chain (underlined in Table 3) with a glycan profile that contains G0F, G1F, and G2F structures as expected for human IgG1 molecules expressed in CHO cells. BMS-986215 showed high thermal and chemical stability. The thermal reversibility of this molecule at 78° C. is 41% which is higher than what is generally seen for a typical human IgG1 molecule. The biophysical characteristics of BMS-986215 are summarized in Table 4.

Example 3

Characterization of Binding Kinetics, Binding Affinity, Cross-Reactivity, Tissue Specificity, and Stability of BMS-986215

BMS-986215 Specifically Binds to Human and Cynomolgus CD27

Surface plasmon resonance (SPR) analysis confirmed the specific binding of BMS-986215 to hCD27. The apparent affinity ($K_D$) of the Ab to hCD27, measured using a Fab fragment of BMS-986215 and hCD27-mouseFc or hCD27-Histag proteins, was determined to be about 40 nM by SPR. The measured values were 41-44 nM at 37° C. and 13-16 nM at 25° C. The 3-fold loss of affinity from 25° C. to 37° C. was due to an increased dissociation rate while the association rate remained unchanged. The kinetic analysis used a 1:1 fit binding model. The $K_D$ was determined to be 0.045 nM by Scatchard analysis.

The $EC_{50}$ value for binding of BMS-986215 to human T cells was determined by flow cytometry to be 0.044 nM (range 0.022 to 0.076 nM, 0.044+/−0.011 nM, n=5). The $EC_{50}$ value for binding of BMS-986215 to cynomolgus T cells was determined by flow cytometry to be 0.131 nM (range 0.03569 to 0.2657, 0.131+/−0.069 nM, n=3), showing that BMS-986215 cross-reacts to cCD27.

TABLE 4

Biophysical Characteristics of BMS-986215

| Property | Method | Results |
|---|---|---|
| Identity | N-terminal Seq | LC: Confirmed by peptide mapping HC: Confirmed by peptide mapping |

TABLE 4-continued

Biophysical Characteristics of BMS-986215

| Property | Method | Results |
|---|---|---|
| | LC-MS | 143,653 Da (Deglycosylated Intact mass confirmed) |
| | | Deglycosylated, reduced and alkylated HC = 49,291 Da |
| | | Aglycosylated, reduced and alkylated LC = 23,480 Da |
| | | >99% coverage for Peptide map by mass spec |
| | LC-MS/MS peptide map | Heavy and light chain sequence confirmed. Glycosylation at heavy chain N297 confirmed. Heavy chain N-terminal glutamine to pyroglutamate confirmed. |
| Purity/Homogeneity | CE-SDS | 96.4% monomer, impurities include 2.2% HHL, 0.2% HL, 0.2% HH, 1.0% LC; Non-glycosylated heavy chain not detected |
| | SEC | 98.6% monomer, 1.4% aggregate |
| | SE-MALS | 98.4% (145.3 kDa), 1.34% (395.8 kDa), 0.22% (56.3 kDa) |
| | HIC-HPLC | 7.3% tailing shoulder |
| | CE (Glycans) | G0 = 0.16%, G0F = 72.57%, G1F = 21.76%, G2F = 1.43%, Man5 = 4.08%. Glycan attachment at N297 on heavy chain. |
| | cIEF | 4 Isoforms (Major 8.83; Minor 8.64, 8.7, 8.92) |
| Chemical Modifications | LC-MS/MS peptide map | No major unexpected chemical modifications observed. |
| Thermal Stability and Reversibility | DSC (diluted into storage buffer) | Tm1 = 71° C., Tm2 = 79° C., Tm3 = 80° C. Reversibility at 78° C. = 41.5% |
| Physical Stability | Denaturation Gdn-HCl, intrinsic fluorescence | Unfolding Midpoint $C_{50}$ = 3.24M, |

Figure 1B:
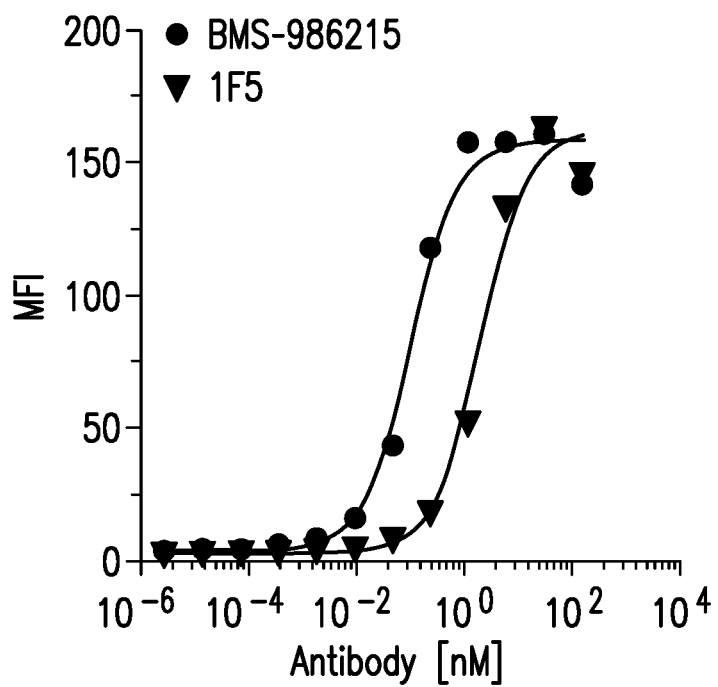
Figure 2A:
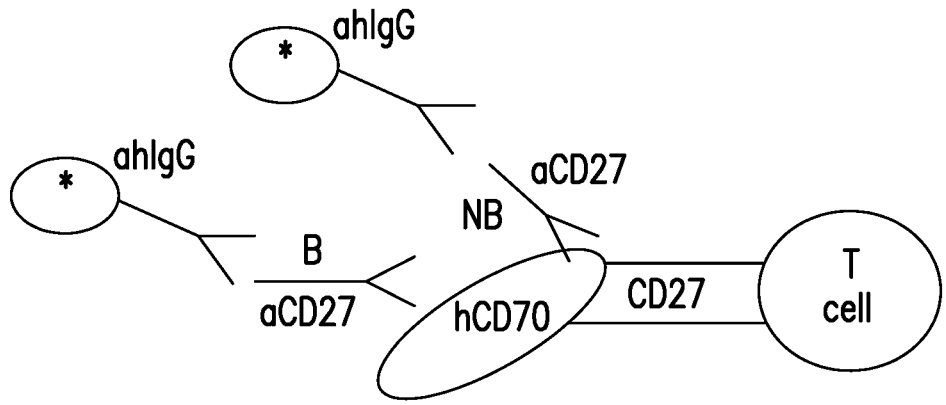
FIGS. 2(A)-(B) show that BMS-986215 is a non-ligand blocking anti-CD27 mAb. (A) shows an illustration of a flow cytometry assay of human T cells pretreated with 10 μg/ml human CD70 (hCD70), the ligand of CD27, followed by treatment with ligand blocking (B) or non-blocking (NB) anti-CD27 Abs (aCD27). Binding of the Abs in the assay was detected by a labeled anti-human IgG Ab (*, ahIgG). (B) shows a graph in which the assay of (A) was conducted with BMS-986215, ligand blocking 1F5, and human IgG1 (control) Abs. Binding of BMS-986215 was detected, indicating that CD70 binding to CD27 does not block binding of BMS-986215. Binding of the ligand blocking 1F5 Ab was not detected. (C) shows an illustration of a flow cytometry assay in which human T cells were exposed to Abs as described for (A) in the presence of 10 μg/ml soluble human CD70. CD70 was detected by a labeled anti-CD70 Ab (*, aCD70). (D) shows a graph in which the assay of (C) was conducted with BMS-986215, ligand blocking 1F5, and human IgG1 (control) Abs. CD70 remained detectable in the presence of increasing concentrations of BMS-986215, indicating that CD70 binding was not blocked by BMS-986215. Binding of CD70 decreased with increasing concentrations of the ligand blocking 1F5 Ab. "MFI," "hIgG1," and "FL2" are as described for FIG. 1. "FL1" in (B) indicates measurement in fluorescence channel 1 (FL1).
Figure 2B:
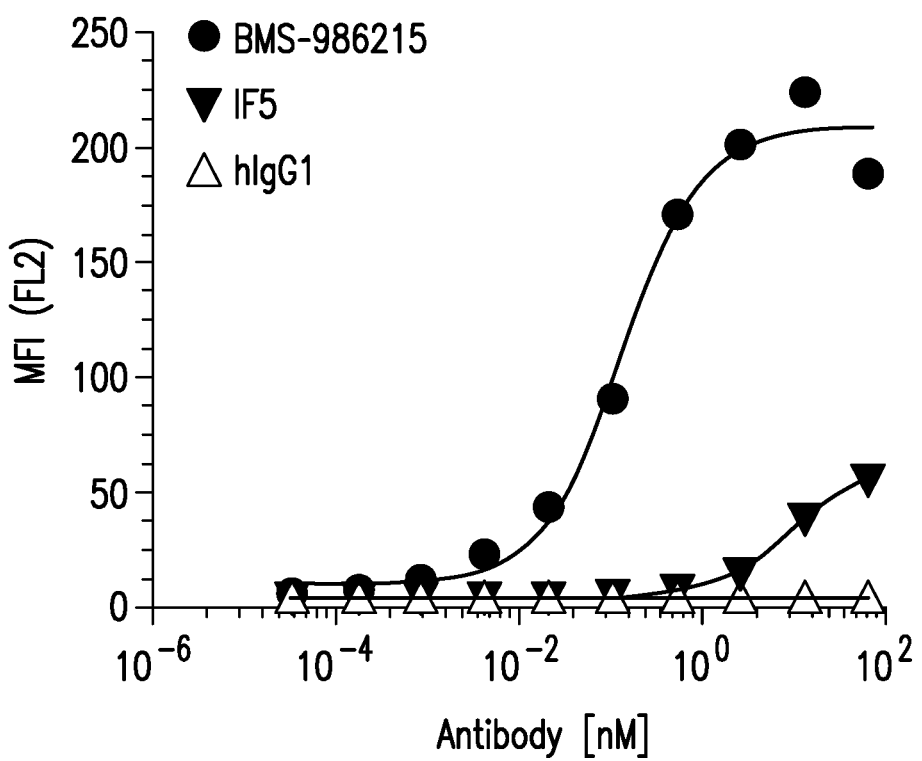

Flow cytometry analysis also showed that BMS-986215 has a higher affinity for h- and cCD27 as compared to 1F5, a human anti-hCD27 reference mAb. See FIGS. 1A and 1B, respectively. The amino acid sequences for the heavy chain and light chain for HuMAb 1F5 are shown in Table 5. The $EC_{50}$ values in FIG. 1A for binding of BMS-986215 and 1F5 to human T cells were 0.02210 nM and 1.088 nM, respectively. The $EC_{50}$ values as determined for the binding of BMS-986215 and 1F5 to cynomolgus T cells in FIG. 1B are 0.092 nM and 1.800 nM, respectively.

consistent with this mAb being a ligand non-blocking Ab. See FIGS. 2B and 2D. For example, a flow cytometry analysis was conducted using human T cells pretreated with 10 μg/ml soluble human CD70, the ligand of CD27, followed by treatment with BMS-986215, 1F5, and human IgG1 (control) Abs. The presence or absence of binding of the Abs was detected using a labeled anti-human IgG Ab. Binding of BMS-986215 was detected, indicating that CD70 binding to CD27 does not block binding of BMS-986215. See FIG. 2A, showing a schematic of the assay, and FIG. 2B,

TABLE 5

Amino Acid Sequences for the Heavy and Light Chains in Reference HuMAb 1F5

Amino Acid Sequences and SEQ ID NOs.

| | |
|---|---|
| Heavy Chain | QVQLVESGGGVVQPGRSLRLSCAASGFTFSSYDMHWVRQAPGKGLEWVAVIW YDGSNKYYADSVKGRFTISRDNSKNTLYLQMNSLRAEDTAVYYCARGSGNWG FFDYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVF SCSVMHEALHNHYTQKSLSLSPGKGSS (SEQ ID NO: 20) |
| Light Chain | DIQMTQSPSSLSASVGDRVTITCRASQGISRWLAWYQQKPEKAPKSLIYAASSL QSGVPSRFSGSGSGTDFTLTISSLQPEDFATYYCQQYNTYPRTFGQGTKVEIKRT VAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 21) |

BMS-986215 is a Non-Ligand Blocking MAb

Figure 2C:
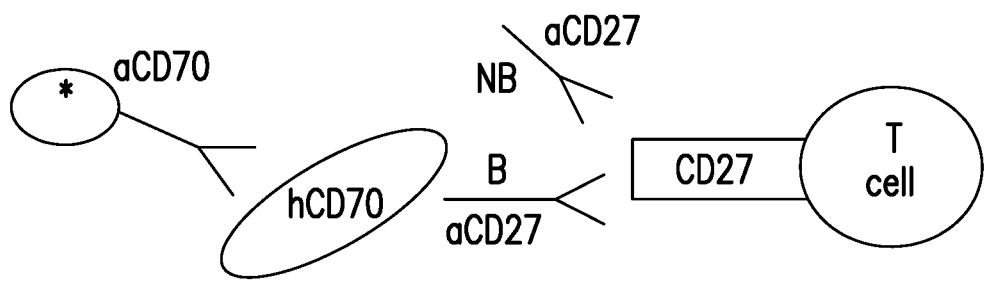
Figure 2D:
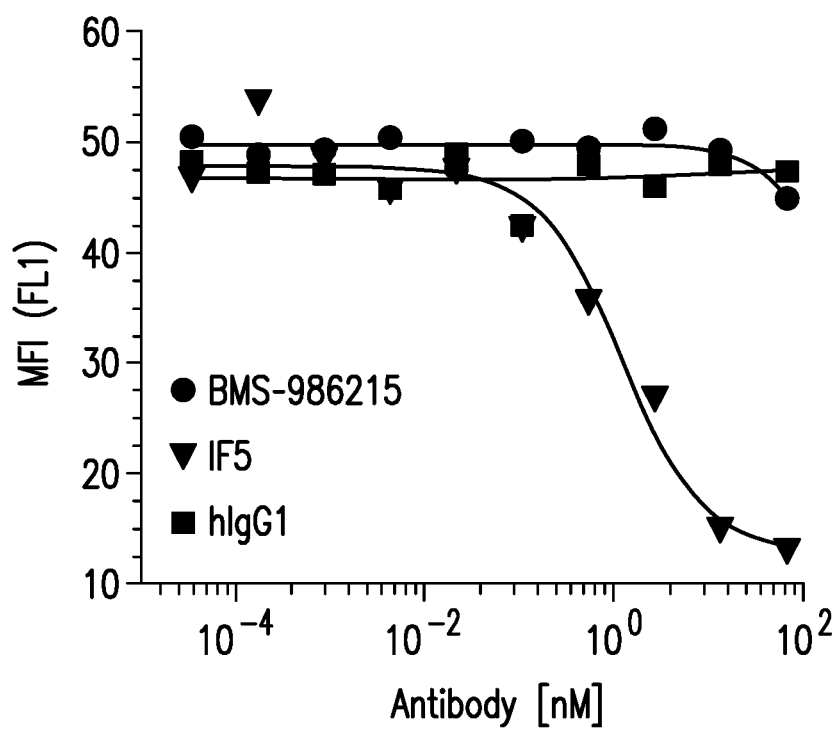

No inhibition of CD70 binding to CD27 by BMS-986215 or the converse was detected by SPR or flow cytometry, showing a graph of the results. Binding of the ligand blocking 1F5 Ab was not detected. Id. Another flow cytometry analysis was conducted in which human T cells were exposed to BMS-986215, 1F5, and human IgG1 (control) Abs in the presence of 10 μg/ml soluble human CD70. CD70 was detected by a labeled anti-CD70 Ab. CD70 remained detectable in the presence of increasing concentrations of BMS-986215, indicating that CD70 binding was not blocked by BMS-986215. See FIG. 2C, showing a schematic of the assay, and FIG. 2D, showing a graph of the results. Binding of CD70 decreased with increasing concentrations of the ligand blocking Ab 1F5. Id.

Tissue Specificity

In preliminary tissue cross-reactivity evaluations, fluorescein isothiocyanate (FITC)-conjugated BMS-986215 (research grade) was applied to frozen sections from 22 normal human tissues (1 or 2 donors of each). As expected, specific staining was observed in subsets of mononuclear cells (MNC) in the thymus, tonsil, and spleen, in lymphoid-rich tissues (colon, small intestine, and stomach), and rarely in other tissues (thyroid, lung, skin, uterus, prostate, liver, kidney, pancreas, adrenal, pituitary, placenta, and testis) (data not shown). In general, positive cells correlated with background inflammatory lesions. The largest number of positive-staining cells was in tonsil, thymus, and small intestine. Positive-staining lymphocytes were concentrated in the medulla of the thymus and the T cell rich regions in the tonsil (inter-follicular region) and spleen (peri-follicular-like/marginal zone and PALS). In the small intestine, positive cells were primarily distributed in the basal lamina propria and focal lymphoid aggregates/follicles. The cerebrum, cerebellum, heart, and peripheral nerve were negative.

Example 4

Epitope Mapping of BMS-986215

Figures 3A, 3B:
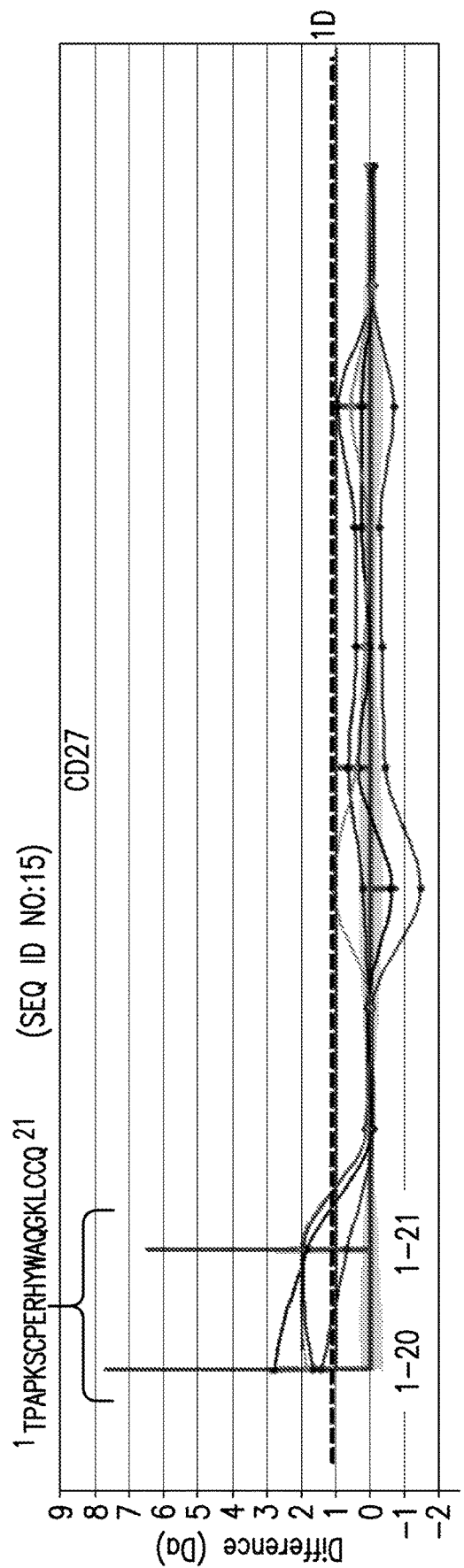
FIGS. 3(A)-(C) show BMS-986215 epitope mapping. (A) shows the sequence coverage for CD27 obtained from hydrogen/deuterium exchange mass spectrometry (HDX-MS) and fast photochemical oxidation of proteins (FPOP) epitope mapping methods. The sequence shown is the mature CD27 protein without the 20 amino acid signal peptide sequence of SEQ ID NO:1. Amino acids 1 to 172 in (A) correspond to amino acids 21 to 192 of SEQ ID NO:1. (B) shows HDX-MS data analysis indicating that the N-terminal region of CD27 (corresponding to amino acids 21-41 of SEQ ID NO:1) showed significant protection upon BMS-986215 binding. (C) shows FPOP relative protection percentages for four peptides of CD27, with amino acids 32-37 of the mature protein (corresponding to amino acids 52-57 of SEQ ID NO:1) having the highest FPOP protection percentage (75%) and indicating a binding epitope on CD27 upon interactions with Fab.

Hydrogen/deuterium exchange mass spectrometry (HDX-MS) and fast photochemical oxidation of proteins (FPOP) methods were utilized to probe regions of CD27 to which BMS-986215 binds. HDX-MS experiments on CD27/BMS-986215 provided 62% sequence coverage, including the N- and C-terminal regions of CD27. FPOP measurements yielded 81% sequence coverage on CD27, including the mid-region of CD27. The total sequence coverage for CD27 was 98% with the combined HDX-MS and FPOP dataset. See FIG. 3(A). The sequence shown in FIG. 3(A) is that of the mature CD27 protein without the signal peptide sequence of amino acids 1-20 of SEQ ID NO:1. Amino acids 1 to 172 in FIG. 3(A) correspond to amino acids 21 to 192 of SEQ ID NO:1.

HDX-MS

Prior to epitope mapping experiments, non-deuterated experiments were carried out to generate a list of common peptides for recombinant full length hCD27-His tag (10 μM) and protein complex of CD27 and BMS-986215 (1:1 molar ratio). In the HDX-MS experiment, 5 μL of each sample (CD27 or CD27 with BMS-986215) were diluted into 20 μL of $D_2O$ buffer (10 mM phosphate buffer, $D_2O$, pD 7.0) to start the labeling reactions. The reactions were carried out for different periods of time: 20 sec, 1 min, 10 min and 240 min. By the end of each labeling reaction period, the reaction was quenched by adding quenching buffer (100 mM phosphate buffer with 4M GdnCl and 0.4M TCEP, pH 2.5, 1:1, v/v). 1 μL of pepsin/protease XIII (1:1, v/v at 1 mg/mL) was added and the proteins were digested for 3 min on ice. The digested solution was injected into a Waters HDX-MS system (Waters Corporation, Milford, MA) for analysis. The deuterium uptake levels of common peptic peptides were monitored in the absence or presence of BMS-986215.

The HDX-MS data analysis on BMS-986215 in CD27 indicates that BMS-986215 binds to an epitope comprising a region at the N-terminus of CD27: TPAPKSCPERHYWAQGKLCCQ (SEQ ID NO:15, corresponding to amino acids 1 to 21 of the mature protein or amino acids 21 to 41 of SEQ ID NO:1).

FPOP

FPOP experiments were performed on CD27 and CD27/Fab of BMS-986215 complex (1:1 molar ratio, 7.5 μM final concentration). A KrF excimer laser was used to generate hydroxyl radicals by the photolysis of $H_2O_2$, and the excitation wavelength was set at 248 nm. Immediate before labeling, 5 μL of histidine and $H_2O_2$ each were added to a protein aliquot. The final volume of protein solution was 50 μL, and the final concentrations of histidine, and $H_2O_2$ were 500 μM and 15 mM, respectively. The laser energy was adjusted to 28 mJ/pulse (7.4 Hz). Both FPOP and no-laser control experiments were performed in duplicates. Each replicate was collected in a micro-centrifuge tube containing 11 μL of quenching solution (800 nM of catalase tetramer and 200 mM of methionine). The samples were denatured, reduced, alkylated and digested with trypsin. Data acquisition was performed on a Thermo Q Exactive Plus mass spectrometer (Thermo Fisher Scientific, Waltham, MA) with a Waters Acquity UPLC system (Waters Corporation). The Byonic™ search engine (Proten Metrics, San Carlos, CA) was used to provide sequencing coverage and identify oxidation sites. Relative oxidation levels for tryptic peptides were calculated manually for each replicate. Only peptides with statistically significant difference in relative oxidation between free and bound state (based on student T-test, p value<0.05) were considered for further analysis.

Figure 3C:
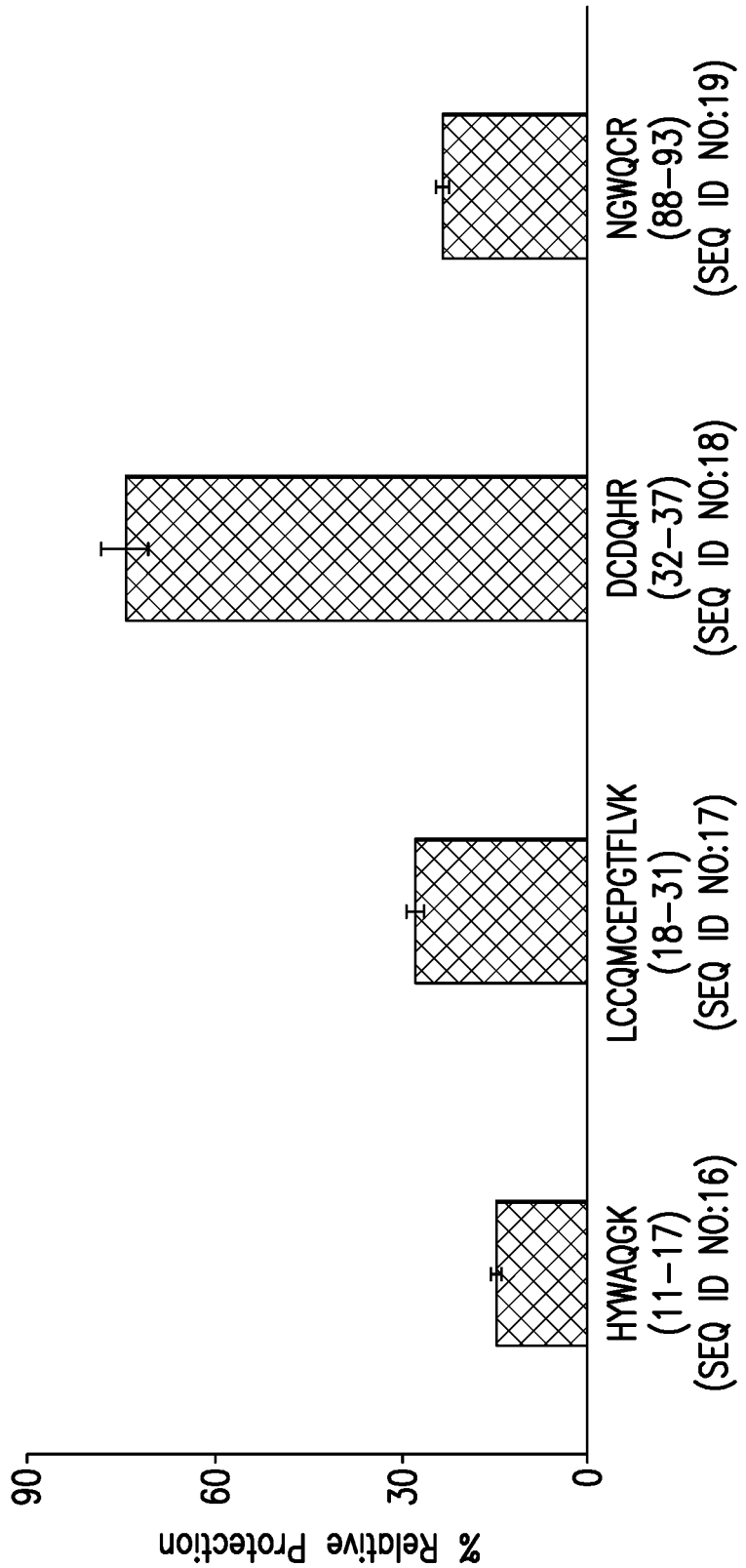

In the FPOP experiments, four CD27 peptides exhibited significant differences in oxidation levels: HYWAQGK (SEQ ID NO:16, corresponding to amino acids 11 to 17 of the mature protein or amino acids 31 to 37 of SEQ ID NO:1), LCCQMCEPGTFLVK (SEQ ID NO:17, corresponding to amino acids 18 to 31 of the mature protein or amino acids 38 to 51 of SEQ ID NO:1), DCDQHR (SEQ ID NO:18, corresponding to amino acids 32 to 37 of the mature protein or amino acids 52 to 57 of SEQ ID NO:1), and NGWQCR (SEQ ID NO:19, corresponding to amino acids 88 to 93 of the mature protein or amino acids 108 to 113 of SEQ ID NO:1). FPOP protection percentage upon binding of Fab was calculated as (Relative % FPOP difference in CD27−Relative % FPOP difference in Fab)/(Relative % FPOP in difference in CD27)×100. FIG. 3(C) shows FPOP protection percentages for these four peptides. The DCDQHR peptide was shown to have the highest FPOP protection percentage (75%), indicating a binding epitope on CD27 upon interactions with the BMS-986215 Fab.

Based on the above HDX-MS and FPOP experiments, the CD27 epitope to which BMS-986215 binds is considered to comprise two discontinuous binding regions, TPAPKSCPERHYWAQGKLCCQ (SEQ ID NO:15) and DCDQHR (SEQ ID NO:18), corresponding to amino acids 21 to 41 and 52 to 57 of SEQ ID NO:1.

Example 5

CD27 Agonism by BMS-986215 Increases Activation of T Cells

Figure 4A:
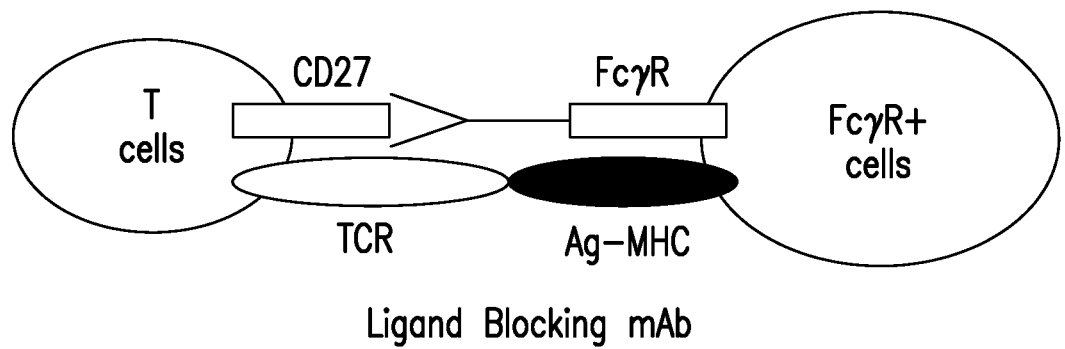
FIGS. 4(A)-(B) show illustrations of the effects of a ligand blocking anti-CD27 Ab (A) and the ligand-nonblocking Ab, BMS-986215 (B), in terms of their interactions with Fc gamma receptor (FcγR) and CD27 stimulation of T cells. CD27 co-stimulation of T cells by binding to its ligand CD70 occurs in the presence of BMS-986215 (B), but not in the presence of ligand blocking Abs (A).
Figure 4B:
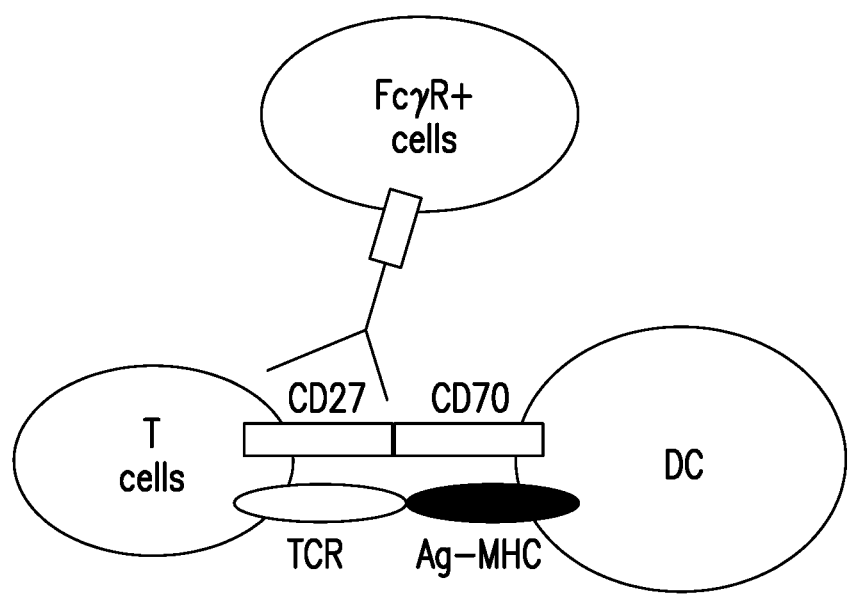

Anti-CD27 mAb agonists require FcγR interaction (i.e., cross-linking) for activity. There is no CD27-costimulation of T cells in the presence of a ligand blocking mAb (such as 1F5) without FcγR+ cells. See FIG. 4(A). However, BMS- 986215 mAb is a non-ligand blocking mAb, and biological assays were conducted to determine its activities. In contrast to ligand blocking mAbs such as 1F5, the data show that BMS-986215 was able to co-stimulate T cells without FcγR engagement in the presence of CD70. See FIG. 4(B).

BMS-986215 Enhances NF-κB and MAPK Signaling

A primary T cell signaling assay was conducted to observe the effect of BMS-986215 on induction of NF-κB and MAPK signaling in naïve and pre-activated human T cells stimulated by anti-CD3 plus anti-CD28 Abs. Briefly, human CD4+ T cells were stimulated with anti-CD3 and anti-CD28 Abs for 24 h. Cells were seeded at 10,000 cells/well of a 384-well plate and starved for 2 h before adding Abs. Cells were then treated with BMS-986215, 1F5, or hIgG1 (control) Abs combined with cross-linkers in a dose/time course and analyzed for NF-κB and MAPK signaling.

Figure 5A:
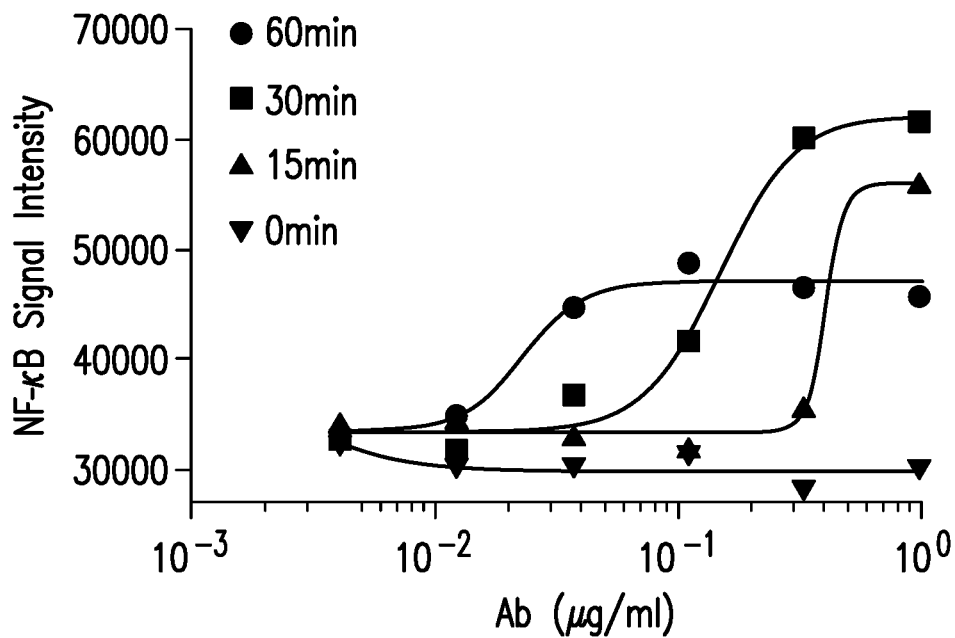
FIGS. 5(A)-(C) show that BMS-986215 results in a greater induction of NF-κB signaling in a primary T cell signaling assay as compared to 1F5. Graphs show NF-κB signal intensity based on treatment times of 0, 15, 30, and 60 minutes with indicated amounts (µg/ml) of BMS-986215 (A), 1F5 (B), and IgG1 control (C) Abs.
Figure 5B:
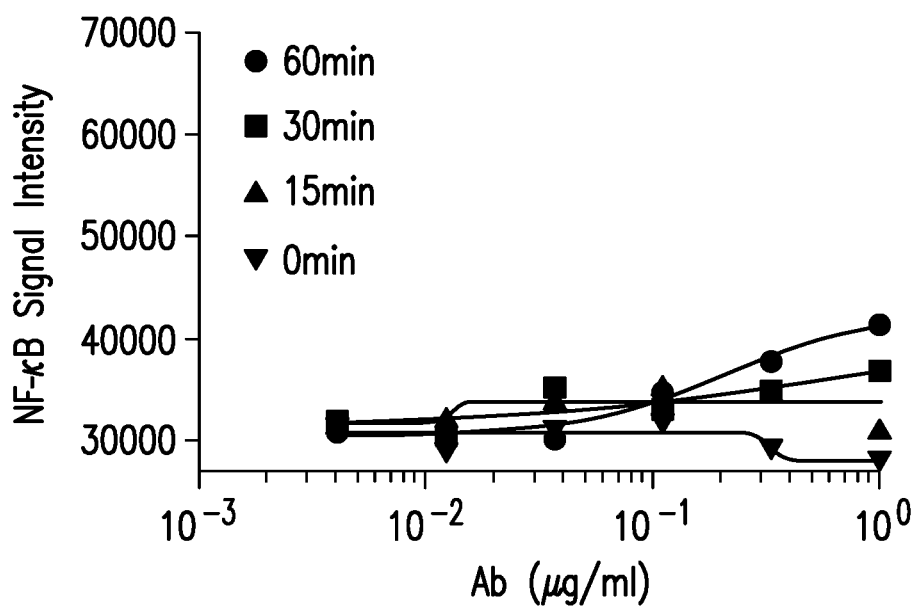
Figure 5C:
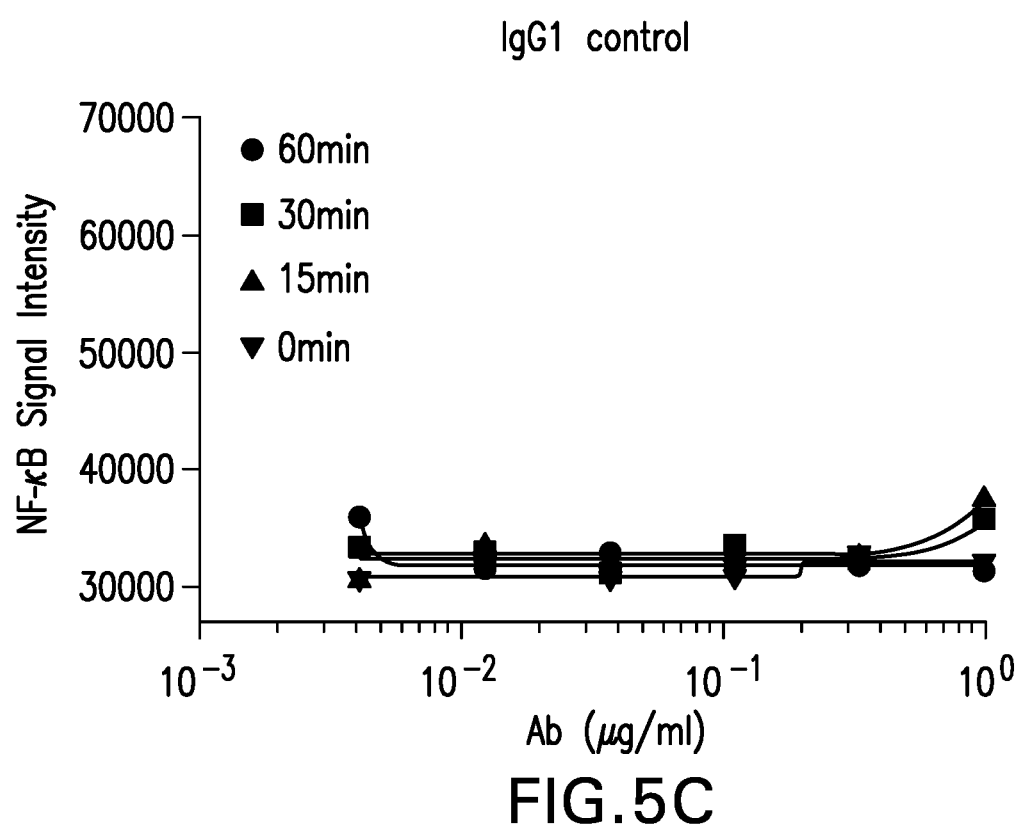

BMS-986215 was observed to induce NF-κB and MAPK signaling with an $EC_{50}$ of 0.02 nM to 0.23 nM. FIGS. 5(A)-(C), for example, show NF-κB signal intensity resulting from the treatment with the Abs and greater induction of NF-κB by BMS-986215 as compared to 1F5.

BMS-986215 Enhances T Cell Proliferation and IFN-γ Secretion

Co-cultures of CD4+ T cells and CHO-svCD3-CD32a cells were used to assay the effect of BMS-986215 on T cell proliferation and IFN-γ secretion. Briefly, human CD4+ T cells from healthy donor blood samples were co-cultured with CHO-svCD3-CD32a cells (CHO cells that express a single-chain anti-CD3 scFv Ab derived from the anti-CD3 OKT3 mAb and hCD32a-131His (Fc γ RIIa)). The co-cultures were treated with BMS-986215, 1F5, or hIgG1 (control) Abs, and analyzed for T cell proliferation and IFN-γ secretion.

Figure 6A:
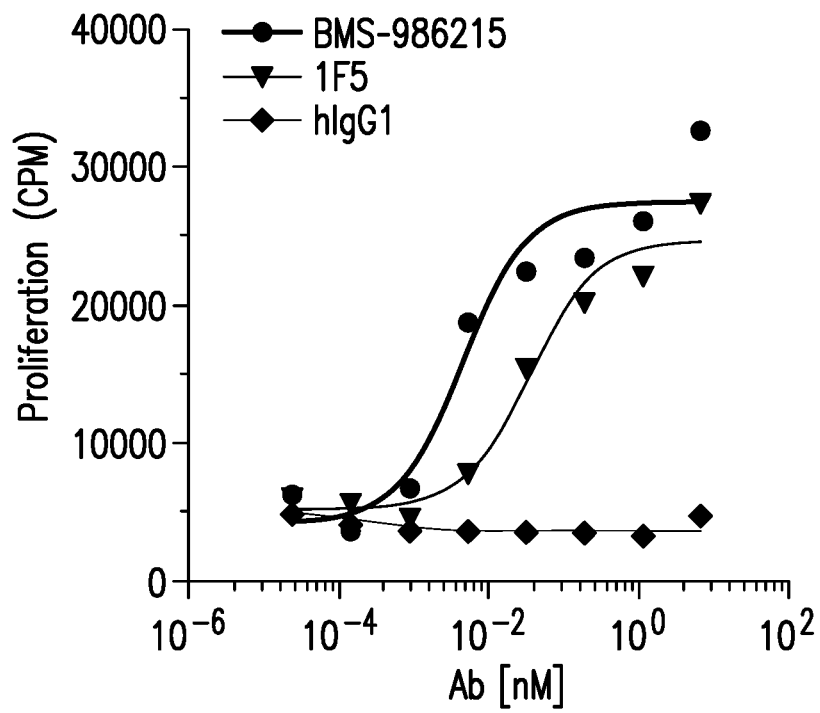
FIGS. 6(A)-(B) show that BMS-986215 results in a greater induction of T cell proliferation and IFN-g secretion in co-cultures of CD4$^+$ T cells and CHO-scCD3-CD32a cells (CHO cells that express a single-chain anti-CD3 scFv Ab derived from the anti-CD3 OKT3 mAb and hCD32a-131His (Fc γ RIIa)) as compared to 1F5. Co-cultures were treated with BMS-986215, 1F5, or hIgG1 (control) Abs in concentrations (nM) indicated in the graphs. (A) shows proliferation of T cells in counts per minute (CPM) and (B) shows amounts of IFN-γ in picograms per milliliter (pg/ml) secreted from T cells following treatment.
Figure 6B:
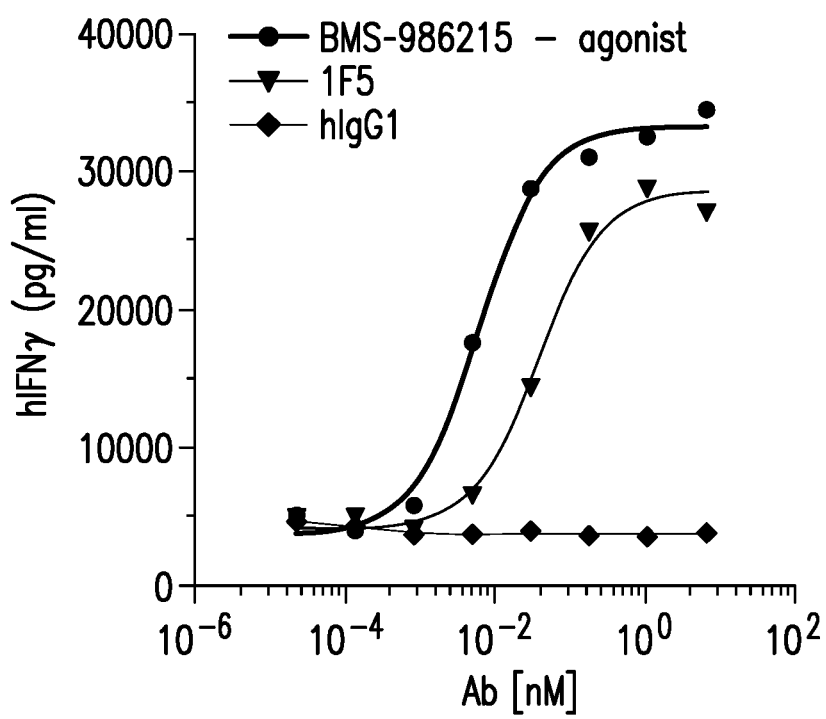
Figure 7A:
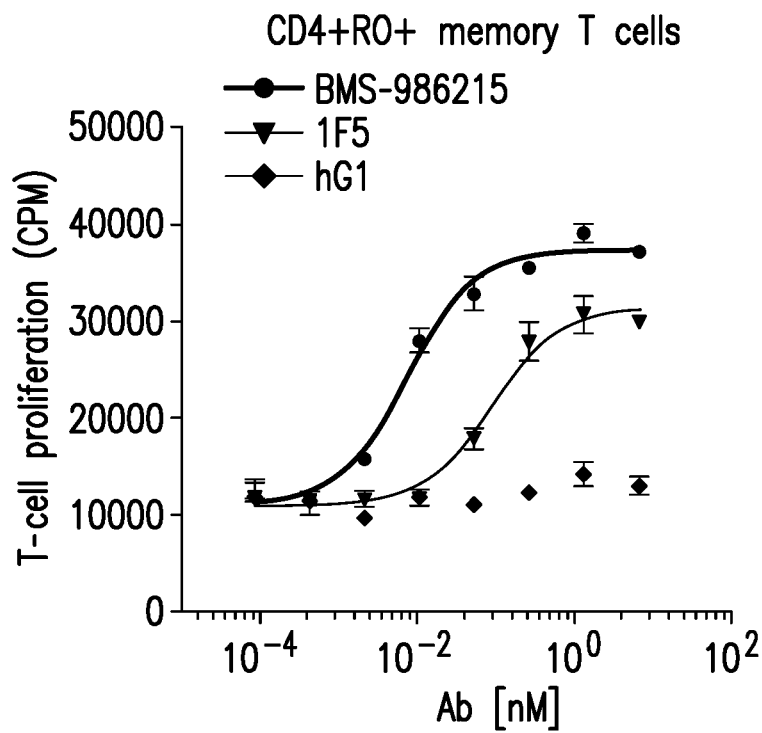
FIGS. 7(A)-(D) show that BMS-986215 results in a greater induction of T cell proliferation and IFN-γ secretion in co-cultures of CHO-scCD3-CD32a cells and either CD4$^+$CD45RO$^+$ memory T cells ((A)-(B)) or CD4$^+$CD45RA$^+$ naïve T cells ((C)-(D)) as compared to 1F5, with T-cell proliferation, amounts of IFN-γ, and Abs as described for FIG. 6.
Figure 7B:
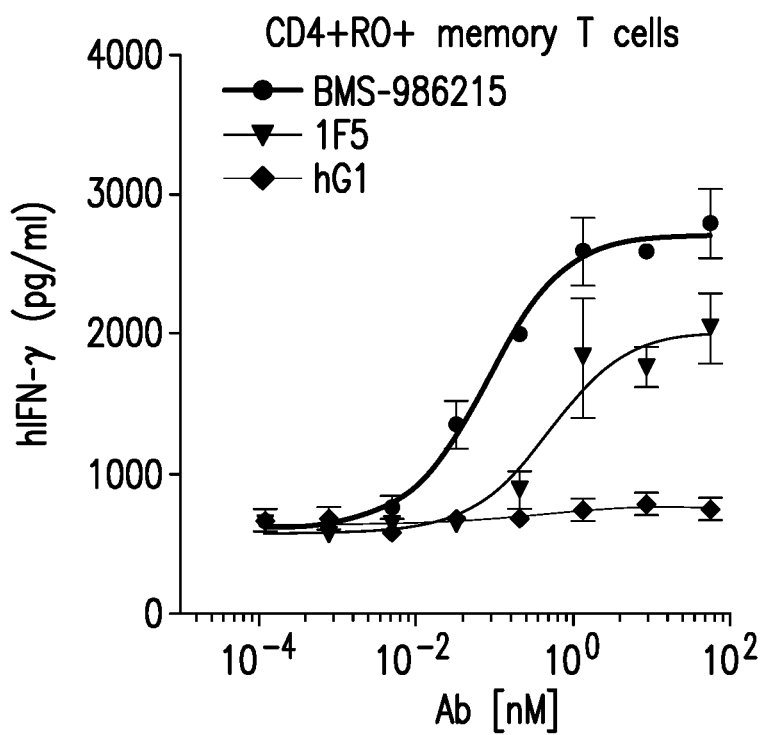
Figure 7C:
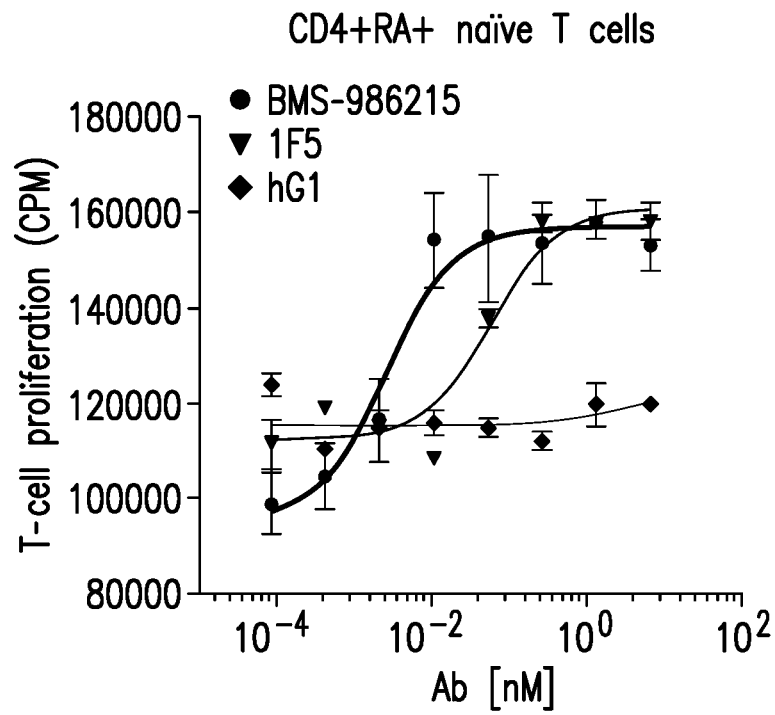
Figure 7D:
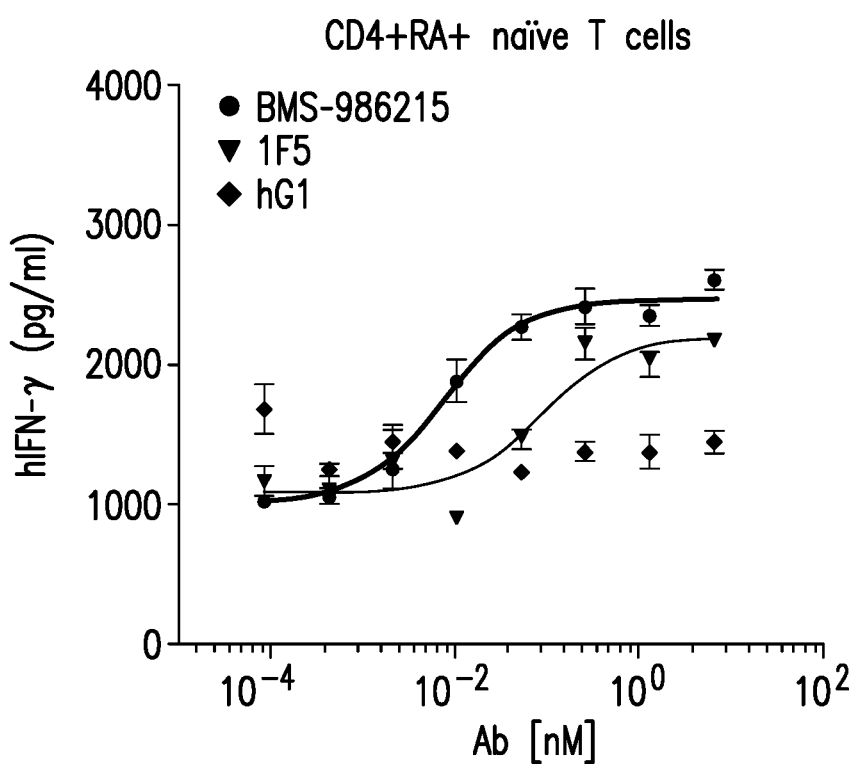

BMS-986215 was observed to co-stimulate T cells, resulting in enhanced proliferation and IFN-γ secretion with an $EC_{50}$ of 0.001 nM to 0.028 nM. Mean $EC_{50}$ values for BMS-986215 were 0.009 nM and 0.0078 nM for proliferation and IFN-γ secretion, respectively. FIGS. 6(A)-(B), for example, show a generally much greater induction of proliferation and IFN-γ secretion, respectively, by BMS-986215 compared to 1F5. The $EC_{50}$ values associated with T cell proliferation in FIG. 6(A) were 0.004503 nM and 0.03566 nM for BMS-986215 and 1F5, respectively. The $EC_{50}$ values associated with IFN-γ secretion in FIG. 6(B) were 0.006235 nM and 0.04017 nM for BMS-986215 and 1F5, respectively.

Assays were also conducted using co-cultures of CD4+CD45RO+ memory T cells or CD4+CD45RA+ naïve T cells with CHO-svCD3-CD32a cells. The co-cultures were treated with BMS-986215, 1F5, or hIgG1 (control) Abs, and analyzed for T cell proliferation and IFN-γ secretion. Results are shown in FIG. 7, with BMS-986215 resulting in much higher levels of T-cell proliferation and IFN-γ secretion than 1F5. For example, BMS-986215 induced proliferation of CD4+CD45RO+ memory T cells and IFN-γ production, with $EC_{50}$ values of 0.005 nM and 0.015 nM, respectively, compared to $EC_{50}$ values of 0.073 nM and 0.089 nM, respectively, for 1F5).

Figure 8:
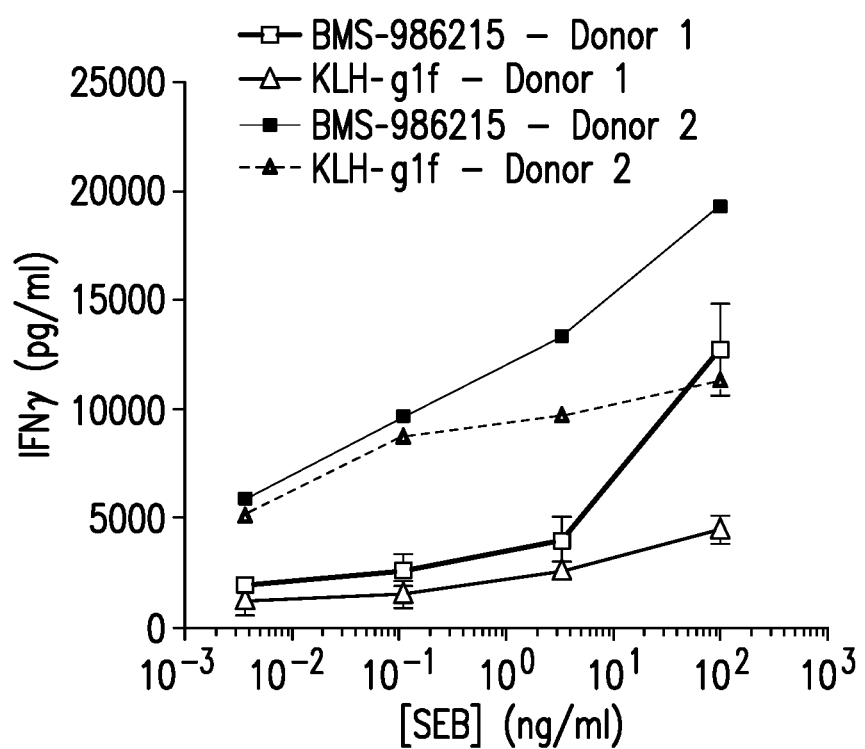
FIG. 8 shows that BMS-986215 results in an average fold-induction of greater than 2.5 for IFN-γ secretion (pg/ml) from CD4$^+$CD25$^-$ T cells from different donors (Donor 1 and Donor 2) that have been co-cultured with B cells and stimulated by varying amounts (ng/ml) of Staphylococcal enterotoxin B (SEB). The stimulated co-cultures were treated with either BMS-986215 or an anti-Keyhole limpet hemocyanin Ab, g1F glycoform (KLH-g1f).
Figure 9A:
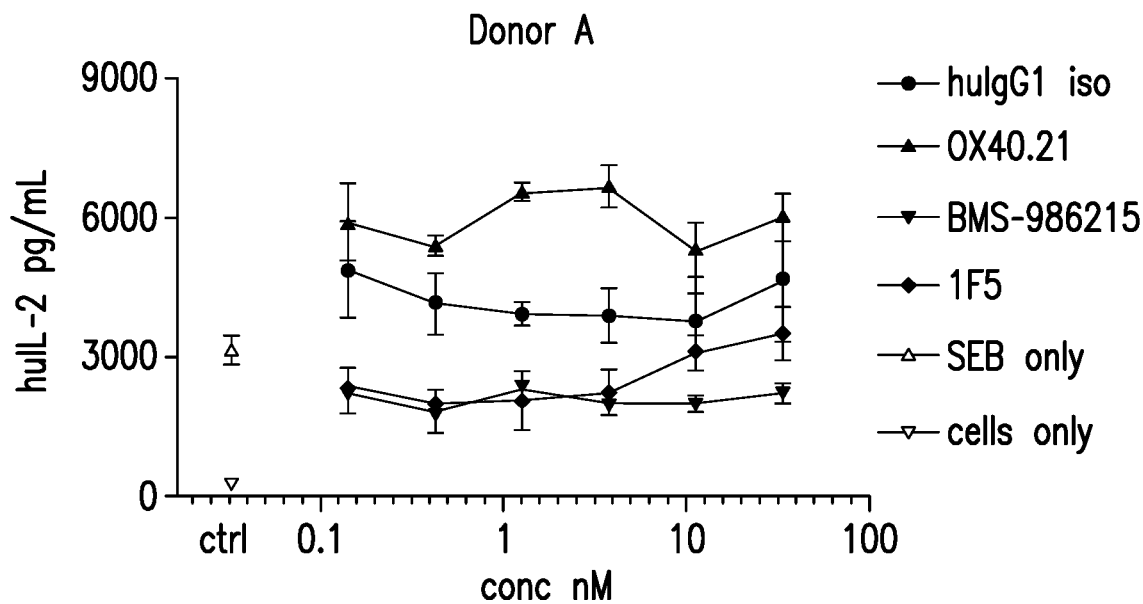
FIGS. 9(A)-(E) show that interleukin-2 (IL-2) release was increased from SEB-stimulated human PBMCs in the presence of soluble crosslinked BMS-986215 as compared to the control without BMS-986215. PBMCs from three donors (Donors A, B, and C) stimulated by SEB were treated with soluble anti-human IgG1 (hIgG1, control), anti-human OX40 (OX40.21), 1F5, or BMS-986215 Abs at the noted concentrations (nM) in the absence (FIGS. 9(A) and (C)) or presence (FIGS. 9(B), (D), and (E)) of a cross-linker (anti-human Fcγ Ab). PBMCs without SEB or Ab treatments (cells only) and PBMCs treated with SEB but not Abs (SEB only) were controls.
Figure 9B:
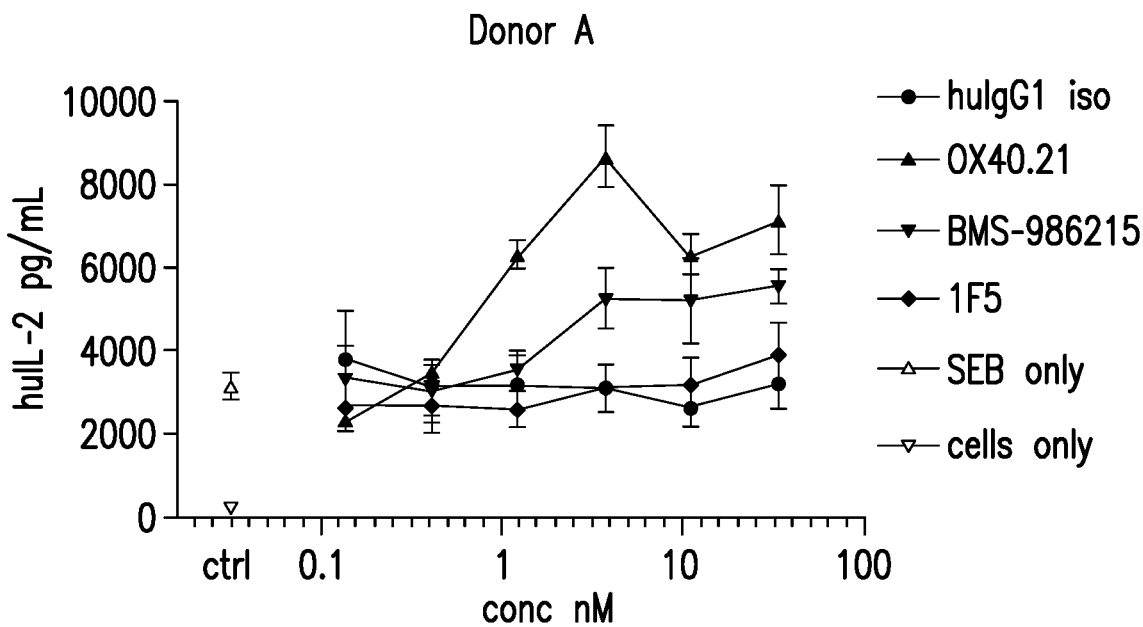
Figure 9C:
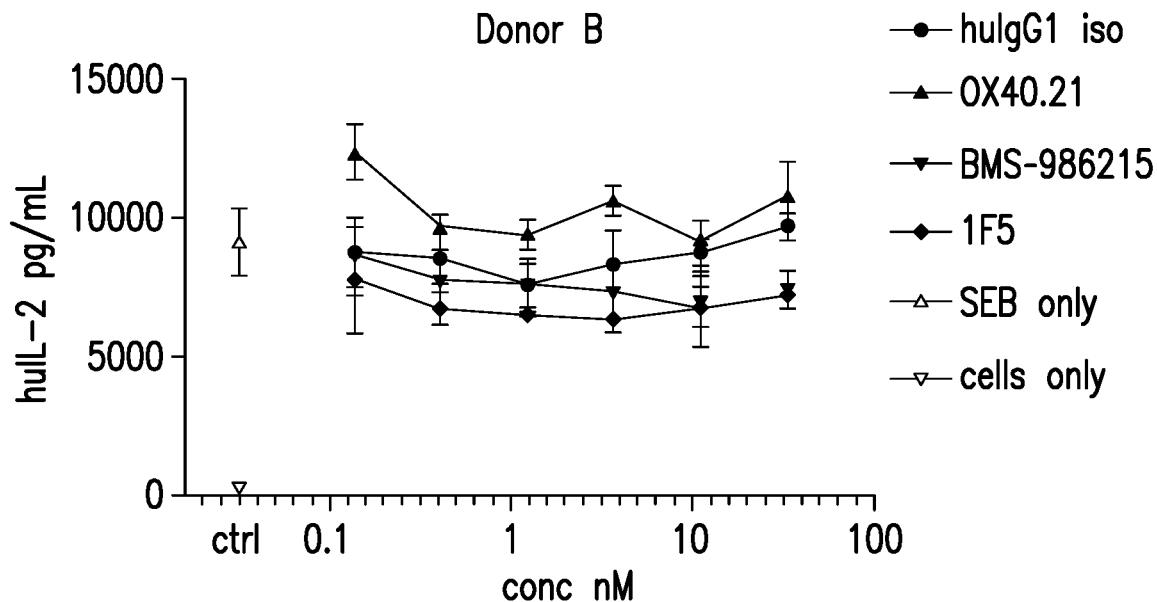
Figure 9D:
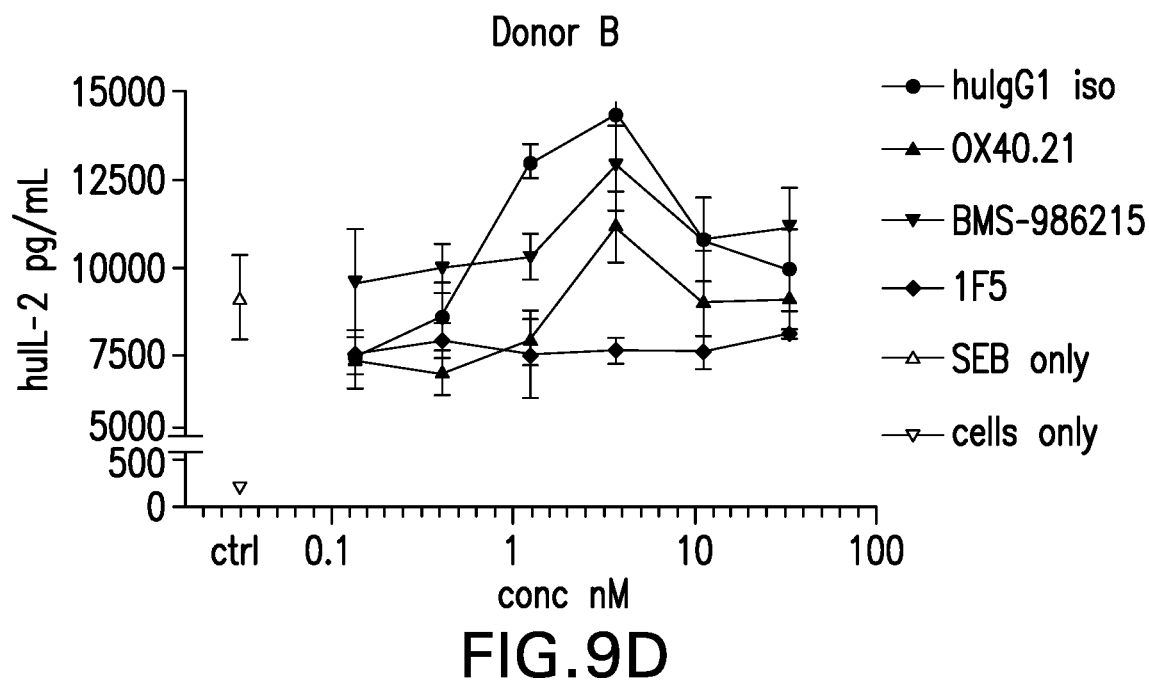
Figure 9E:
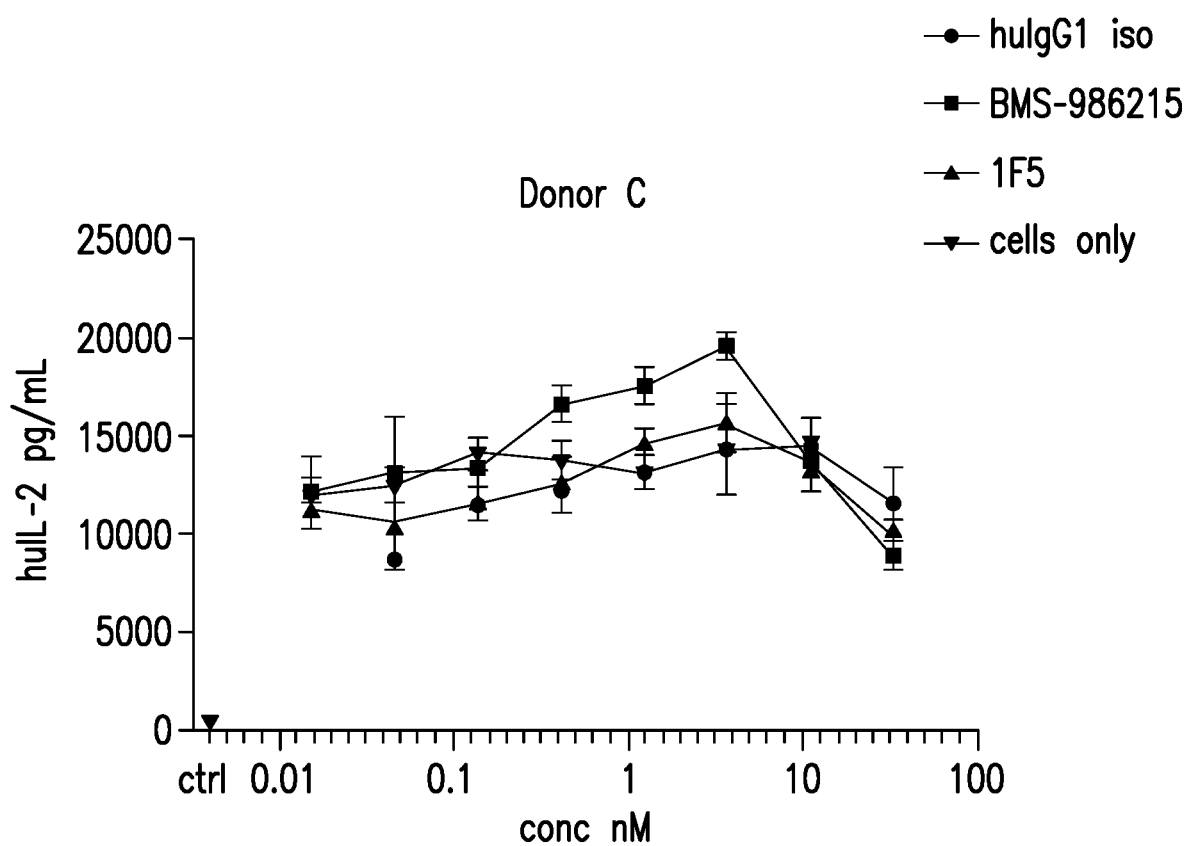
Figure 10A:
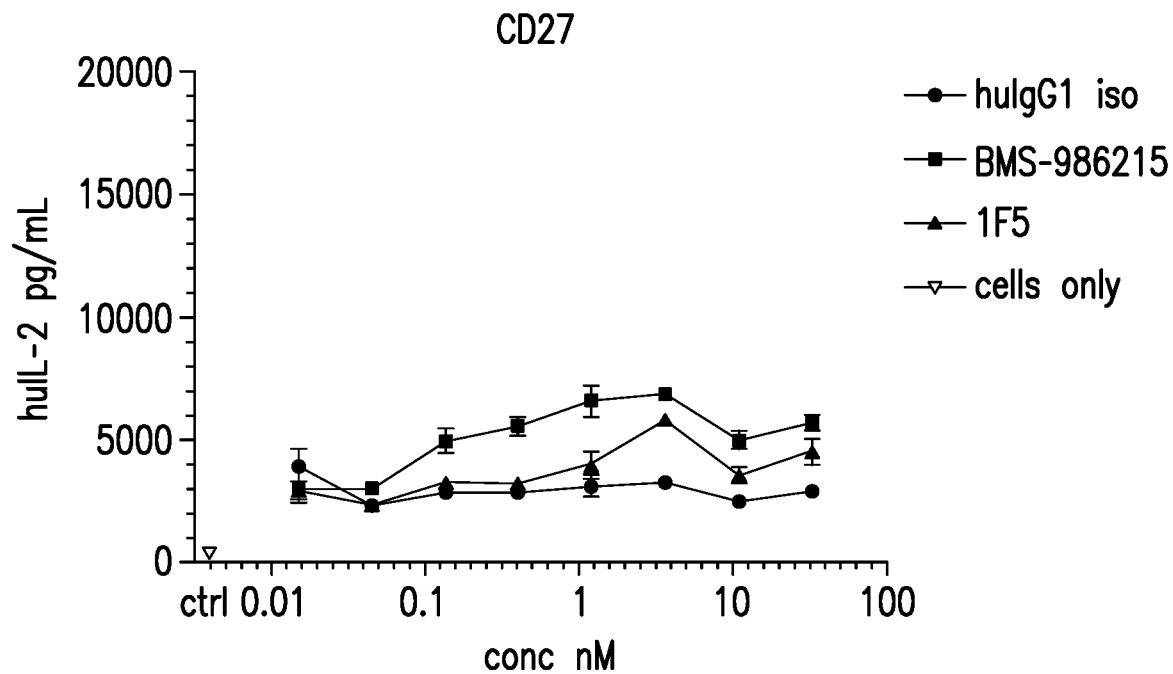
FIGS. 10(A)-(F) show that BMS-986215 acts synergistically with nivolumab and ipilimumab to improve IL-2 production in T-cell stimulation with SEB. PBMCs from two donors (Donors A and B) stimulated by SEB were treated with soluble anti-human IgG1 (hIgG1, control), 1F5, or BMS-986215 Abs at the noted concentrations (nM) alone (CD27) or with either nivolumab (Nivo combo) or ipilimumab (Ipi combo).
Figure 10B:
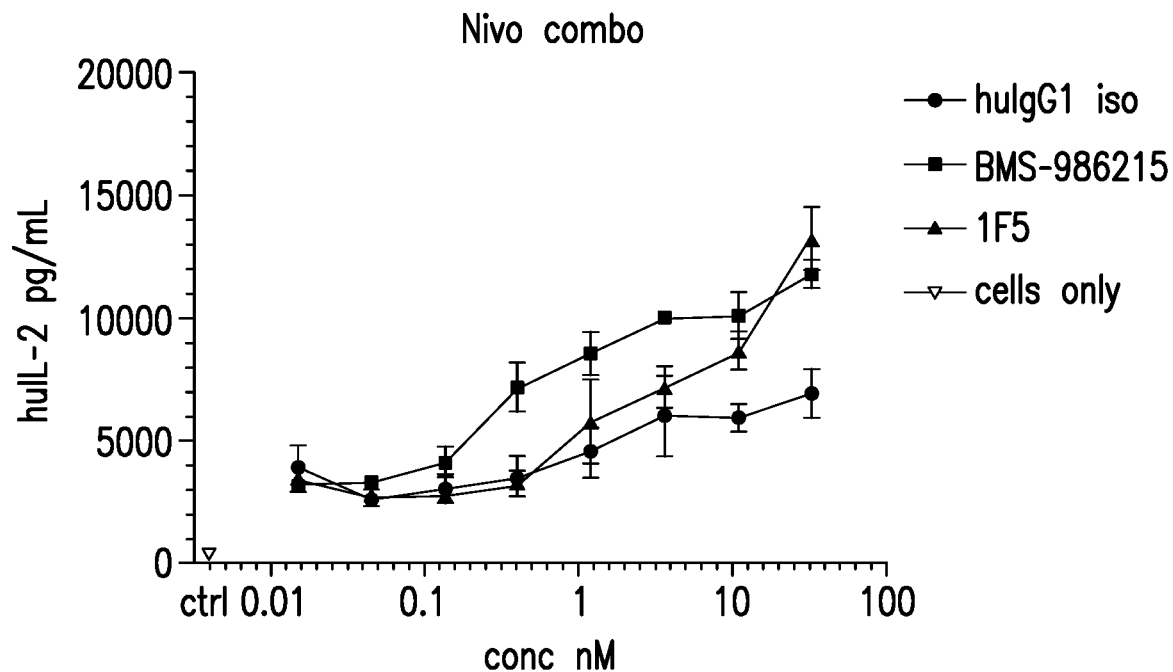
Figure 10C:
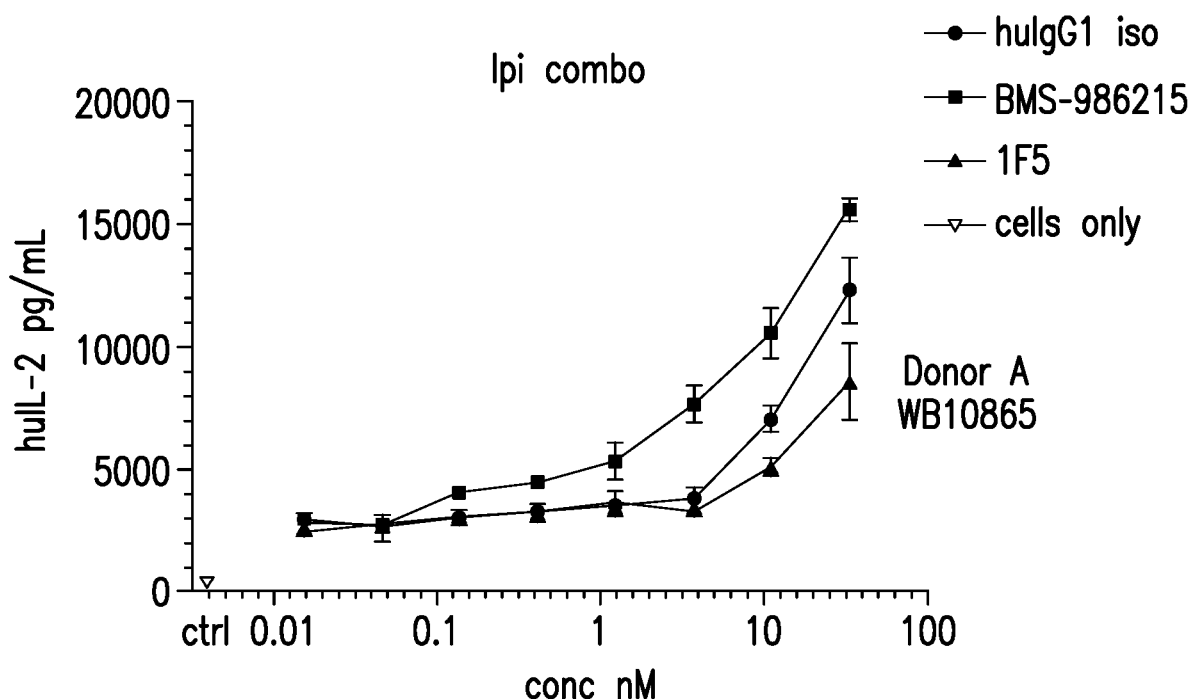
Figure 10D:
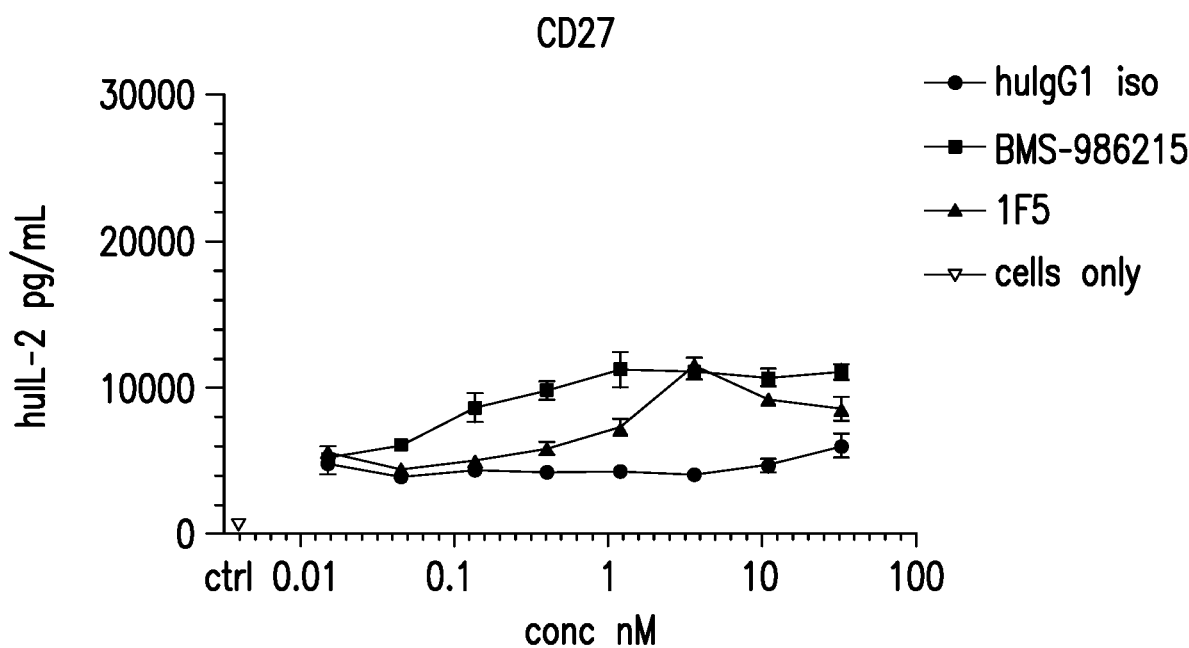
Figure 10E:
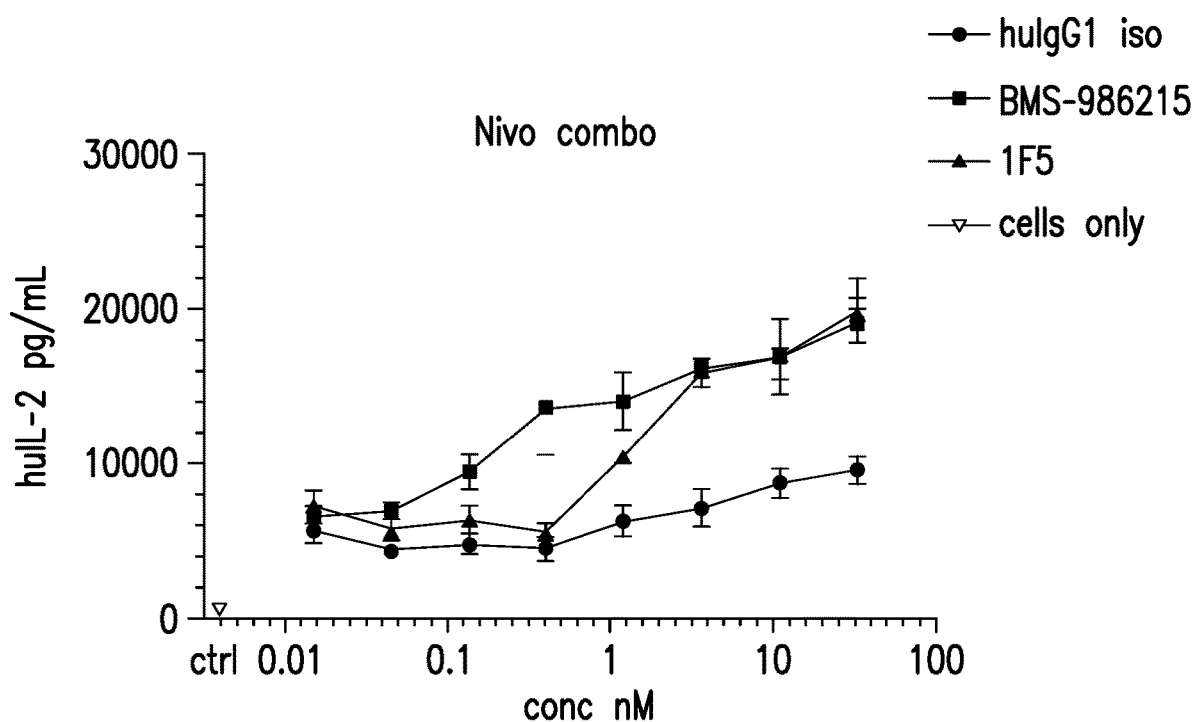
Figure 10F:
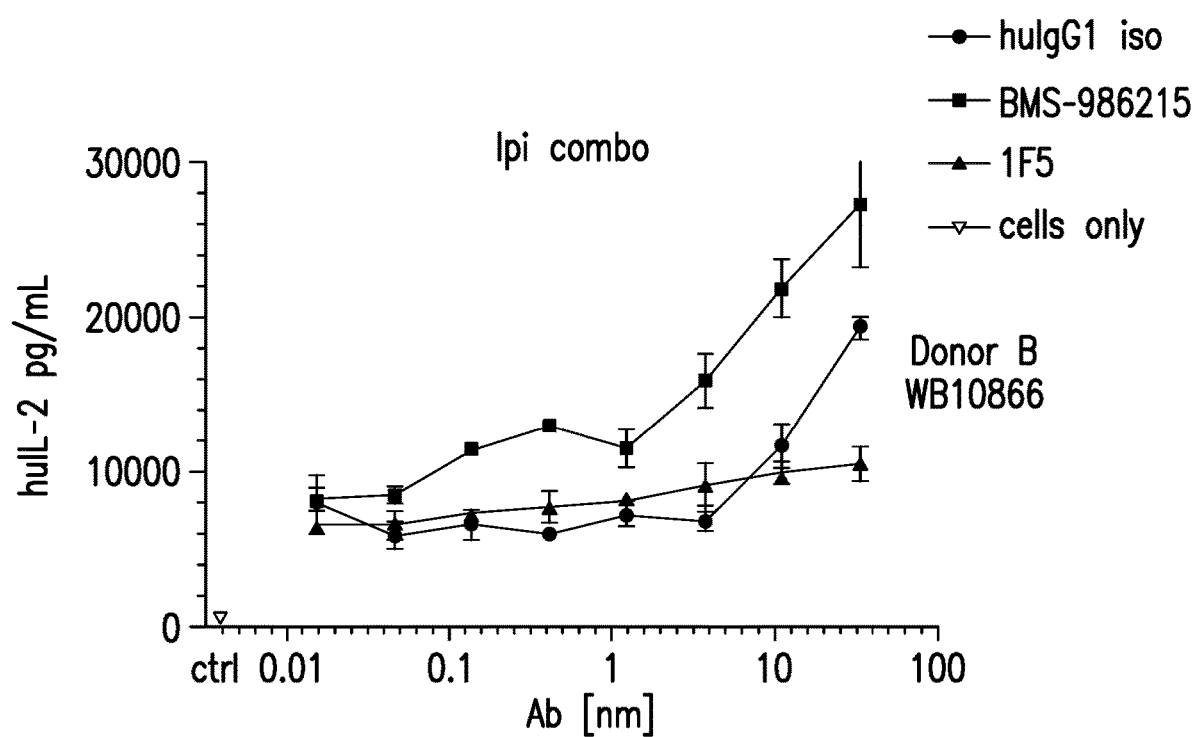

Additional assays were performed in which CD4+CD25− T cells from two donors were separately co-cultured with B cells, stimulated with Staphylococcal enterotoxin B (SEB), and treated with BMS-986215 or an anti-Keyhole limpet hemocyanin Ab, g1F glycoform (KLH-g1f), each Ab used at 10 μg/ml. Results are shown in FIG. 8, with BMS-986215 resulting in an average induction of IFN-γ secretion greater than 2.5-fold using 100 ng/ml of SEB.

BMS-986215 Enhances IL-2 Secretion

T cells stimulated with SEB were assayed for production of interleukin-2 (IL-2) in the presence of soluble BMS-986215, with or without a cross-linker. Briefly, fresh PBMCs isolated from buffy coats of 3 donors (Donors A-C) were seeded at 100,000 cells per well of a tissue culture plate. SEB was added at 80 ng/mL. Cells were treated with soluble anti-human IgG1 (hIgG1), anti-human OX40 (OX40.21), a reference anti-hCD27 (1F5-IgG1), or BMS-986215 Abs. The Abs were titrated 3-fold in the presence or absence of 2.5 μg/mL an anti-human Fcγ Ab (Jackson ImmunoResearch, West Grove, PA) as a cross-linker. PBMCs without SEB or Ab treatments (cells only), and PBMCs treated with SEB but not Abs (SEB only), were used as controls.

Results are shown in FIG. 9. PMBCs from Donors A and B were treated without (FIGS. 9(A) and (C)) or with (FIGS. 9(B) and (D)) cross-linking of soluble Abs. PMBCs from Donor C (FIG. 9(E)) were treated only with cross-linking of soluble Abs. The results show that IL-2 secretion increased from SEB-stimulated human PBMCs in the presence of soluble crosslinked BMS-986215 by greater than about 50% as compared to hIgG1.

A further assay was conducted to determine the effect of BMS-986215 on IL-2 production when combined with PD-1 blockade. Briefly, fresh PBMCs isolated from buffy coats of 2 donors (Donors A and B) were seeded at 100,000 cells per well of a tissue culture plate. SEB was added at 80 ng/mL. Cells were treated with 5 μg/ml of soluble anti-human IgG1 (hIgG1), 1F5, or BMS-986215 Abs alone or titrated in tandem with 0.1 μg/ml of nivolumab for PD-1 blockade or ipilimumab for CTLA-4 blockade. PBMCs without SEB or Ab treatments (cells only) were used as controls.

Results are shown in FIG. 10. IL-2 release was amplified 2-fold by BMS-986215 when combined with PD-1 blockade versus without PD-1 blockade.

BMS-986215 Reduces Suppression of Responder T Cells by Regulatory T Cells

Forkhead box P3 (Foxp3)+CD4+ T cells, known as regulatory T cells or Tregs, suppress immune responses, which can allow tumors to escape from immune surveillance. In general, Tregs express either CD45RA or CD45RO. Tregs can suppress responder T cells (Tresps).

The effect of BMS-986215 on Treg-mediated suppression was investigated.

Figure 11A:
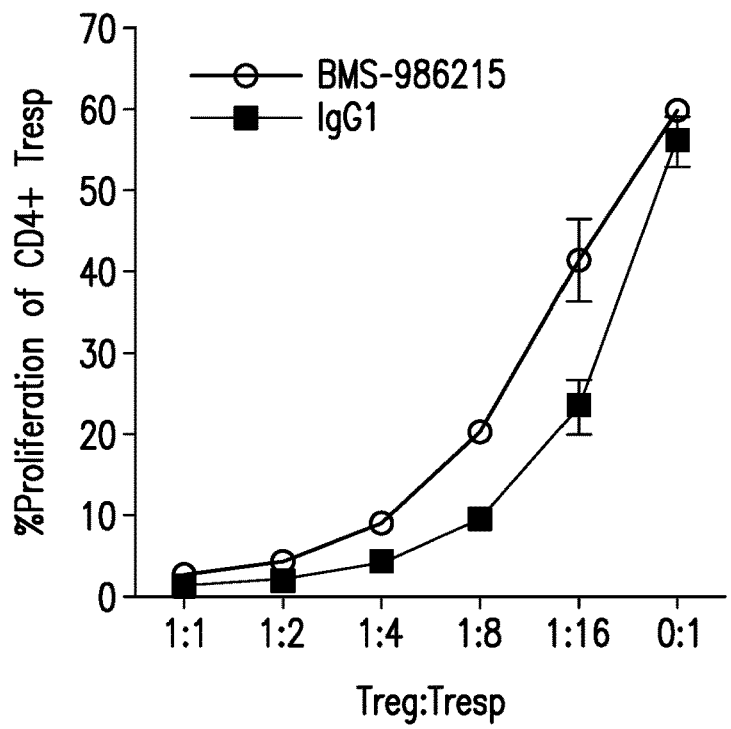
FIGS. 11(A)-(C) show that BMS-986215 reverses regulatory T cells (Treg)-mediated suppression and induces expansion of responder T cells (Tresp). (A) shows the effect of BMS-986215 and IgG1 (control) Abs on Treg-mediated suppression of co-cultured CD4$^+$ Tresp in the presence of MDDC and soluble anti-human CD3 mAb, OKT3. Ratios of Treg:Tresp are shown on the x-axis and the percentage proliferation of CD4$^+$ Tresp is shown on the y-axis. BMS-986215 reversed suppression by greater than 70%. (B) and (C) show numbers of Tresp cells (Foxp3$^-$ events in (B)) and number of Foxp3$^+$ Treg cells (Foxp3$^+$ events in (C)) after Tresp cells were cultured for 7 days in wells coated with OKT3 and either BMS-986215 (0.8), 1F5, or anti-KLH (KLH) Abs in the presence of soluble anti-CD28. (C) shows cell numbers for CD45RA$^+$ and CD45RO$^+$ Treg populations.

In a first assay, CD45RA+ Tregs were seeded at 50,000 cells/well of a tissue culture plate and diluted 1:2 by addition of 50,000 labeled Tresps per well. Next, 5,000 monocyte derived dendritic cells (MDDCs) were added per well with 0.3 μg/mL soluble muromonab-CD3 (OKT3), an anti-human CD3 mAb. Soluble BMS-986215 or control IgG1 Ab was then added at 10 μg/mL. Cells were incubated for 96 h at 37° C. and the ratio of Treg:Tresp and percentage proliferation of CD4+ Tresp were determined by fluorescence-activated cell sorting (FACS). Results are shown in FIG. 11(A). Treg-mediated suppression of co-cultured CD4+ Tresps in the presence of MDDC and soluble OKT3 was reversed with BMS-986215 by greater than 70% in 2 experiments as compared to control IgG1 Ab.

Figure 11B:
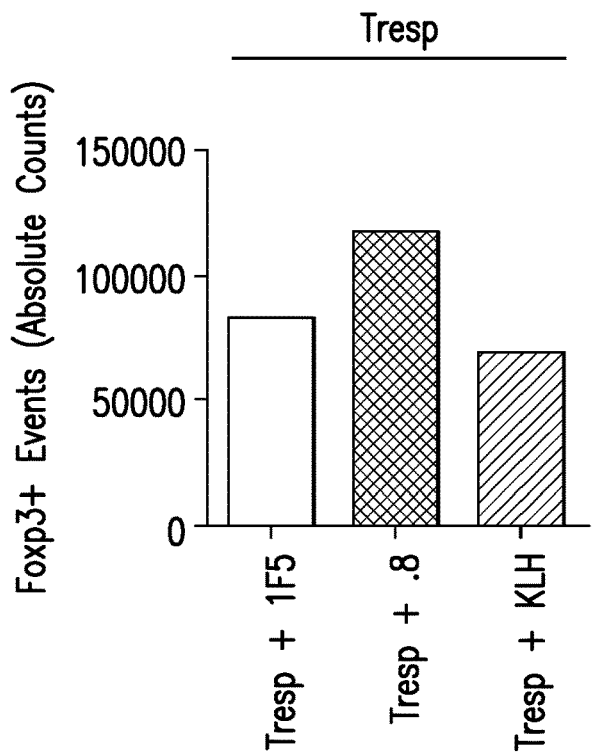
Figure 11C:
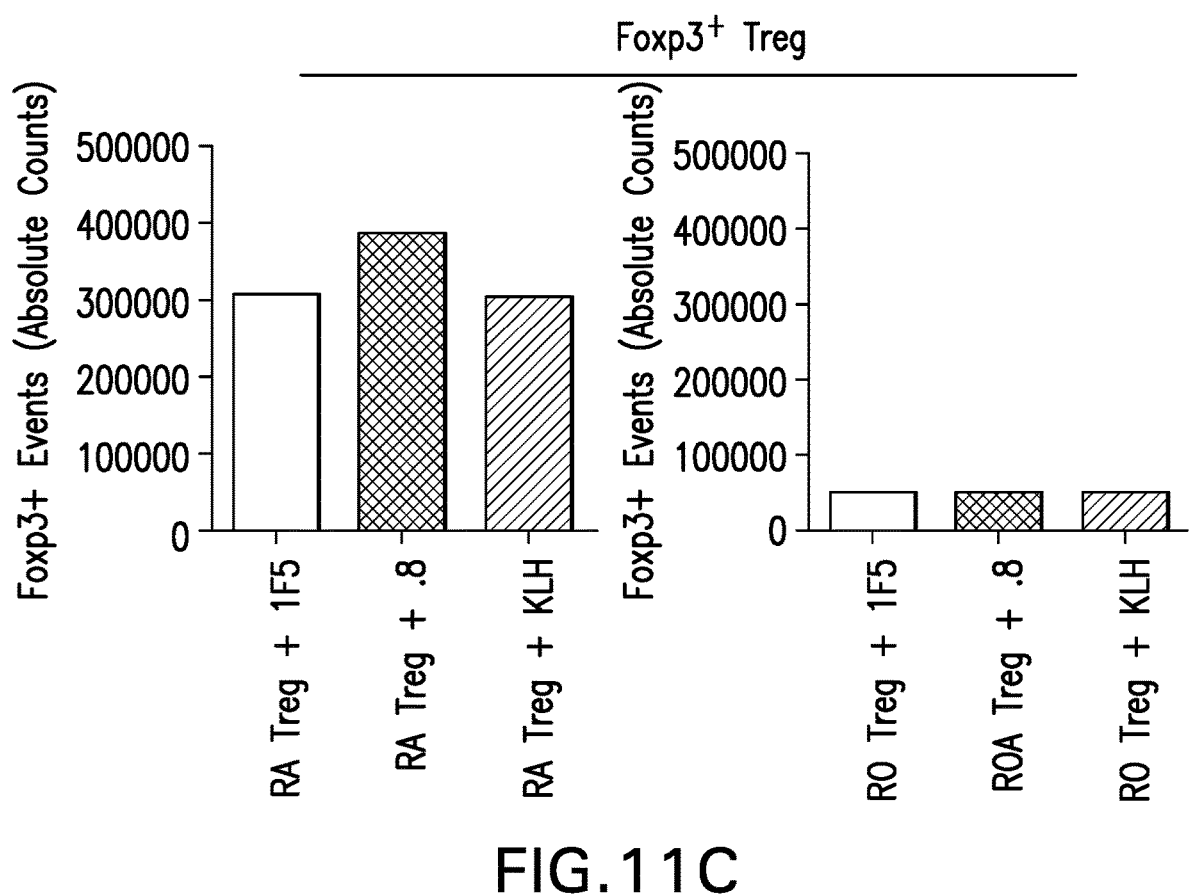

In a second assay, 96-well U-bottom plates were coated with 3 μg/mL OKT3 and 10 μg/mL of BMS-986215, 1F5, or anti-KLH Ab. Next, 20,000 Tresps were added per well. Additional IL-2 was not added. Then, 1 μg/mL of soluble anti-CD28 Ab was added. Cells were cultured for 7 days and the number of Tresp and Foxp3+ Treg cells were determined. Results are shown in FIGS. 11(B) and (C). BMS-986215 induced more expansion of Tresps than Foxp3+ Tregs.

Figure 12A:
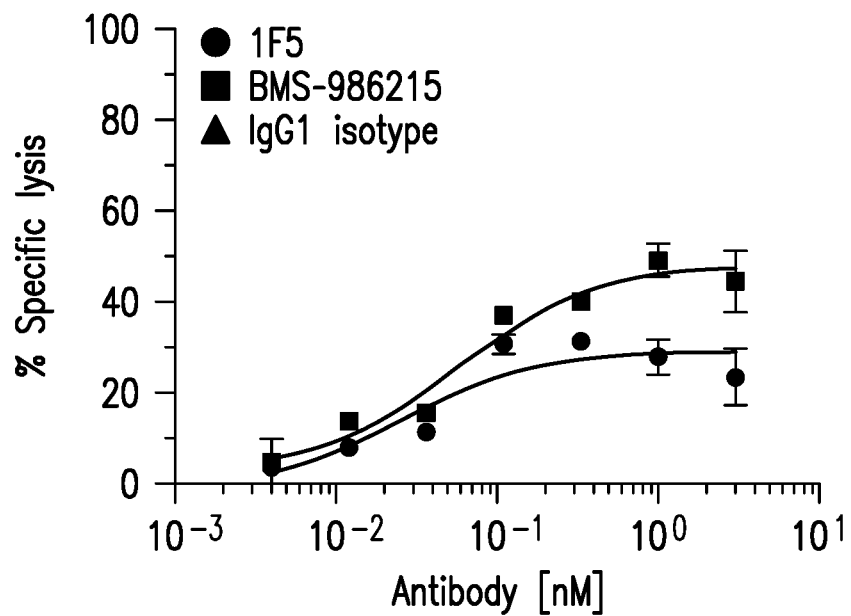
FIG. 12 shows modest induction of ADCC activity by BMS-986215. (A) and (B) show experiments in which BMS-986215, 1F5, or IgG1 isotype (control) Abs were added to co-cultures of primary natural killer (NK) cells as effector cells and activated T cells as target cells at a 10:1 ratio of effector to target (n=8).
Figure 12B:
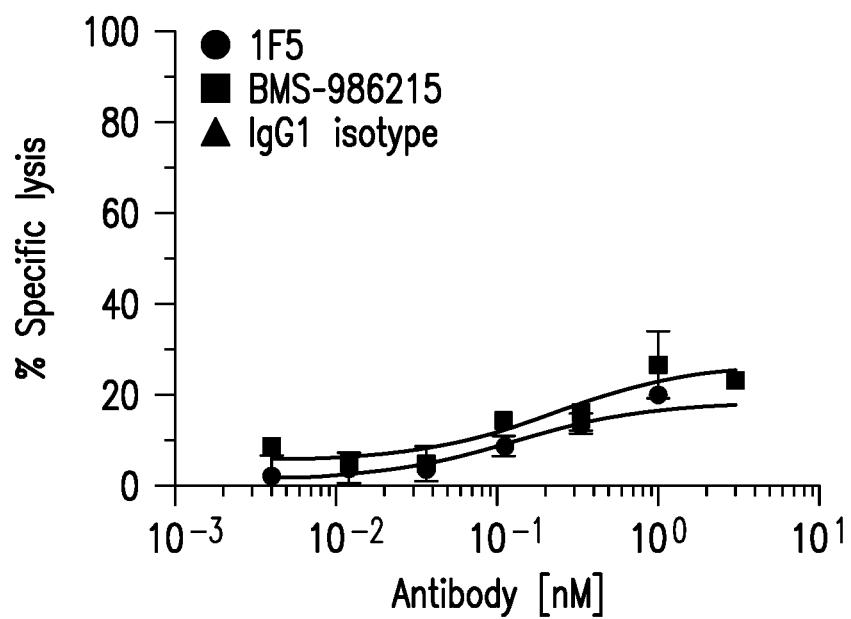

BMS-986215 Induces Modest ADCC Activity with Low Levels of Fc Effector Functions BMS-986215, 1F5, or IgG1 (control) Abs were added to a co-culture of primary natural killer (NK) cells as effector cells and activated T cells or Ramos cells as target cells at a 10:1 ratio of effector to target (n=8). Results are shown in FIG. 12 for T cells. BMS-986215 induced 20-44% lysis of T cells or Ramos cells, indicating modest induction of ADCC activity.

Fc effector function analyses demonstrated low levels of ADCP, CDC, and C1q binding activities (data not shown).

BMS-986215 with or without an anti-PD-1 mAb did not mediate spontaneous cytokine secretion in fresh whole blood samples from 8 normal human donors (data not shown).

Agonistic Activity of BMS-986215 on Human T Cells is Potentiated by CD70

Figure 13A:
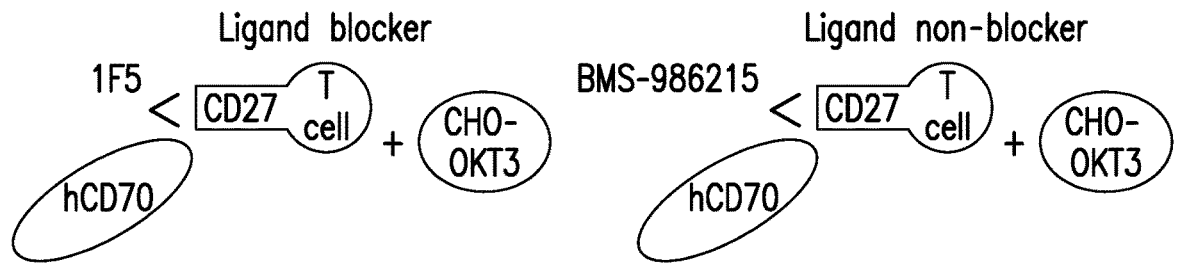
FIGS. 13(A)-(D) show agonist activity by BMS-986215 in activation of T cells in the absence of FcγR, and potentiation by soluble human CD70 (shCD70). (A) shows illustrations of the effects of a ligand blocking anti-CD27 Ab (1F5) and a non-ligand blocking Ab (BMS-986215) in an assay in which human CD4$^+$ T cells were co-cultured with CHO-OKT3 cells (CHO cells that express a single-chain anti-CD3 scFv Ab derived from the anti-CD3 OKT3 mAb). (B)-(E) show graphs in which the assay of (A) was conducted by treating the co-cultures with BMS-986215, 1F5, or hIgG1 (control) Abs, without addition of shCD70 ((B) and (C)) or with addition of 10 µg/ml shCD70 ((D) and (E)), and analyzed for T cell proliferation ((B) and (D)) or IFN-γ secretion ((C) and (E)).
Figure 13B:
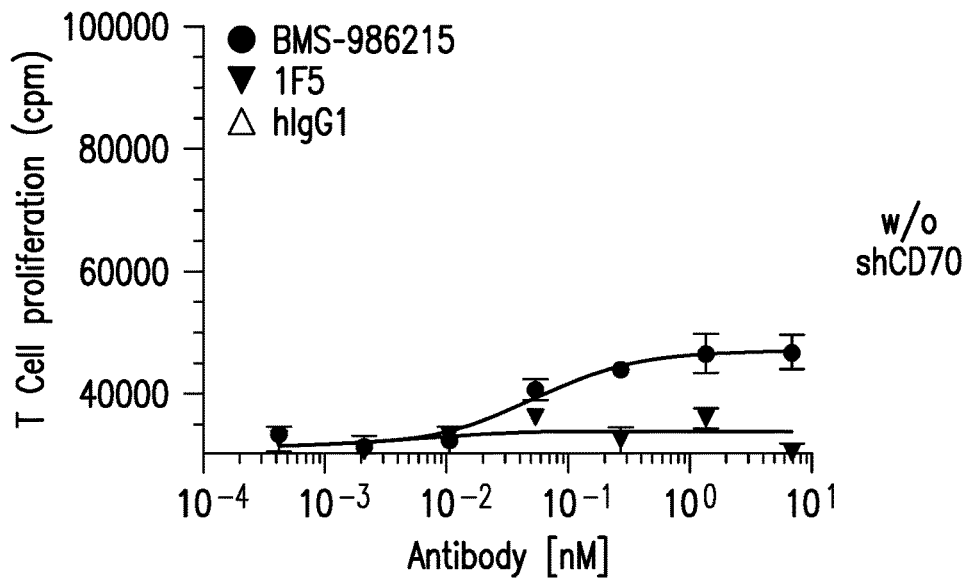
Figure 13C:
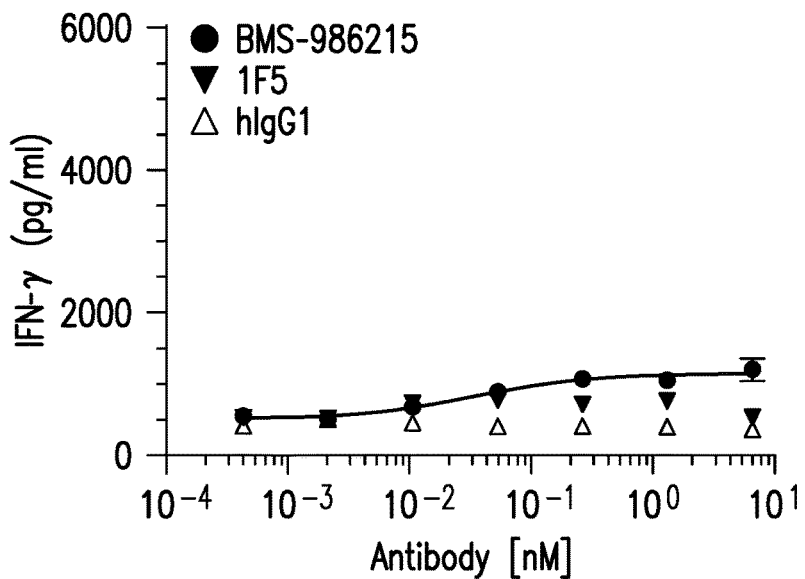
Figure 13D:
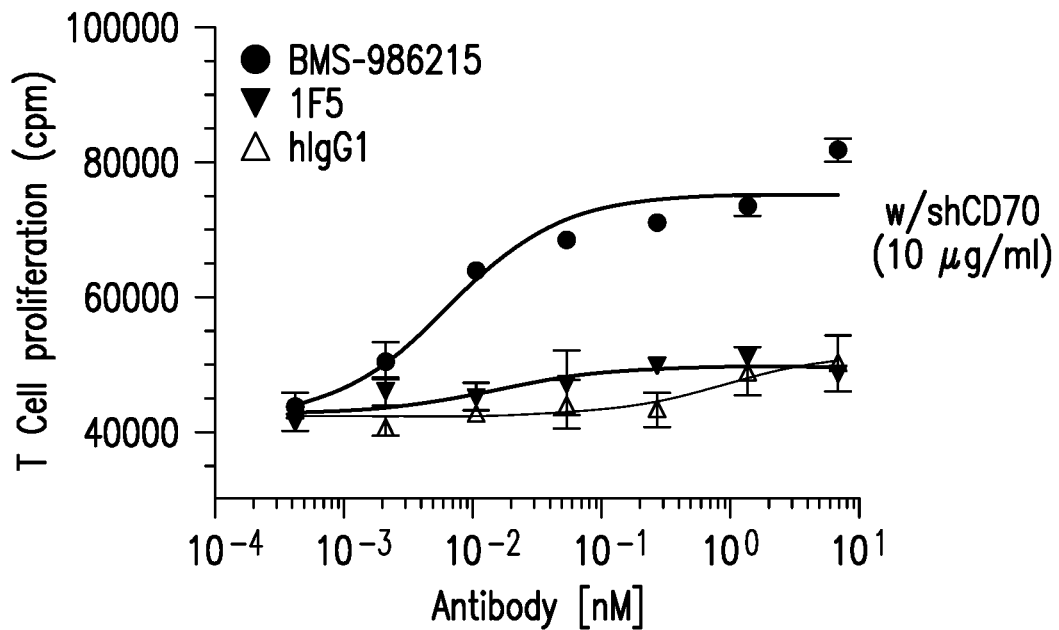
Figure 13E:
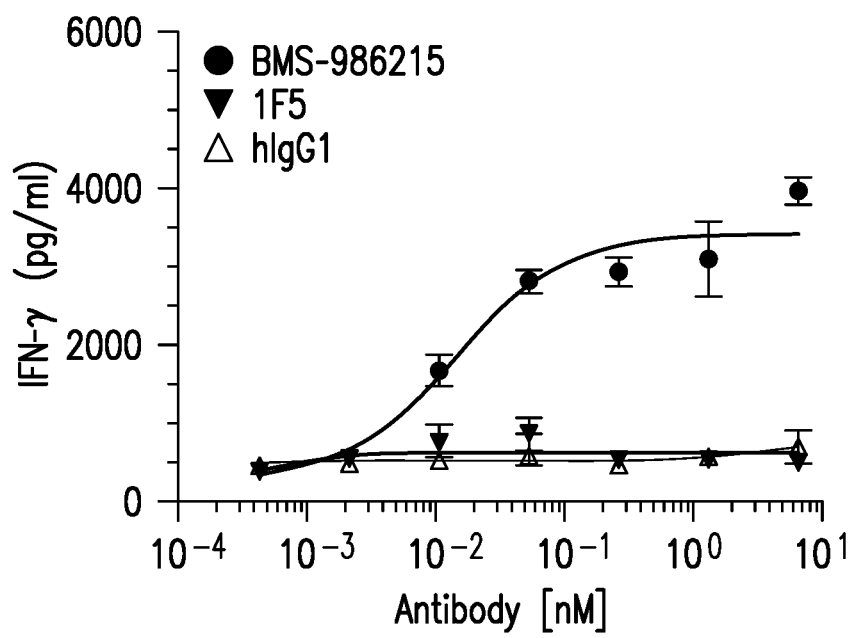

Co-cultures of $CD4^+$ T cells and CHO-OKT3 cells were used to assay the effect of BMS-986215 on T cell proliferation and IFN-γ secretion in the absence of FcγR. Briefly, human $CD4^+$ T cells were co-cultured with CHO-OKT3 cells (CHO cells that express a single-chain anti-CD3 scFv Ab derived from the anti-CD3 OKT3 mAb). The co-cultures were treated with BMS-986215, 1F5, or hIgG1 (control) Abs, with or without 10 µg/ml soluble human CD70 (shCD70), and analyzed for T cell proliferation and IFN-γ secretion. A schematic of the assay is shown in FIG. 13(A).

Results are depicted in FIG. 13, which shows that BMS-986215, but not 1F5, demonstrated weak agonist activity by enhancing T cell proliferation (B) and IFN-γ secretion (C) in the absence of FcγR and without shCD70. BMS-986215, but not 1F5, potentiated activation of human T cells as measured by induction of T cell proliferation (D) and IFN-γ secretion (E) by soluble CD70 protein.

Example 6

Preclinical Pharmacokinetics, Receptor Occupancy Prediction, and Toxicology

Pharmacokinetics and Toxicology of BMS-986215 in Cynomolgus Monkeys

Table 6 summarizes the pharmacokinetic (PK) parameters of BMS-986215 following single intravenous doses of 0.2 and 4 mg/kg to cynomolgus monkeys. $C_{max}$ was reached after approximately 6 h for the 0.2 mg/kg dose and after approximately 24 h for the 4 mg/kg dose. With a 20-fold increase in the doses studied, the total body clearance (CLT) decreased from 2.2 to 0.39 mL/h/kg. As a result, the half-life ($t_{1/2}$) increased from 2.2 to 14 days. In addition, anti-drug Abs (ADAs) were detected in serum samples at 0.2 mg/kg. This suggests target-mediated drug disposition (TMDD) and possibly ADAs could contribute to the nonlinear PK observed with BMS-986215 in monkeys. The $EC_{50}$ for BMS-986215 for binding to cynomolgus T cells is approximately 5 ng/mL.

At each dose level, BMS 986215 was administered intravenously at 1.6 mL/kg to three monkeys; for pharmacodynamic comparisons, two monkeys were administered vehicle. Criteria for evaluation included clinical observations, hematology, PK, CD27 receptor occupancy (RO), circulating sCD27 levels, lymphocyte subset analysis, cytokine levels, and ADA determination. Blood samples were obtained prior to dosing and at various intervals up to 42 days post-dose. Overall, there were no adverse findings, including no adverse clinical observations and no changes in hematologic parameters. There were time- and dose-dependent increases in circulating sCD27 levels. BMS-986215 CD27 RO on $CD4^+$ and $CD8^+$ T cells higher than 90% was detected for approximately 7 days at 0.2 mg/kg and for the duration of the study (42 days) at 4 mg/kg. There were no significant changes in circulating lymphocyte subsets including $CD4^+$, Treg ($Foxp3^+/CD4^+$), $CD8^+$ T, $CD20^+$ B, and NK cells, or circulating cytokine levels.

TABLE 6

Pharmacokinetic Parameters of BMS-986215 after Intravenous Administration in Cynomolgus Monkeys

| Dose (mg/kg) | AUC(INF) (µg/mL × day) | $T_{1/2}$ (day) | CLT (mL/h/kg) | Vss (mL/kg) |
|---|---|---|---|---|
| 0.2 | 3.9 ± 0.8 | 2.2 ± 1.9 | 2.2 ± 0.5 | 127 ± 14 |
| 4 | 441 ± 101 | 14 ± 4 | 0.39 ± 0.08 | 183 ± 19 |

PK parameters were calculated by a non-compartmental method. Values are mean ± SD. (N = 3)

Pharmacokinetic/Pharmacodynamic Modeling of Whole Blood CD27 Receptor Occupancy of BMS-986215 in Monkeys The CD27 RO was determined in whole blood from a monkey PK/RO study and linked with the serum BMS-986215 concentration using an $E_{max}$ model as shown below:

$$RO = \frac{E_{max} \times C_p}{EC_{50} + C_p}$$

where the $E_{max}$ is the maximum RO (fixed at 100% for BMS-986215); the $EC_{50}$ is the serum concentration corresponding to 50% of the $E_{max}$. The estimated in vivo serum $EC_{50}$ corresponding to 50% of the CD27 RO in monkey whole blood was 0.08±0.03 nM, in agreement with the in vitro binding affinity $EC_{50}$ (0.13±0.07 nM, n=3).

Human Pharmacokinetics and Receptor Occupancy Prediction

The human PK parameters of BMS-986215 were projected from monkey data. Because of nonlinear PK, the human clearance is predicted by considering both non-target- and target-mediated elimination processes as shown below:

$$CL_{tot} = CL_{non-target-mediated} + CL_{target-mediated}$$

Target-mediated clearance can be described using the following equation:

$$CL_{target-mediated} = \frac{V_{max}}{K_m + C_p}$$

where $V_{max}$ is the maximum target-mediated elimination rate, $K_m$ is the serum drug concentration corresponding to 50% of the $V_{max}$, and $C_p$ is the plasma drug concentration. For the non-target-mediated clearance, allometry was employed to scale from monkeys to humans using the power exponent of 0.85. For the target-mediated clearance, both $V_{max}$ and $K_m$ were assumed to be the same between monkey and human. The human steady-state volume of distribution was also predicted using allometry, with the power exponent of 1. As a result, the human $t_{1/2}$ at a dose of 0.1 and 1 mg/kg for a Q3W regimen was predicted to be 2 and 11 days, respectively. The predicted $t_{1/2}$ may be longer if ADAs play a minimal role in humans.

In summary, BMS-986215 exhibited nonlinear PK in cynomolgus monkeys, with the terminal $t_{1/2}$ ranging from 2.2 to 14 days. The nonlinear PK may be attributed to target-mediated drug disposition (TMDD) and possibly the formation of ADAs.

Currently, the peripheral blood receptor occupancy (RO) can be readily predicted in humans using plasma concentrations. Based on a good in vitro-in vivo correlation for CD27 RO observed with BMS-986215 in monkeys, a human dose of 0.7 mg/kg for BMS-986215 given every 3 weeks is predicted to achieve greater than 90% RO at trough.

Example 7

Expression of CD27 and CD70 in Human Cancers

Immunohistochemical Analysis of CD27 Expression in Multiple Human Cancers

To identify potential disease indications, the expression profile and distribution of CD27 in multiple cancer types was studied by immunohistochemistry (IHC) using a commercially available anti-CD27 mAb, Clone 137B4, in regular full-size formalin-fixed paraffin-embedded (FFPE) sections. Six tumor types and 22-55 samples for each tumor type, namely breast adenocarcinoma (BrC, n=35), cervical carcinoma (CC, n=23), colorectal adenocarcinoma (CRC, n=22), head and neck squamous cell carcinoma (HNSCC, n=46), hepatocellular carcinoma (HCC, n=55), and ovarian adenocarcinoma (OvC, n=27), were subjected to IHC staining. In addition, CD70 expression was evaluated using a commercial anti-CD70 mAb in adjacent sections in most cases (n=13-37 samples).

$CD27^+$ staining was observed in a subset of tumor-infiltrating lymphocytes (TILs) in all tumor types examined. In general, $CD27^+$ TILs exhibited a pattern very similar to $CD3^+$ TILs. In rare cases, $CD27^+$ TILs were notably more abundant than $CD3^+$ TILs, suggesting expression of CD27 in B cells in addition to T cells. Among the 6 tumor types, HNSCC and CC showed the highest levels of $CD27^+$ TILs, followed by CRC, BrC, and HCC, whereas OvC showed the lowest level.

$CD70^+$ staining was observed in a small fraction of TILs and at a markedly lower frequency than $CD27^+$ staining. Among the 6 tumor types, CC, HCC, and CRC showed higher levels of $CD70^+$ TILs than HNSCC, BrC, and OvC. In addition to detecting CD70 expression on TILs, $CD70^+$ labeling was revealed in tumor cells in about 30% of CC and 15% of OvC cases. However, among those $CD70^+$ tumor cell cases, most were very low expressers. Using 10% tumor $cell^+$ as a cut-off, about 15% of CC cases were considered positive.

TCGA Analysis of CD27 and CD70 Expression

As observed with other costimulatory and checkpoint receptors, analysis of The Cancer Genome Atlas (TCGA) database shows that CD27 is expressed at the RNA level in most tumors in a manner correlating with other T cell signatures. The exception is lymphoma in which CD27 is expressed by the malignant B cell. CD27 expression by itself was not significantly associated with survival, with the exception of cervical cancer and head and neck cancer, in which high expression was associated with improved survival (p=0.00001 and 0.01, respectively). After B lymphoma, the tumors with the highest CD27 expression were thyroid, renal cell, lung, and head and neck.

In the cervical cancer TCGA data set, amongst the high CD27 expression population, high CD70 expressors have better survival than lower CD70 expressers, suggesting that increased CD27 agonism with BMS-986215 would provide benefit.

Soluble CD27

It has been suggested that soluble CD27 (sCD27) may be a marker of immune cell activation that can be followed as a pharmacodynamic (PD) marker in clinical trials (Huang et al., 2013). As such, serum from patients with stage I-IV melanoma, CRC, RCC, and lung cancer were tested for sCD27 levels and compared to non-cancer control from normal healthy volunteer (NHV) serum samples. Some individuals among the cancer patients had a 2- to 3-fold higher level of sCD27 in their serum (2000-15,000 μg/mL) compared to NHV (2000-7000 μg/mL). This is different and higher than reported in the literature where sCD70 was reported as being lower in cancer patients (150 μg/mL) vs NHV (500 μg/mL).

In cynomolgus monkeys treated with anti-CD27 mAbs, it was found that sCD27 levels increased, even though assays to detect peripheral T cell activation did not show increases in activation or proliferation. Thus, it is likely that the elevated sCD27 seen after anti-CD27 treatment is the result of prolonged FcRn-mediated circulating $t_{1/2}$.

Example 8

Mouse Tumor Studies

To demonstrate that a non-ligand blocking CD27 mAb has anti-tumor activity in mouse tumor models, rat anti-mouse CD27 mAbs were generated as described in Example 1, and Clone 8H5 was selected as a ligand non-blocking agonist Ab that could serve as a surrogate for BMS-986215. This surrogate anti-CD27 Ab binds to mCD27 with 0.25 nM affinity, does not block mouse CD70 binding, displays agonistic activity on mouse splenic T cells, and was engineered with mIgG1 and mIgG2a Fc variants. As such, 8H5 is a suitable surrogate for BMS-986215.

Figure 14A:
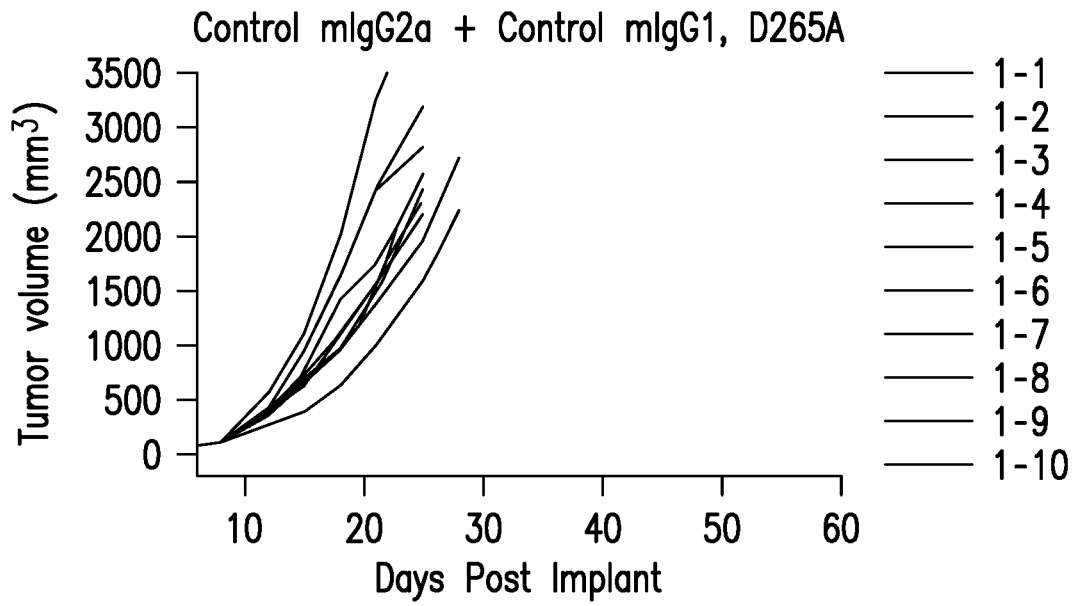
FIGS. 14(A)-(F) shows that an anti-mouse CD27 mAb, Clone 8H5, that is a surrogate of BMS-986215, potentiates anti-PD-1 mAb activity in murine tumor models. BALB/c mice with a subcutaneous implant of 1×10$^6$ CT26 cells as a murine colon carcinoma model were treated with intraperitoneal injections at days 6, 9, and 13 after implant with 10 mg/kg of a combination of control mouse IgG2a and control mouse IgG1-D265A isotype mAbs (A: Control mIgG2a$^+$ Control mIgG1, D265A); an anti-mouse CD27 (anti-mCD27) surrogate of BMS-986215, designated mAb 8H5, which was formatted as a mouse IgG1 isotype (B: anti-mCD27, 8H5, mIgG1); 8H5 formatted as a mouse IgG2a isotype (C: anti-mCD27, 8H5, mIgG2a); an anti-mouse PD-1 mAb formatted as a Fc-inert mouse IgG1-D265A isotype (D: anti-mPD-1, mIgG1, D265A); a combination of anti-mPD-1, mIgG1, D265A and anti-mCD27, 8H5, mIgG1 (E); and a combination of anti-mPD-1, mIgG1, D265A and anti-mCD27, 8H5, mIgG2a (F). Combined CD27 agonism by anti-mCD27 mAb with PD-1 blockade resulted in improved tumor growth inhibition (TGI) and more tumor-free (TF) mice (FIG. 14(E): 70% TGI, 3/10 TF, respectively) than single agent therapies (FIG. 14(B), anti-mCD27: 22% TGI, 0/10 TF.
Figure 14B:
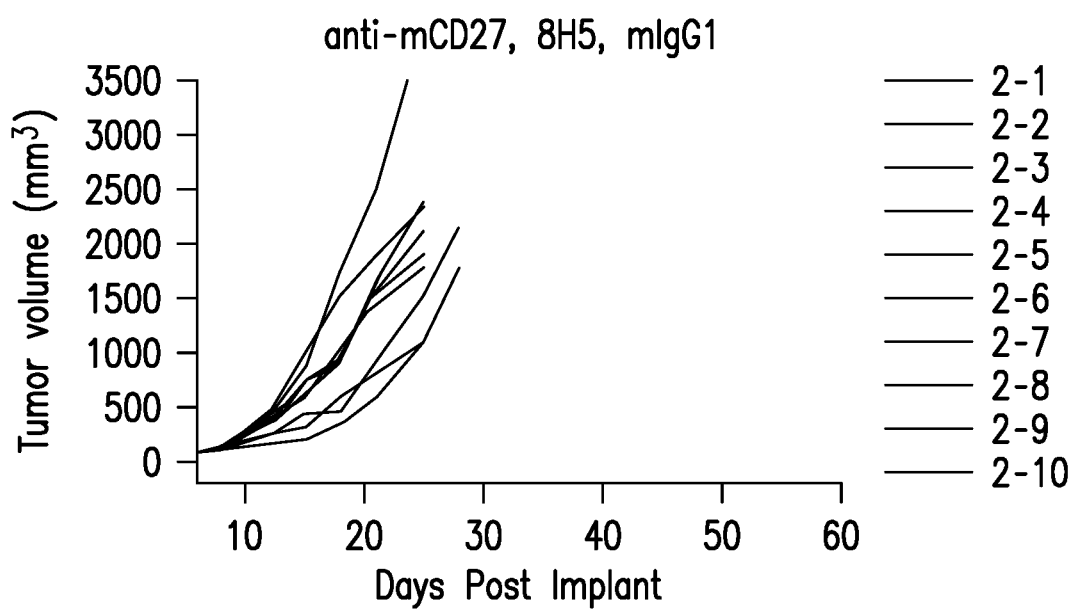
Figure 14C:
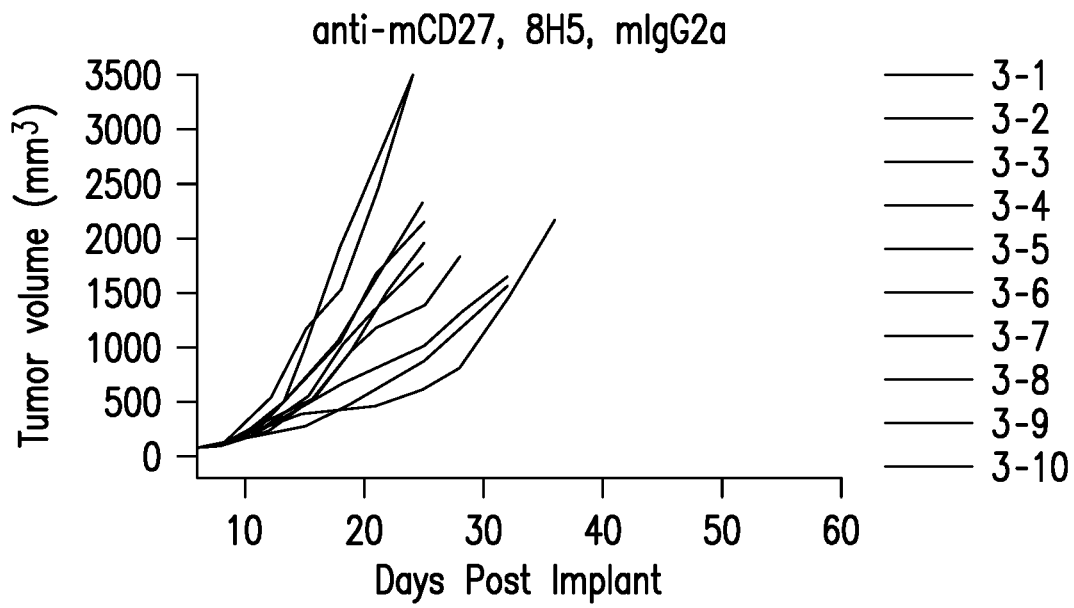
Figure 14D:
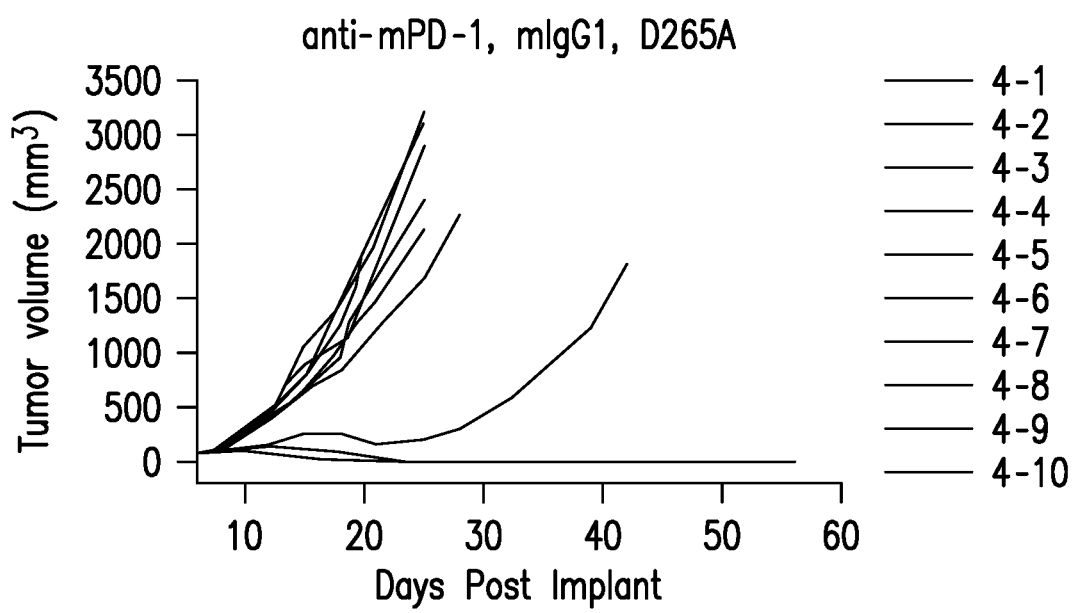
Figure 14E:
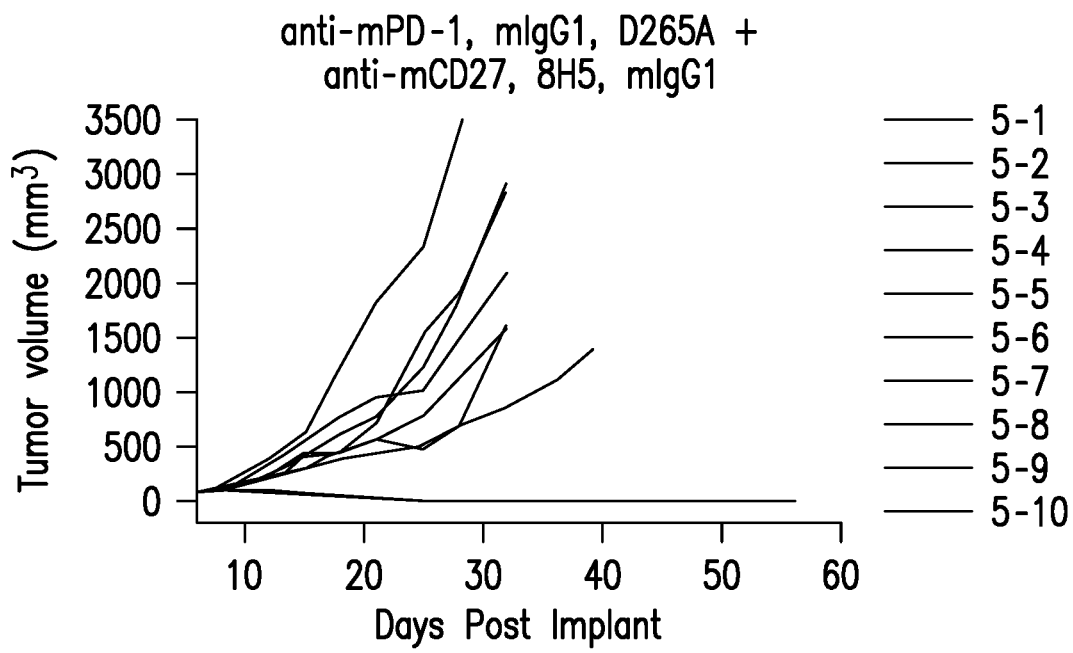
Figure 14F:
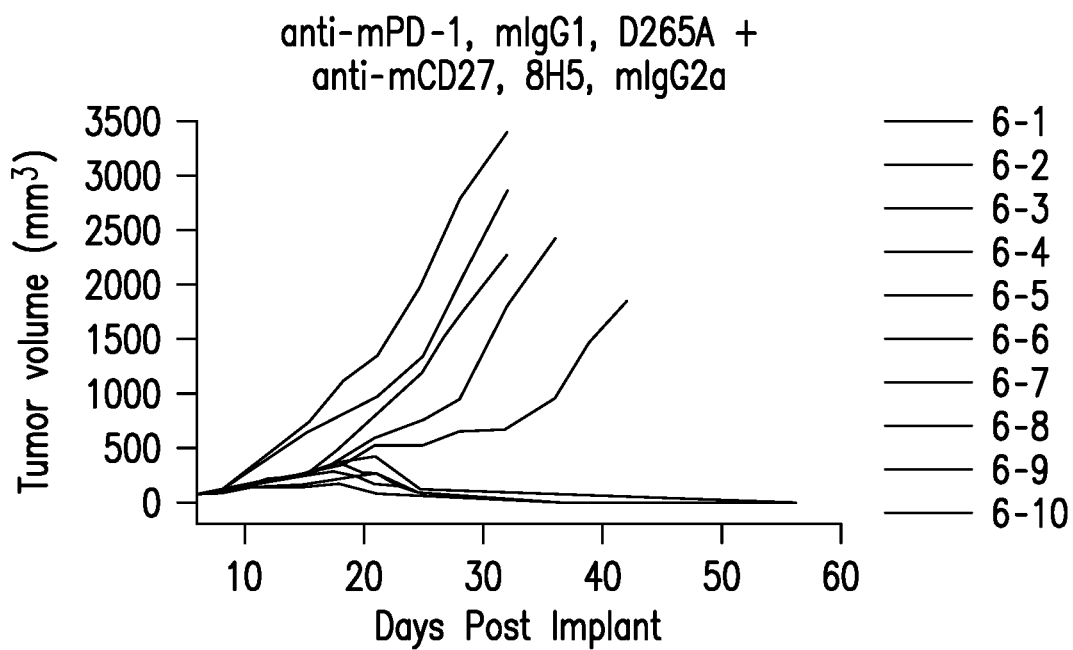

Clone 8H5 demonstrated antitumor activity in both solid and hematological murine tumor models, particularly in combination with PD-1 checkpoint blockade. See, e.g., FIG. 14 showing results in the CT26 murine colon carcinoma model, and Table 7 summarizing the results obtained in the SA1N fibrosarcoma, CT26 and EGT T cell lymphoma mouse models. The mIgG1 isotype of 8H5 showed only modest anti-tumor activity in the CT26 model with 21% tumor growth inhibition (TGI; FIG. 14(B))) compared to mIgG2a and mIgG1, D265A controls (FIG. 14(A)). The mIgG2a isotype of 8H5 showed slightly higher, but still modest, anti-tumor activity (FIG. 14(C)), with neither the mIgG1 nor the IgG2a isotypes producing any tumor-free (TF) mice out of 10 mice treated.

The anti-tumor activity of the anti-mPD-1 Ab, 4H2, with a mIgG1-D265A isotype, was also tested. 4H2 is a chimeric rat-mouse anti-mPD-1 Ab constructed from a rat IgG2a anti-mouse PD-1 Ab in which the Fc-portion was replaced with the Fc-portion from different mouse IgG isotypes (WO 2006/121168). In the CT26 tumor model, 4H2 showed moderate anti-tumor activity, producing 27% TGI and two TF mice out of 10 treated (FIG. 14(D)). This anti-PD-1 activity was potentiated by 8H5, evidenced by the combination with 8H5, mIgG1, producing 70% TGI and 3/10 TF mice (FIG. 14(E); Table 7), and the combination with 8H5, mIgG2a producing 76% TGI and 4/10 TF mice (FIG. 14(F); Table 7). This demonstrates that anti-CD27 interacts synergistically with a checkpoint inhibitor, such as anti-PD-1, in reducing the growth of cancer cells in vivo. A combination of Abs is considered synergistic if the antitumor effect of the combination is greater than the sum of the level of inhibition exhibited by each Ab individually.

Varying the isotype of Abs specific for T cell surface receptors (both costimulatory and coinhibitory) can potentially alter the antitumor activity of these Abs. When tumor-bearing mice were treated with single-agent 8H5 expressed as mIgG1 and mIgG2a (activating FcγR binder) mAbs, potent antitumor activity was observed in the SA1N fibrosarcoma model. The mIgG1 isotype of 8H5 showed potent anti-tumor activity, producing 52% TGI and eight TF mice out of 12 treated (Table 7). The mIgG2a isotype of 8H5 was even more potent, producing 98% TGI and 11 TF mice out of 12 treated (Table 7). The monotherapy activity was associated with expansion of CD8+ T cells and depletion of Tregs at the tumor site. Recent preclinical studies indicate that an agonistic CD27 Ab increases the activity of antigen-specific CD8+ T cells when combined with PD-1 blockade, which is effective in eradicating tumors (Ahrends et al., 2016). Anti-mouse CD27 isotypes, combined with anti-mouse PD-1, showed comparable levels of antitumor activity in the CT26 model as measured by TGI at Day 25 (70% and 76% TGI, respectively) and the total number of tumor-free (TF) mice (3/10 and 4/10 TF, respectively). See Table 7.

In addition to partial Treg depletion, mice treated with either 8H5 mIgG1 or 8H5 mIgG2a had reduced numbers of CD4+ and CD8+ T cells in the periphery (e.g., blood and spleen) as compared to tumor sites. More expansion of CD8+ T cells was observed with the mIgG1 than the mIgG2a isotype within tumors, while the mIgG2a appeared to be more potent in depleting Tregs. These data suggest that the anti-CD27 isotype variants primarily produce antitumor activity through Treg depletion (mIgG2a) and/or expansion of CD8+ T cells (mIgG1). These studies have demonstrated that CD27 agonism and PD-1 blockade results in lower tumor burden and increased survival in syngeneic tumor models. See Table 7.

Neither the mIgG1 nor mIgG2a isotypes of the anti-mCD27 mAb, 8H5, showed anti-tumor activity against murine EG7 T cell lymphoma cells, while anti-PD1 mAb 4H2 showed only very modest activity (Table 7). Nevertheless, 8H5 mIgG1 combined synergistically with 4H2 to produce 44% TGI and 1/10 TF mouse in this lymphoma model (Table 7).

TABLE 7

Summary of Preclinical Efficacy Studies Using Anti-Mouse CD27 as Monotherapy or Combined with Other Agents in a Variety of Mouse Tumor Models

| Tumor | mAbs | Outcome |
|---|---|---|
| Fibrosarcoma SA1N[a] | Anti-mCD27 8H5 mIgG1 | Monotherapy 52% TGI, 8/12 TF |
| | Anti-mCD27 8H5 mIgG2a | 98% TGI, 11/12 TF MOA: Treg depletion with mIgG2a and CD8+ T cells expansion with mIgG1 at tumor sites |
| Colon CT26[b] | | Monotherapy |
| | Anti-mCD27 8H5 mIgG1 | 21% TGI, 0/10 TF |
| | Anti-mCD27 8H5 mIgG2a | 24% TGI, 0/10 TF |
| | Anti-mPD-1 4H2 mIgG1-D265A | 27% TGI, 2/10 TF Combined Therapy |
| | 4H2 mIgG1-D265A + 8H5 mIgG1 | 70% TGI, 3/10 TF |
| | 4H2 mIgG1-D265A + 8H5 mIgG2a | 76% TGI, 4/10 TF |

TABLE 7-continued

Summary of Preclinical Efficacy Studies Using Anti-Mouse CD27 as Monotherapy or Combined with Other Agents in a Variety of Mouse Tumor Models

| Tumor | mAbs | Outcome |
|---|---|---|
| | | MOA: CD8 T cells expanded with mIgG1 and Treg depleted at tumor sites with mIgG2a intumor sites |
| Lymphoma EG7[c] | | Monotherapy |
| | Anti-mCD27 8H5 mIgG1 | 0% TGI, 0/10 TF |
| | Anti-mCD27 8H5 mIgG2a | 0% TGI, 0/10 TF |
| | Anti-mPD-1 4H2 mIgG1-D265A | 8% TGI, 1/10 TF Combined Therapy |
| | 4H2 mIgG1-D265A + 8H5 mIgG1 | 44%, TGI, 1/10 TF |
| | 4H2 mIgG1-D265A + 8H5 mIgG2a | 0% TGI, 0/10 |

[a]Data in AJ mice
[b]Data in BALB/c mice
[c]Data in C57BL/6 mice
Abbreviations: TGI = tumor growth inhibition at Day 21-28 post inoculation; TF = tumor-free at end of study

REFERENCES

Abhinandan K R, Martin A C (2008) Analysis and improvements to Kabat and structurally correct numbering of antibody variable domains. Mol Immunol 45:3832-9.

Ahrends T, Bąbała N, Xiao Y et al. (2016) CD27 agonism plus PD-1 blockade recapitulates CD4+ T cell help in therapeutic anti-cancer vaccination. Cancer Res 76(10): 2921-31.

Al-Lazikani, Lesk A M, Chothia C (1997) Standard conformations for the canonical structures of immunoglobulins. J Mol Biol 273(4):927-48.

Baitsch L, Legat A, Barba L, Fuertes Marraco S A, Rivals J P et al. (2012) Extended co-expression of inhibitory receptors by human CD8 T-cells depending on differentiation, antigen-specificity and anatomical localization. PloS One 7(2): e30852.

Brahmer J R, Drake C G, Wollner I, Powderly J D, Picus J et al. (2010) Phase I study of single-agent anti-programmed death-1 (MDX-1106) in refractory solid tumors: safety, clinical activity, pharmacodynamics, and immunologic correlates. J Clin Oncol 28:3167-75.

Brahmer J R, Hammers H, Lipson E J (2015) Nivolumab: targeting PD-1 to bolster antitumor immunity. Future Oncol 11(9):1307-26.

Brahmer J R, Tykodi S S, Chow L Q, Hwu W J, Topalian S L et al. (2012) Safety and activity of anti-PD-L1 antibody in patients with advanced cancer. N Engl J Med 366:2455-65.

Buchan S L, Manzo T, Flutter B et al. (2015) OX40- and CD27-mediated costimulation synergizes with anti-PD-L1 blockade by forcing exhausted CD8+ T cells to exit quiescence. J Immunol 194:125-33.

Buchan S L, Fallatah M, Thirdborough S M, Taraban V Y, Rogel A et al. (2018) PD-1 blockade and CD27 stimulation activate distinct transcriptional programs that synergize for CD8+ T-cell driven anti-tumor immunity. Clin Cancer Res 24(10):2383-94.

Bullock T, McClintic H, Jeong S et al. (2014) Immune correlates of varlilumab (CDX-1127) treated cancer patients are consistent with CD27 costimulatory activity. Society for Immunotherapy of Cancer (SITC) 29th Annual Meeting, Nov. 6-9, 2014, National Habor, M D; Celldex Poster P115.

Callahan M, Postow M A, Wolchok J D (2016) Targeting T cell co-receptors for cancer therapy. *Immunity* 44(5): 1069-78.

Chakravarthi B V S K, Nepal S, Varambally S (2016) Genomic and epigenomic alterations in cancer. *Am J Pathol* 186(7): 1724-35.

Chen D S, Mellman I (2013) Oncology meets immunology: the cancer-immunity cycle. *Immunity* 39(1), 1-10.

Chothia C, Lesk A M (1987) Canonical structures for the hypervariable regions of immunoglobulins. *J Mol Biol* 196:901-17.

Chothia C, Lesk A M, Tramontano A, Levitt M, Smith-Gill J S et al. (1989) Conformations of immunoglobulin hypervariable regions. *Nature* 342:877-83.

De Colvenaer V, Taveirne S, Delforche M et al. (2011) CD27-deficient mice show normal N K-cell differentiation but impaired function upon stimulation. *Immunol Cell Biol* 89:803-11.

Dolfi D V, Boesteanu A C, Petrovas C et al. (2008) Late signals from CD27 prevent Fas-dependent apoptosis of primary $CD8^+$ T cells. *J. Immunol* 180:2912-21.

Drugs.com—Opdivo Approval History: www.drugs.com/history/opdivo.html, last accessed Apr. 1, 2019.

Farkona et al. (2016) Cancer immunotherapy: the beginning of the end of cancer? *BMC Medicine* 14:73.

French R R, Taraban V Y, Crowther G R et al. (2007) Eradication of lymphoma by CD8 T cells following anti-CD40 monoclonal antibody therapy is critically dependent on CD27 costimulation. *Blood* 109:4810-5.

Gorelik L, Avgerinos G, Kunes Y, Marasco W A (2017) Preclinical characterization of a novel fully human IgG1 anti-PD-L1 mAb CK-301. In: Proceedings of the American Association for Cancer Research (AACR) Annual Meeting, Apr. 1-5, 2017, *Cancer Res* 77(13 Suppl): Abstract No. 4606.

Guo L, Zhang H, Chen B (2017) Nivolumab as Programmed Death-1 (PD-1) inhibitor for targeted immunotherapy in tumor. *J Cancer* 8(3):410-6.

He L Z, Prostak N, Thomas L J et al. (2013) Agonist anti-human CD27 monoclonal antibody induces T cell activation and tumor immunity in human CD27-transgenic mice. *J Immunol* 191:4174-83.

Hendriks J, Gravestein L A, Tesselaar K et al. (2000) CD27 is required for generation and long-term maintenance of T cell immunity. *Nat Immunol* 1:433-40.

Herbst R S, Soria J C, Kowanetz M, Fine G D, Hamid 0 et al. (2014) Predictive correlates of response to the anti-PD-L1 antibody MPDL3280A in cancer patients. *Nature* 515: 563-7.

Hollinger P, Hudson P J (2005) Engineered antibody fragments and the rise of single domains. *Nature Biotech* 23 (9): 1126-36.

Huang J, Jochems C, Anderson A M et al. (2013) Soluble CD27-pool in humans may contribute to T cell activation and tumor immunity. *J. Immunol.* 190:6250-8.

Huang R, Chen G (2014) Higher order structure characterization of protein therapeutics by hydrogen/deuterium exchange mass spectrometry. *Analytical and Bioanalytical Chemistry* 406:6541-58.

Iwai Y, Hamanishi J, Chamoto K, Honjo T (2017) Cancer immunotherapies targeting the PD-1 signaling pathway. *J Biomed Sci* 24(1):26.

Jones L M, Sperry J B, Carroll J A, Gross M L (2011) Fast photochemical oxidation of proteins for epitope mapping. *Anal Chem* 83:7657-61.

Kabat E A, Wu T T, Bilofsky H, Reid-Miller M, Perry H (1983) Sequences of Proteins of Immunological Interest. Bethesda: National Institute of Health; 1983. 323

Kabat E A, Wu T T, Perry H, Gottesman K, Foeller C (1991) Sequences of Proteins of Immunological Interest, Fifth Edition, U.S. Department of Health and Human Services, NIH Publication No. 91-3242.

Kabat E A, Wu T T, Reid-Miller M, Perry H, Gottesman K (1987) Sequences of Proteins of Immunological Interest, Fourth Edition, U.S. Government Printing Office, NIH Publication No. 165-492.

Kamta J, Chaar M, Ande A, Altomare D A, Ait-Oudhia S (2017) Advancing cancer therapy with present and emerging immuno-oncology approaches. *Front Oncol* 18(7):64.

Kaufman R J, Sharp P A (1982) Amplification and expression of sequences cotransfected with a modular dihydrofolate reductase complementary DNA gene. *Mot Biol* 159:601-21.

Lefranc M P, Pommie C, Ruiz M, Giudicelli V, Foulquier E et al. (2003) IMGT unique numbering for immunoglobulin and T cell receptor variable domains and Ig superfamily V-like domains. *Dev Comp Immunol* 27:55-77.

Lesokhin A M, Callahan M K, Postow M A, Wolchok J D (2015) On being less tolerant: enhanced cancer immunosurveillance enabled by targeting checkpoints and agonists of T cell activation. *Sci Transl Med* 7(280):280sr1.

Lipson E J, Sharfman W H, Drake C G, Wollner I, Taube J M et al. (2013) Durable cancer regression off-treatment and effective reinduction therapy with an anti-PD-1 antibody. *Clin Cancer Res* 19:462-8.

Liu S Y, Wu Y L (2017) Ongoing clinical trials of PD-1 and PD-L1 inhibitors for lung cancer in China. *J Hematol Oncol* 10(1):136.

Mahoney K M, Rennert P D, Freeman G J (2015) Combination cancer immunotherapy and new immunomodulatory targets. *Nat Rev Drug Discov* 14(8):561-84.

Martin A, Cheetham J C, Rees A R (1989) Modeling antibody hypervariable loops: a combined algorithm. *Proc Natl Acad Sci USA* 86(23):9268-72.

MacCallum R M., Martin A C R, Thornton J T (1996) Antibody-antigen interactions: contact analysis and binding site topography. *J Mol Biol* 262:732-45.

Mellman I, Coukos G, Dranoff (2011) Cancer immunotherapy comes of age. *Nature* 480: 480-9.

Munitic I, Kuka M, Allam A et al. (2013) CD70 deficiency impairs effector CD8 T cell generation and viral clearance but is dispensable for the recall response to lymphocytic choriomeningitis virus. *J Immunol* 190:1169-79.

Olafsen T, Wu A M (2010) Antibody vectors for imaging. *Semin Nucl Med* 40(3):167-81.

Ott P A, Hodi F S, Kaufman H L, Wigginton J M, Wolchok J D (2017) Combination immunotherapy: a road map. *J Immunother Cancer* 5:16.

Pardoll D M (2012) The blockage of immune checkpoints in cancer immunotherapy. *Nat Rev Cancer* 12: 252-64.

PCT Publication No. WO 2008/156712, published Dec. 24, 2008 by Organon NV.

PCT Publication No. WO 2012/145493, published Oct. 26, 2012 by Amplimmune, Inc.

PCT Publication No. WO 2013/173223, published Nov. 21, 2013 by Bristol-Myers Squibb Co.

PCT Publication No. WO 2014/179664, published Nov. 6, 2014 by AnaptysBio, Inc.

PCT Publication No. WO 2014/194302, published Dec. 4, 2014 by Sorrento Therapeutics, Inc.

PCT Publication No. WO 2014/206107, published Dec. 31, 2014 by Shanghai Junshi Biosciences Inc.

PCT Publication No. WO 2015/035606, published Mar. 19, 2015 by Beigene, Ltd.
PCT Publication No. WO 2015/085847, published Jun. 18, 2015 by Shanghai Hengrui Pharmaceutical Co., Ltd.
PCT Publication No. WO 2015/112800, published Jul. 30, 2015 by Regeneron Pharmaceuticals, Inc.
PCT Publication No. WO 2015/112900, published Jul. 30, 2015 by Dana-Farber Cancer Institute, Inc. and Novartis AG
PCT Publication No. WO 2016/106159, published Jun. 30, 2016 by Enumeral Biomedical Holdings, Inc.
PCT Publication No. WO 2006/121168, published Nov. 16, 2006 by ONO Pharmaceutical Co., Ltd. and Medarex, Inc.
PCT Publication No. WO 2016/149201, published Sep. 22, 2016 by Cytomx Therapeutics, Inc.
PCT Publication No. WO 2016/197367, published Dec. 15, 2016 by Wuxi Biologics (Shanghai) Co. Ltd.
PCT Publication No. WO 2017/020291, published Feb. 9, 2017 by Wuxi Biologics (Shanghai) Co. Ltd.
PCT Publication No. WO 2017/020858, published Feb. 9, 2017 by Wuxi Biologics (Shanghai) Co. Ltd.
PCT Publication No. WO 2017/024465, published by Feb. 16, 2017 Innovent Biologics (Suzhou) Co., Ltd.
PCT Publication No. WO 2017/024515, published Feb. 16, 2017 by Wuxi Biologics (Cayman) Inc.
PCT Publication No. WO 2017/025016, published Feb. 16, 2017 by Innovent Biologics (Suzhou) Co., Ltd.
PCT Publication No. WO 2017/025051, published Feb. 16, 2017 by Wuxi Biologics (Cayman) Inc.
PCT Publication No. WO 2017/034916, published Mar. 2, 2017 by Eli Lilly and Co.
PCT Publication No. WO 2017/040790, published Mar. 9, 2017 by Agenus Inc.
PCT Publication No. WO 2017/106061, published Jun. 22, 2017 by Macrogenics, Inc.
PCT Publication No. WO 2017/123557, published Jul. 20, 2017 by Armo Biosciences, Inc.
PCT Publication No. WO 2017/132827, published Aug. 10, 2017 by Innovent Biologics (Suzhou) Co., Ltd.
PCT Publication No. WO 2017/133540, published Aug. 10, 2017 by Innovent Biologics (Suzhou) Co., Ltd.
Pianko M J, Liu Y, Bagchi S, Lesokhin A M (2017) Immune checkpoint blockade for hematologic malignancies: a review. *Stem Cell Investig* 4:32.
Ramakrishna V, Sundarapandiyan K, Zhao B et al. (2015) Characterization of the human T cell response to in vitro CD27 costimulation with varlilumab. *J Immunother Cancer* 3:37.
Roberts D J, Franklin N A, Kingeter L M et al. (2010) Control of established melanoma by CD27 stimulation is associated with enhanced effector function and persistence, and reduced PD-1 expression, of tumor infiltrating CD8+ T cells. *J Immunother* 33:769-79.
Sakanishi T, Yagita H (2010) Anti-tumor effects of depleting and non-depleting anti-CD27 mAbs in immune-competent mice. *Biochem Biophys Res Commun* 393:829-35.
Salzer E, Daschkey S, Choo S et al. (2013) Combined immunodeficiency with life-threatening EBV-associated lymphoproliferative disorder in patients lacking functional CD27. *Haematologica* 98:473-8.
Sanchez P J, McWilliams J A, Haluszczak C et al. (2007) Combined TLR/CD40 stimulation mediates potent cellular immunity by regulating dendritic cell expression of CD70 in vivo. *J Immunol* 178:1564-72.
Sanborn R E, Pishvaian M J, Kluger H M, Callahan M K et al. (2017) Clinical results with combination of anti-CD27 agonist antibody, varlilumab, with anti-PD1 antibody nivolumab in advanced cancer patients. *J Clin Oncol* 35(15) Suppl.:3007.
Taraban V Y, Rowley T F, Al-Shamkhani A (2004) Cutting edge: a critical role for CD70 in CD8 T cell priming by CD40-licensed APCs. *J Immunol* 173:6542-6.
U.S. Pat. No. 6,808,710, issued Oct. 26, 2004 to Wood et al.
U.S. Pat. No. 7,488,802, issued Feb. 10, 2009 to Collins et al.
U.S. Pat. No. 7,943,743, issued May 17, 2011 to Korman et al.
U.S. Pat. No. 7,767,429, issued Aug. 3, 2010 to Bookbinder et al.
U.S. Pat. No. 8,008,449, issued Aug. 30, 2011 to Korman et al.
U.S. Pat. No. 8,168,757, issued May 1, 2012 to Finnefrock et al.
U.S. Pat. No. 8,217,149, issued Jul. 10, 2012 to Irving et al.
U.S. Pat. No. 8,354,509, issued Jan. 15, 2013 to Carven et al.
U.S. Pat. No. 8,779,108, issued Jul. 15, 2014 to Queva et al.
U.S. Pat. No. 9,175,082, issued Nov. 3, 2015 to Zhou et al.
U.S. Pat. No. 9,205,148, issued Dec. 8, 2015 to Langermann et al.
U.S. Pat. No. 9,624,298, issued Apr. 18, 2017 to Nastri et al.
U.S. Pat. No. 9,938,345, issued Apr. 10, 2018 to Papadopoulos et al.
U.S. Pat. No. 9,987,500, issued Jun. 5, 2018 to Papadopoulos et al.
U.S. Publication No. 2015/0079109, published Mar. 19, 2015 by Li et al.
U.S. Publication No. 2016/0272708, published Sep. 22, 2016 by Chen et al.
van Gisbergen K P, Klarenbeek P L, Kragten N A, et al. (2011) The costimulatory molecule CD27 maintains clonally diverse CD8 (+) T cell responses of low antigen affinity to protect against viral variants. *Immunity* 35:97-108.
van Montfrans J M, Hoepelman A I, Otto S et al. (2012) CD27 deficiency is associated with combined immunodeficiency and persistent symptomatic EBV viremia. *Allergy Clin Immunol* 129:787-93.
Wajant H (2016) Therapeutic targeting of CD70 and CD27. *Expert Opin Ther Targets* 15:1-15.
Wang C, Thudium K B, Han M, Wang X T et al. (2014) In vitro characterization of the anti-PD-1 antibody nivolumab, BMS-936558, and in vivo toxicology in non-human primates. *Cancer Imm Res* 2(9):846-56.
Weber J (2010) Immune checkpoint proteins: a new therapeutic paradigm for cancer-preclinical background: CTLA-4 and PD-1 blockade. *Semin Oncol* 37(5): 430-9.
Wei H, Mo J, Tao L, Russell R G, Tymiak A A et al. (2014) Hydrogen/deuterium exchange mass spectrometry for probing higher order structure of protein therapeutics: methodology and applications. *Drug Discov Today* 19:95-102.
Wolchok J D, Weber J S, Maio M, Neyns B, Harmankaya K et al. (2013) Four-year survival rates for patients with metastatic melanoma who received ipilimumab in phase II clinical trials. *Ann Oncol* 24(8):2174-80.
Wu T T, Kabat E A (1970) An analysis of the sequences of the variable regions of Bence Jones proteins and myeloma light chains and their implications for antibody complementarity. *J Exp Med* 132:211-50.
Yan Y, Chen G, Wei H, Huang R, Mo J et al. (2014) Fast photochemical oxidation of proteins (FPOP) maps the epitope of EGFR binding to adnectin. *J Am Soc Mass Spec* 25:2084-92.

Yao S, Zhu Y, Chen L (2013) Advances in targeting cell surface signalling molecules for immune modulation. *Nature Rev Drug Discov* 12:130-46.

Zhang F, Wei H, Wang X, Bai Y, Wang P et al. (2017) Structural basis of a novel PD-L1 nanobody for immune checkpoint blockade. *Cell Discov* 3:17004.

---

What is claimed is:

1. An agonist monoclonal antibody or an antigen-binding portion thereof that specifically binds to human CD27, wherein the antibody or portion thereof comprises:
   (a) a heavy chain variable region ($V_H$) comprising a CDR1 comprising consecutively linked amino acids having the sequence set forth as SEQ ID NO: 2, a CDR2 comprising consecutively linked amino acids having the sequence set forth as SEQ ID NO: 3, and a CDR3 comprising consecutively linked amino acids having the sequence set forth as SEQ ID NO: 4; and
   (b) a light chain variable region ($V_L$) comprising a CDR1 comprising consecutively linked amino acids having the sequence set forth as SEQ ID NO: 5, a CDR2 comprising consecutively linked amino acids having the sequence set forth as SEQ ID NO: 6, and a CDR3 comprising consecutively linked amino acids having the sequence set forth as SEQ ID NO: 7.

2. The agonist monoclonal antibody or antigen-binding portion thereof of claim 1 that specifically binds to an epitope located within discontinuous regions spanning approximately amino acid residues 21-41 and 52-57 of human CD27, the sequence of which is set forth as SEQ ID NO: 1, as determined by hydrogen-deuterium exchange mass spectrometry (HDX-MS) and/or fast photochemical oxidation of proteins (FPOP) epitope mapping.

3. The agonist monoclonal antibody or antigen-binding portion thereof of claim 1, which comprises a $V_H$ comprising consecutively linked amino acids having the sequence set forth as SEQ ID NO: 8; and/or a $V_L$ comprising consecutively linked amino acids having the sequence set forth as SEQ ID NO: 9.

4. The agonist monoclonal antibody or antigen-binding portion thereof of claim 1, which comprises a heavy chain comprising consecutively linked amino acids having the sequence set forth as SEQ ID NO: 12 and/or a light chain comprising consecutively linked amino acids having the sequence set forth as SEQ ID NO: 13.

5. An agonist monoclonal antibody that specifically binds to human CD27 and does not block binding to its CD70 ligand, wherein the monoclonal antibody is the monoclonal antibody designated BMS-986215, which comprises a heavy chain comprising consecutively linked amino acids having the sequence set forth as SEQ ID NO: 12 and a light chain comprising consecutively linked amino acids having the sequence set forth as SEQ ID NO: 13.

6. The agonist monoclonal antibody or antigen-binding portion thereof of claim 1, which does not block binding to its CD70 ligand as measured by surface plasmon resonance (SPR) or flow cytometry.

7. The agonist monoclonal antibody or antigen-binding portion thereof of claim 1, which comprises a heavy chain constant region which is of a human IgG1, IgG2, IgG3, or IgG4 isotype.

8. The agonist monoclonal antibody or antigen-binding portion thereof of claim 7, which is of a human IgG1 isotype.

9. The antigen-binding portion of claim 1, which is an antibody fragment or a single chain antibody, wherein the antibody fragment is selected from the group consisting of a Fab, F(ab')$_2$, a Fd and a Fv fragment;
   and wherein the single chain antibody is selected from the group consisting of a single-chain variable fragment (scFv), a divalent scFv (di-scFv), a diabody, a minibody;
   and any combination thereof of said antibody fragment or single chain antibody.

10. The agonist monoclonal antibody or antigen-binding portion thereof of claim 3, which has one or more characteristics chosen from:
    (a) does not specifically bind to rat CD27 and/or mouse CD27 as measured by SPR or flow cytometry;
    (b) does not specifically bind to one or more TNF receptor superfamily members selected from the group consisting of CD30, HVEM, DR5, 4-1BB, CD40, OX40, GITR, and any combination thereof;
    (c) does not specifically bind to one or more human tissues at concentrations up to 10 µg/mL, wherein the human tissues are selected from the group consisting of thyroid, lung, skin, uterus, prostate, liver, kidney, pancreas, adrenal, pituitary, placenta, testis, cerebrum, cerebellum, heart, peripheral nerve, and any combination thereof;
    (d) is capable of inducing proliferation and/or IFN-γ secretion in a CHO-svCD3-CD32A assay;
    (e) is capable of inducing proliferation of CD4$^+$CD45RO$^+$ memory T cells;
    (f) is capable of increasing IL-2 release from *staphylococcus* enterotoxin B (SEB)-stimulated human peripheral blood mononuclear cells (PBMCs);
    (g) is capable of increasing IL-2 release at least two-fold when combined with an anti-Programmed Death-1 (anti-PD-1) antibody;
    (h) is capable of reversing Treg-mediated suppression of co-cultured CD4$^+$responder T cells in the presence of monocyte-derived dendritic cells (MDDC) and soluble OKT3; and
    (i) is capable of potentiating the proliferation of human T cells and induction of IFN-γ secretion by soluble CD70.

11. The agonist monoclonal antibody or antigen-binding portion thereof of claim 3, wherein the monoclonal antibody or antigen-binding portion thereof:
    (a) binds to human CD27 with a $K_D$ of about 100 nM or lower as determined by surface plasmon resonance (SPR); and/or
    (b) induces NF-κB and MAPK signaling in naïve and pre-activated human T cells stimulated by an anti-CD3 Ab and an anti-CD28 antibody with an $EC_{50}$ of about 0.5 nM or lower.

12. The agonist monoclonal antibody or antigen-binding portion thereof of claim 3, wherein the monoclonal antibody or antigen-binding portion thereof:
    (a) binds to human T cells with an $EC_{50}$ of about 0.1 nM or lower as determined by flow cytometry; and/or
    (b) binds to cynomolgus T cells with $EC_{50}$ of about 0.5 nM or lower as determined by flow cytometry.

13. The agonist monoclonal antibody or antigen-binding portion thereof of claim 3, which:
    (a) is a human antibody or a fragment thereof;
    (b) is a chimeric antibody or a fragment thereof;
    (c) induces proliferation and/or IFN-γ secretion in a CHO-svCD3-CD32A assay with an $EC_{50}$ of about 0.05 nM or lower;
    (d) induces proliferation of CD4$^+$CD45RO$^+$memory T cells with an $EC_{50}$ of about 0.01 nM or lower and/or induces IFN-γ secretion with an $EC_{50}$ of about 0.05 nM or lower;
    (e) increases IL-2 release from SEB-stimulated human PBMCs by greater than about 50% in the presence of a cross-linker, or by at least about two-fold when combined with an anti-PD-1 antibody;
    (f) reverses Treg-mediated suppression of co-cultured CD4$^+$responder T cells in the presence of MDDC and soluble OKT by at least about 70%; or (g) potentiates the proliferation of human T cells by soluble CD70 with an $EC_{50}$ of about 0.01 nM or lower, and/or potentiates the induction of IFN-γ secretion by soluble CD70 with an $EC_{50}$ of about 0.01 nM or lower.

14. The agonist monoclonal antibody or antigen-binding portion thereof of claim 11, wherein the monoclonal antibody or antigen-binding portion thereof:
   (a) binds to human CD27 with a $K_D$ of between about 40 nM and about 45 nM at about 37° C. and/or between about 13 nM and 16 nM at about 25° C.; and/or
   (b) induces NF-κB and MAPK signaling with an $EC_{50}$ of between about 0.02 nM and about 0.25 nM.

15. The agonist monoclonal antibody or antigen-binding portion thereof of claim 12, wherein the monoclonal antibody or antigen-binding portion thereof binds to human T cells with an $EC_{50}$ of between about 0.025 nM and about 0.075 nM, and/or binds to cynomolgus T cells with $EC_{50}$ of between about 0.025 nM and about 0.4 nM.

16. The agonist monoclonal antibody or antigen-binding portion thereof of claim 13, which:
   (a) induces proliferation and/or IFN-γ secretion in a CHO-svCD3-CD32A assay with an $EC_{50}$ of between about 0.001 nM and about 0.03 nM;
   (b) induces proliferation of $CD4^+CD45RO^+$ memory T cells with an $EC_{50}$ of between about 0.004 nM to about 0.006 nM and/or induces IFN-γ secretion in $CD4^+CD45RO^+$ memory T cells with an $EC_{50}$ of between about 0.005 nM and about 0.03 nM, and/or
   (c) potentiates the proliferation of human T cells by soluble CD70 with an $EC_{50}$ of between about 0.001 nM and about 0.01 nM and/or potentiates the induction of IFN-γ secretion by soluble CD70 with an $EC_{50}$ of between about 0.001 nM and about 0.01 nM.

17. A composition comprising
the agonist monoclonal antibody or antigen-binding portion thereof of claim 1
and
a pharmaceutically acceptable carrier.

18. The composition of claim 17, further comprising an additional antibody or an antigen-binding portion thereof, optionally wherein the additional antibody or antigen-binding portion thereof is chosen from an anti-PD-1 antibody, anti-Programmed Death Ligand-1 (PD-L1) antibody, anti-Cytotoxic T-Lymphocyte Antigen-4 (CTLA-4) antibody, anti-Lymphocyte Activation Gene-3 (LAG-3) antibody, anti-B and T lymphocyte attenuator (BTLA) antibody, anti-T cell Immunoglobulin and Mucin domain-3 (TIM-3) antibody, anti-Killer Immunoglobulin-like Receptor (KIR) antibody, anti-Killer cell Lectin-like Receptor G1 (KLRG-1) antibody, anti-adenosine A2a receptor (A2aR) antibody, anti-Natural Killer Cell Receptor 2B4 (CD244) antibody, anti-CD160 antibody, T cell Immunoreceptor with Ig and ITIM domains (TIGIT) antibody, V-domain Ig Suppressor of T cell Activation (VISTA) antibody, nivolumab, pembrolizumab, cemiplimab, atezolizumab, durvalumab, avelumab, the antibody designated BMS-936559, an anti-Inducible T cell Co-Stimulator (ICOS) antibody, anti-CD137 (4-1BB) antibody, anti-CD134 (OX40) antibody, anti-CD27 antibody, anti-Glucocorticoid-Induced TNFR-Related protein (GITR) antibody, anti-Herpes Virus Entry Mediator (HVEM) antibody, and any combination thereof.

19. A kit for treating a subject afflicted with a cancer or for inhibiting growth of tumor cells in a subject, the kit comprising:
   (a) one or more dosages ranging from about 0.1 to about 20 mg/kg body weight of the monoclonal antibody or antigen-binding portion thereof of claim 1; and
   (b) instructions for using the one or more dosages in a method for treating a subject afflicted with a cancer.

20. The kit of claim 19, further comprising one or more dosages of an additional therapeutic agent.

21. An immunoconjugate comprising the agonist monoclonal antibody or antigen-binding portion thereof of claim 1, linked to a therapeutic agent.

22. A bispecific molecule comprising the agonist monoclonal antibody or antigen-binding portion thereof of claim 1, linked to a binding domain that has a different binding specificity than the monoclonal antibody or antigen binding portion thereof.

23. The immunoconjugate of claim 21, wherein the therapeutic agent is a cytotoxin or a radioactive isotope.

24. A composition comprising the immunoconjugate of claim 21 and a pharmaceutically acceptable carrier.

25. A composition comprising the bispecific molecule of claim 22 and a pharmaceutically acceptable carrier.

* * * * *